US011857538B2

(12) United States Patent
Shah et al.

(10) Patent No.: US 11,857,538 B2
(45) Date of Patent: Jan. 2, 2024

(54) STABLE PILOCARPINE FORMULATIONS WITH MODIFIED BUFFER CHARACTERISTICS AND RELATED METHODS

(71) Applicant: Somerset Therapeutics, LLC, Hollywood, FL (US)

(72) Inventors: Mandar V. Shah, Rockaway, NJ (US); Veerappan Subramanian, Warren, NJ (US); Ilango Subramanian, Warren, NJ (US); Aman Trehan, Hillsborough, NJ (US)

(73) Assignee: Somerset Therapeutics, LLC, Hollywood, FL (US)

( * ) Notice: Subject to any disclaimer, the term of this patent is extended or adjusted under 35 U.S.C. 154(b) by 0 days.

(21) Appl. No.: 18/154,524

(22) Filed: Jan. 13, 2023

(65) Prior Publication Data
US 2023/0263775 A1    Aug. 24, 2023

Related U.S. Application Data

(60) Provisional application No. 63/299,883, filed on Jan. 14, 2022, provisional application No. 63/299,870, filed on Jan. 14, 2022, provisional application No. 63/299,877, filed on Jan. 14, 2022.

(51) Int. Cl.
| | |
|---|---|
| *A61K 31/4178* | (2006.01) |
| *A61K 9/08* | (2006.01) |
| *A61K 9/00* | (2006.01) |
| *A61K 47/18* | (2017.01) |
| *A61K 47/36* | (2006.01) |
| *A61K 47/26* | (2006.01) |
| *A61K 9/06* | (2006.01) |
| *A61K 47/12* | (2006.01) |

(52) U.S. Cl.
CPC ........ *A61K 31/4178* (2013.01); *A61K 9/0048* (2013.01); *A61K 9/06* (2013.01); *A61K 9/08* (2013.01); *A61K 47/12* (2013.01); *A61K 47/18* (2013.01); *A61K 47/186* (2013.01); *A61K 47/26* (2013.01); *A61K 47/36* (2013.01)

(58) Field of Classification Search
CPC .... A61K 31/4178; A61K 9/0048; A61K 9/06; A61K 9/08; A61K 47/12; A61K 47/18; A61K 47/186; A61K 47/26; A61K 47/36
See application file for complete search history.

(56) References Cited

U.S. PATENT DOCUMENTS

| | | |
|---|---|---|
| 6,410,544 B1 | 6/2002 | Gwon |
| 8,299,079 B2 | 10/2012 | Kaufman |
| 10,610,518 B2 | 4/2020 | Robinson |
| 10,639,297 B2 | 5/2020 | Feinbaum |
| 11,285,134 B2 | 3/2022 | Robinson |
| 2019/0008832 A1* | 1/2019 | Pinelli ................. A61K 31/4178 |
| 2020/0246310 A1* | 8/2020 | Pitlick .................... A61K 45/06 |

FOREIGN PATENT DOCUMENTS

WO    WO 2022/169959    8/2022

OTHER PUBLICATIONS

Gil-Cazorla et al., 2016, British Journal of Ophthalmology 100(1): 62-70, Apr. 23, 2015, Gil-Cazorla, Raquel.
Charman, 2014, Ophthalmic & Physiological Optics: the Journal of the College of Optometrists 34(4): 397-426, Apr. 10, 2014, Charman, W. Neil.
Charman, 2014, Ophthalmic & Physiological Optics: the Journal of the College of Optometrists 34(1): 8-29, Nov. 10, 2013, Charman, W. Neil.
Katz, et al. "Presbyopia—A Review of Current Treatment Options and Emerging Therapies." Clin Ophthalmol. 2021; 15:2167-2178, May 24, 2021, Katz, James A.
Patel et al., 2007, Community Health/International Centre for Eye Health 20(63): 40-41, Sep. 1, 2007, Patel, Ilesh.
Goertz et al., 2014, Acta Ophthalmologica 92(6): 497-500, Nov. 13, 2013, Goertz, Ariana D.
Frick et al., 2015, Ophthalmology 122(8): 1706-10, Aug. 15, 2015, Frick, Kevin D.
Non-Final Office Action dated Apr. 18, 2023 for U.S. Appl. No. 18/167,059, dated Apr. 18, 2013, Anderson, James D.
Pilocarpine HS Product Label (Alcon Laboratories, Inc., Revised Oct. 2007, 7 pages) (Year: 2007), Oct. 1, 2007, Pilocarpine, Label.
Non-Final Office Action dated Apr. 11, 2023 for U.S. Appl. No. 18/167,057, dated Apr. 11, 2023, Anderson, James D.
Vuity Product Label (Allergan, Revised Oct. 2021, 8 pages) (Year: 2021), Oct. 1, 2021, Vuity, Label.

(Continued)

*Primary Examiner* — Robert A Wax
*Assistant Examiner* — Quanglong N Truong
(74) *Attorney, Agent, or Firm* — Transformative Legal LLC; Len S. Smith; Denise M. Brown

(57) ABSTRACT

Disclosed herein, are, among other things, stable, pharmaceutically acceptable and ophthalmologically suitable reduced buffer content and reduced buffering capacity pilocarpine compound compositions. In aspects, such compositions comprise therapeutically effective amounts of a pilocarpine compound, an effective amount of a uniform buffer component, wherein the concentrations of pilocarpine compound and uniform buffer component are limited to specific relative amounts and wherein the uniform buffer component is defined by one or more markedly distinguishing characteristics from buffers used in developed pilocarpine products (e.g., a unique pKa and/or concentration). Aspects of the invention include compositions defined by unique concentrations of such and other ingredients. Such compositions surprisingly exhibit pharmaceutically acceptable stability and, in aspects, stability equal to or statistically significantly greater than that of one or more on-market/developed reference product(s). Further, the invention provides methods of manufacturing such and similar compositions, and methods of their use in treating ocular conditions such as presbyopia.

20 Claims, No Drawings

(56) References Cited

OTHER PUBLICATIONS

Alphagan Label, Reference ID:3906086, Revised Mar. 2016. Also Alphagan Product Label (Allergan, Revised Mar. 2016, 8 pages), Mar. 1, 2016, Alphagan, Label.
ISOPTO Product Label (Alcon Laboratories, Inc., Revised Jun. 2010, 5 pages) (Year: 2010), Jun. 1, 2010, Isopto, Label.
Non-Final Office Action dated May 10, 2023 for U.S. Appl. No. 18/167,056, dated May 10, 2023, Alawadi, Sarah.

\* cited by examiner

STABLE PILOCARPINE FORMULATIONS WITH MODIFIED BUFFER CHARACTERISTICS AND RELATED METHODS

CROSS REFERENCE TO RELATED APPLICATIONS

This patent application claims priority to U.S. Provisional Application No. 63/299,870 filed Jan. 14, 2022, entitled "Citrate-Free Pilocarpine Compositions and Related Methods," U.S. Provisional Application No. 63/299,877 filed Jan. 14, 2022, entitled "Borate-Free Pilocarpine Compositions and Related Methods," and U.S. Provisional Application No. 63/299,883 filed Jan. 14, 2022, entitled "Borate and Citrate Buffer-Free Pilocarpine Compositions and Related Methods." This application claims the benefit of priority to, and incorporates by reference the entirety of, the above-referenced priority applications.

FIELD OF THE INVENTION

The invention primarily relates to pharmaceutical compositions comprising pilocarpine compound(s), the use of such compositions in treating ophthalmic conditions (such as presbyopia), and processes for manufacturing such or similar compositions.

BACKGROUND OF THE INVENTION

Presbyopia, known as age-related blurry near vision, is typically caused by age-related eye deterioration. Presbyopia typically develops as a person ages and is associated with a natural progressive loss of visual accommodation. A presbyopic eye loses the ability to rapidly and easily focus on objects at near distances. Presbyopia progresses over the lifetime of an individual, usually becoming noticeable, and, e.g., bothersome, after the age of 45 years.

Presbyopia is the most common physiological change occurring in the adult eye and the condition can significantly affect quality of life and productivity when left uncorrected (See, e.g., Frick et al., 2015, Ophthalmology 122(8): 1706-10; Goertz et al., 2014, Acta Ophthalmologica 92(6): 497-500; and Patel et al., 2007, Community Eye Health/International Centre for Eye Health 20(63): 40-41). The main symptom of this condition is a progressive blurring of vision when performing near tasks (e.g., reading, sewing, viewing a computer screen, etc.). This can occur in the absence of any visual symptoms associated with distance vision. According to Katz, et. al., in "Presbyopia—A Review of Current Treatment Options and Emerging Therapies," Clin Ophthalmol. 2021; 15:2167-2178, and references cited therein, about 85% of people aged 40 years or older develop presbyopia. In 2015, it was estimated that 1.8 billion people globally suffered from presbyopia and its prevalence was predicted to reach approximately 2.1 billion in 2030 (Katz, sic.)

For many years, the only means for addressing presbyopia has been corrective lens systems and surgical interventions. The methods available for correcting presbyopia have provided fixed and variable-focus lens systems ("glasses" or "spectacles" or contact lenses with monofocal, bifocal or multifocal design), and surgical procedures which modify the optics of the cornea, replace the crystalline lens with different fixed optics, or attempt to at least partially restore active accommodation (See, e.g., Charman, 2014, Ophthalmic & Physiological Optics: the Journal of the College of Optometrists 34(1): 8-29; Charman, 2014, Ophthalmic & Physiological Optics: the Journal of the College of Optometrists 34(4): 397-426; and, e.g., Gil-Cazorla et al., 2016, British Journal of Ophthalmology 100(1): 62-70). However, corrective lens systems can be cumbersome or provide inadequate treatment, while surgical methods can be invasive and bring with them additional risks and potential side effects. For example, a patient may have trouble with night vision after a surgical intervention to treat presbyopia.

Topical pharmaceutical ophthalmic preparations have been marketed for a number of different ophthalmic conditions for many years. Cholinergic agonists, such as the compound pilocarpine, were known for their ability to lower intraocular pressure (IOP), e.g., useful in the treatment of primary open angle glaucoma, and such compounds were commonly used treatments for lowering intraocular pressure (IOP) until the late 1970s.

In subsequent decades, and with the introduction of topical carbonic anhydrase inhibitors, alpha agonists, and prostaglandin agonists for lowering IOP, e.g., particularly the introduction of timolol in 1978, pilocarpine became less frequently prescribed, as newer drugs had a much lower incidence of side effects such as, e.g., reduced visual acuity and ocular discomfort (Allingham et al., Shields' Textbook of Glaucoma, $5^{th}$ edition, Lippincott Williams & Wilkins (Philadelphia), 2005, pp. 501-503). There has remained, however, a void in treatment options for ameliorating or reducing presbyopia in patients that do not wish to undergo surgery (intra-ocular lenses, laser ablation, etc.) or use corrective glasses, as no topical solution has been available. This, in part, is due to the broadly accepted challenges facing ophthalmological composition formulators; that is, generating stable, safe, tolerable, and efficacious compositions, as it has been well demonstrated that even slight modifications of compositional elements leads to remarkably different results.

In late 2021, pilocarpine was approved by the United States Food and Drug Administration (NDA Number 214028) for the treatment of presbyopia. Abbvie, Inc. currently markets a product, VUITY® (approved under U.S. FDA NDA Number 214028), a 1.25% ophthalmic solution of pilocarpine. The product presently marketed as VUITY® represents the first and only FDA approved eye drop to treat this common and progressive eye condition affecting 128 million Americans, at least half of the U.S. adult population. VUITY® is indicated for the treatment of presbyopia in adults with dosage of one drop in each eye once daily.

Each single mL of VUITY® contains pilocarpine hydrochloride 1.25% (12.5 mg) as the active ingredient, equivalent to 1.06% (10.6 mg) pilocarpine free base. Inactive ingredients present in VUITY® include benzalkonium chloride (0.0075%), boric acid, sodium citrate dihydrate, sodium chloride, purified water, and may also include hydrochloric acid and/or sodium hydroxide for pH adjustment to a pH of between 3.5 and 5.5, if necessary.

U.S. Pat. No. 6,410,544 (Allergan) discloses a method for increasing or decreasing parasympathetic/cholinergic/ciliary tonic contraction in order to restore the resting portion of the eye and allow normal positive and negative accommodation includes administering to a myopic or hyperopic presbyope. The patent discloses pilocarpine as a muscarinic agent in a concentration 0.001-2% accompanied by a high amount of benzalkonium chloride (0.01%). The examples and abbreviated clinical study disclose use of pilocarpine at either 0.1% or 0.3%.

U.S. Pat. No. 10,610,518 (also to Allergan), an Orange Book-listed patent for the U.S. FDA approved and marketed product VUITY®, claims a method of treating an ocular condition in a patient in need thereof, comprising administering to the patient a pharmaceutically acceptable ophthalmic composition comprising pilocarpine hydrochloride at a concentration of 1.0 to 1.5% w/v, 1.0% w/v boric acid, 0.015% w/v sodium citrate dihydrate, 0.03 to 0.37% w/v sodium chloride, hydrochloric acid and/or sodium hydroxide, and water. U.S. Pat. No. 11,285,134 (Allergan) is also an Orange Book-listed patent for VUITY® and is a continuation of U.S. Pat. No. 10,610,518.

U.S. Pat. No. 10,639,297 (Orasis Pharma.) discloses an ophthalmic pharmaceutical composition consisting of pilocarpine or a pharmaceutically acceptable salt thereof at a concentration of about 0.01% to about 0.45%, a lubricant, and one or more pharmaceutically acceptable carriers. The lubricant is selected from the group consisting of hyaluronic acid or pharmaceutically acceptable salt thereof, cellulose, carboxymethyl cellulose sodium, hydroxyethyl cellulose, methylcellulose, dextran, gelatin, a polyol, glycerin, polyethylene glycol 300, polyethylene glycol 400, polysorbate, propylene glycol, polyvinyl alcohol, hydroxypropyl methylcellulose, or povidone, or mixtures thereof.

All such compositions comprise a buffer component as is commonly found in the art in connection with related products/formulations. For example, VUITY® comprises a two-component buffer system comprising two buffer component constituents (boric acid and sodium citrate dihydrate).

The VUITY® label provides a list of possible side effects of the composition as determined by clinical trials, including, e.g., greater than 5% of all users experiencing headache and conjunctival hyperemia; and blurred vision, eye pain, visual impairment, eye irritation, and increased lacrimation experienced by 1.5% of clinical trial patients.

Remarkably, the difficulty of generating efficacious ophthalmologically suitable formulations continues to persist, as is demonstrated by WO 2022/169959 (Sydnexis, Inc.). The WO 2022/169959 publication is put forth in response to the fact that formulations continue to suffer from significant stability problems. The application seeks to overcome such known stability challenges primarily via use of deuterated water. WO 2022/169959 discloses ophthalmic compositions comprising one or more ophthalmic agents (e.g., aceclidine, pilocarpine, and tropicamide or combinations thereof) for the treatment of presbyopia, wherein compositions utilize deuterated water to provide improved stability and, further, at least in part, address the known challenge of ophthalmic compositions commonly being irritating to recipient eye(s) by reducing the buffer capacity of such proposed compositions. In reducing the buffer capacity via use of deuterated water, compositions allegedly adjust to the pH of the natural eye environment more quickly, hence potentially reducing associated irritation resulting in tearing. While disclosing numerous possible active ingredients, the WO 2022/169959 art specifically discloses pilocarpine compositions, and exemplifies the comparison of pilocarpine compositions comprising deuterated and non-deuterated water (see Figures 1 and 2 therein). The data demonstrate the benefit of using deuterated water in improving stability of ophthalmic compositions, a challenge which is, again, well recognized in the art and the source of frustration for ophthalmic composition formulators. As stated previously, as is also well recognized in the art, even the slightest of modifications to ophthalmic compositions, e.g., an amount of API, excipient, or both, often yields detrimental effect(s) in terms of stability, safety, efficacy, tolerability, etc. and combinations thereof. In fact the WO 2022/169959 art exemplifies this fact, as even simply modifying the water of the composition, not even an API or an excipient, yields very different performance results. While deuteration is not the expressly limited teaching, any additional disclosure is generally couched in such light. The publication provides disclosure of a limited number of ophthalmological compositions of which some may contain pilocarpine. Within such examples, like that of other art cited herein, the compositions are generally limited to very specific combinations of components/compounds. The disclosure demonstrates that the sensitivity of the ophthalmic environment, the repercussions of common side effects of ophthalmic compositions, and the ability to address such elements while providing a stable, safe, and efficacious composition continue to make formulation in this field a treacherous endeavor.

With limited options, in fact no practically available options other than VUITY® in the United States, for the topical treatment of presbyopia, patients are left to either endure side effects associated with use of VUITY® or are left with surgical intervention(s) or corrective lenses for the treatment of presbyopia.

Construction, Terms, and Acronyms

This section offers guidelines for reading this disclosure. The intended audience for this disclosure ("readers") are persons having ordinary skill in the practice of technologies discussed or used herein. Readers may also be called "skilled persons," and such technologies called "the art." Terms such as "understood," "known," and "ordinary meaning," refer to the general knowledge of skilled persons.

The term "uncontradicted" means not contradicted by this disclosure, logic, or plausibility based on knowledge of skilled persons.

Disclosed here are several different but related exemplary aspects of the invention (referred also to as, e.g., "cases," "facets," or "embodiments"). The invention encompasses all aspects, as described individually and as can be arrived at by any combination of such individual aspects. The breadth and scope of the invention should not be limited by any exemplary embodiment(s). No language in this disclosure should be construed as indicating any element/step is essential to the practice of the invention unless such a requirement is explicitly stated. Uncontradicted, any aspect(s) can be combined with any other aspect(s).

Uncontradicted, all technical/scientific terms used here generally have the same meanings as commonly understood by skilled persons, regardless of any narrower examples or descriptions provided here (including any term introduced initially in quotations). However, aspects characterized by the inclusion of elements, steps, etc., associated with specific descriptions provided here are distinct embodiments of the invention. Uncontradicted, disclosure of any aspect using known terms, which terms are narrowed by example or otherwise in this disclosure, implicitly discloses related aspects in which such terms are alternatively interpreted using the broadest reasonable interpretation of skilled persons.

Uncontradicted, "or" means "and/or" here, regardless of any occasional inclusion of "and/or" (e.g., phrases such as "A, B, or C" and "A, B, and/or C" simultaneously disclose aspects including (1) all of A, B, and C; (2) A and C; (3) A and B; (4) B and C; (5) only A; (6) only B; and (7) only C (and also support sub-groupings, such as "A or B," "A or C," etc.)).

Uncontradicted, "also" means "also or alternatively." Uncontradicted, "here" & "herein" mean "in this disclosure." The term "i.a." means "inter glia" or "among other things." "Also known as" is abbreviated "aka" or "AKA." "Elsewhere" means "elsewhere herein."

For conciseness, symbols are used where appropriate. E.g., "&" is used for "and," & "~" for "about." Symbols such as < and > are given their ordinary meaning (e.g., "≤" means "less than or equal to" & "≥" means "greater than or equal to"). A slash "/" can represent "or" ("A/B" means "A or B") or identify synonyms of an element, as will be clear from context.

The inclusion of "(s)" after an element or a step indicates that ≥1 of such an element is present, step performed, and the like. E.g., "element(s)" means both 1 element or ≥2 elements, with the understanding that each thereof is an independent aspect of the invention.

Use of the abbreviation "etc." (or "et cetera") in association with a list of elements/steps means any or all suitable combinations of the recited elements/steps or any known equivalents of such recited elements/steps for achieving the function(s) of such elements/steps that are known in the art. Terms such as "and combinations," or "or combinations" regarding listed elements/steps means any or all possible/suitable combinations of such elements/steps.

Aspects may be described as suitable for use(s) disclosed herein. Uncontradicted, terms such as "suitability" means acceptable or appropriate for performing a particular function/achieving particular state(s)/outcome(s), and typically means effective, practical, and non-deleterious/harmful in the context the term is used. E.g., uncontradicted, the term "suitable" means appropriate, acceptable, or in contexts sufficient, or providing at least generally or substantially all of an intended function, without causing or imparting significant negative/detrimental impact.

Uncontradicted, heading(s) (e.g., "Construction, Terms . . . ") and subheadings are included for convenience and do not limit the scope of any aspect(s). Uncontradicted, aspect(s), step(s), or element(s) described under one heading can apply to other aspect(s) or step(s)/element(s) here.

Ranges of values are used to represent each value falling within such range that are within an order of magnitude of the smallest endpoint of the range without having to explicitly write each value of the range. E.g., a recited range of 1-2 implicitly discloses each of 1.0, 1.1, 1.2, . . . 1.9, and 2.0 and 10-100 implicitly discloses each of 10, 11, 12, . . . 98, 99, and 100). Uncontradicted, all ranges include the range's endpoints, regardless of how a range is described. E.g., "between 1-5" includes 1 and 5 in addition to 2, 3, and 4 (and all numbers between such numbers within an order of magnitude of such endpoints, e.g., 1.0, 1.1, . . . 4.9, and 5.0). For the avoidance of doubt, any number within a range, regardless of the order of magnitude of the number, is covered by the range (e.g., a range of 2-20 covers 18.593).

Terms of approximation (e.g., "about," "~," or "approximately") are used (1) to refer to a set of related values or (2) where a precise value is difficult to define (e.g., due to limits of measurement). Uncontradicted, all exact values provided here simultaneously/implicitly disclose corresponding approximate values and vice versa (e.g., disclosure of "about 10" provides explicit support for the use of 10 exactly in such aspect/description). Ranges described with approximate value(s) include all values encompassed by each approximate endpoint, regardless of presentation (e.g., "about 10-20" has the same meaning as "about 10-about 20"). The scope of value(s) encompassed by an approximate term typically depends on the context of the disclosure, criticality or operability, statistical significance, understanding in the art, etc. In the absence of guidance here or in the art for an element, terms such as "about" when used in connection with an element should be interpreted as ±10% of the indicated value(s) and implicitly disclosing ±5%, ±2%, ±1%, and ±0.5%.

Lists of aspects, elements, steps, and features are sometimes employed for conciseness. Unless indicated, each member of each list should be viewed as an independent aspect. Each aspect defined by any individual member of a list can have, and often will have, nonobvious properties vis-a-vis aspects characterized by other members of the list.

Uncontradicted, the terms "a" and "an" and "the" and similar referents encompass both the singular and the plural form of the referenced element, step, or aspect. Uncontradicted, terms in the singular implicitly convey the plural and vice versa herein (in other words, disclosure of an element/step implicitly discloses corresponding use of such/similar elements/steps and vice versa). Hence, e.g., a passage regarding an aspect including X step supports a corresponding aspect including several X steps. Uncontradicted, any mixed use of a referent such as "a" in respect of one element/step or characteristic and "one or more of" with respect to another element/step or characteristic in a paragraph, sentence, aspect, or claim, does not change the meaning of such referents. Thus, for example, if a paragraph describes a composition comprising "an X" and "one or more Ys," the paragraph should be understood as providing disclosure of "one or more Xs" and "one or more Ys."

"Significant" and "significantly" mean results/characteristics that are statistically significant using ≥1 appropriate test(s)/trial(s) in the given context (e.g., p≤0.05/0.01). "Detectable" means measurably present/different using known detection tools/techniques. The acronym "DOS" (or "DoS") means "detectable(ly) or significant(ly)."

Uncontradicted, any value here that is not accompanied by a unit of measurement (e.g., a weight of 50 or a length of 20), any previously provided unit for the same element/step or the same type of element/step will apply, or, in cases where no such disclosure exists, the unit most commonly used in association with such an element/step in the art will apply.

Uncontradicted, the terms "including," "containing," "comprising," and "having" mean "including, but not limited to" or "including, without limitation." Uncontradicted, use of terms such as comprising and including regarding elements/steps means including any detectable number or amount of an element or including any detectable performance of a step/number of steps (with or without other elements/steps).

For conciseness, description of an aspect "comprising" or "including" an element, with respect to a collection/whole (e.g., a system, device, or composition), implicitly provides support for any detectable amount/number or ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the whole/collection being made up of the element, or essentially all of the whole/collection being made up of the element (i.e., that the collection consists essentially of the referenced element). Similarly, a method described as including a step with respect to an effect/outcome implicitly provides support for the referenced step providing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the effect/outcome, representing ≥~1%, ≥~5%, ≥~10%, ≥~20%, ≥~25%, ≥~33%, ≥~50%, ≥~51%, ≥~66%, ≥~75%, ≥~90%, ≥~95%, ≥~99%, or ~100% of the steps/effort performed, or both.

Explicit listing of percentages of elements/steps in connection with aspects does not limit or contradict such implicit disclosure.

Uncontradicted, terms such as "comprising" when used in connection with a step of a method provide implicit support for performing the step once, ≥2 times, or until an associated function/effect is achieved.

Uncontradicted, the term "one" means a single type, single iteration/copy/thing, of a recited element or step, or both, which will be clear from context. For example, the referent "one" used with a component of a composition can refer to one type of element (which may be present in numerous copies, as in the case of an ingredient in a composition), one unit of the element, or both. Similarly, "one" component, a "single" component, or the "only component" of a system typically means 1 type of element (which may be present in numerous copies), 1 instance/unit of the element, or both. Further, "one" step of a method typically means performing one type of action (step), one iteration of a step, or both. Uncontradicted, a disclosure of "one" element provides support for both, but uncontradicted, any claim to any "one" element means one type of such an element (e.g., a component of a composition/system).

The term "some" means ≥2 copies/instances or ≥5% of a listed collection/whole is, or is made up of, an element. Regarding methods, some means ≥5% of an effect, effort, or both, is made up of or is attributable to a step (e.g., as in "some of the method is performed by step Y") or indicates a step is performed ≥2 times (e.g., as in "step X is repeated some number of times"). "Predominately," "most," or "mostly," means detectably >50% (e.g., mostly comprises, predominately includes, etc., mean >50%) (e.g., a system that mostly includes element X is composed of >50% of element X). The term "generally" means ≥75% (e.g., generally consists of, generally associated with, generally comprises, etc., means ≥75%) (e.g., a method that generally consists of step X means that 75% of the effort or effect of the method is attributable to step X). "Substantially" or "nearly" means ≥95% (e.g., nearly all, substantially consists of, etc., mean ≥95%) (e.g., a collection that nearly entirely is made up of element X means that at least 95% of the elements in the collection are element X). Terms such as "generally free" of an element or "generally lacking" an element mean comprising ≤~25% of an element and terms such as "substantially free" of an element mean comprising ≤~5% of an element. The phrase substantially identical may be used in this and other contexts to reflect that tests that would be considered substantially identical by those of skill in the art can be acceptable for assessing/defining such an aspect. It will be appreciated that the phrase "substantially identical" in such contexts comprises the use of identical amounts, identical formulations, and identical conditions in other respects.

Uncontradicted, any aspect described with respect to an optionally present element(s)/step(s) also provides implicit support for corresponding aspect(s) in which one, some, most, generally all, nearly all, essentially all, or all of such element(s) are lacking/step(s) not performed, in respect of the relevant aspect. E.g., disclosure of a system comprising element X implicitly also supports a system lacking element X.

Uncontradicted, changes to tense or presentation of terms (e.g., using "comprises predominately" in place of "predominately comprises") do not change the meaning of the corresponding term/phrase.

Uncontradicted, all methods provided here can be performed in any suitable order regardless of presentation (e.g., a method comprising steps A, B, and C, can be performed in the order C, B, and A; B and A and C simultaneously, etc.). Uncontradicted, elements of a composition can be assembled in any suitable manner by any suitable method. In general, any methods and materials similar or equivalent to those described here can be used in the practice of embodiments. Uncontradicted, the use of ordinal numbers such as "first," "second," "third," etc. is to distinguish respective elements rather than to denote a particular order of those elements.

Uncontradicted, any elements, steps, components, or features of aspects and all variations thereof, etc., are within the scope of the invention.

Elements associated with a function can be described as "means for" performing a function in a composition/device/system or a "step for" performing a part of a method, and parts of this disclosure refer to "equivalents," which means equivalents known in the art for achieving a referenced function associated with disclosed mean(s)/step(s). However, no element of this disclosure or claim should be interpreted as limited to a "means-plus-function" construction unless such intent is clearly indicated by the use of the terms "means for" or "step for." Terms such as "configured to" or "adapted to" do not indicate "means-plus-function" interpretation, but, rather, describe element(s)/step(s) configured to, designed to, selected to, or adapted to achieve a certain performance, characteristic, property, etc. using teachings provided here or in the art.

All references (e.g., publications, patent applications, and patents) cited herein are hereby incorporated by reference as if each reference were individually and specifically indicated to be incorporated by reference and set forth in its entirety herein. Uncontradicted, any suitable principles, methods, or elements of such references (collectively "teachings") can be combined with or adapted to aspects. However, citation/incorporation of patent documents is limited to the technical disclosure thereof and does not reflect any view regarding the validity, patentability, etc., thereof. In the event of any conflict between this disclosure and the teachings of such documents, the content of this disclosure controls regarding aspects of the invention. Numerous references are cited here to concisely incorporate known information and aid skilled persons in putting aspects into practice. While efforts have been made to include the most relevant references for such purposes, readers will understand that not every aspect of every cited reference will apply to every aspect of the invention.

All original claims contained in this disclosure when filed are incorporated into this specification as if they were a part of the description.

Additional Terms, Concepts, and Acronyms

The following description of certain terms and acronyms is provided to assist readers in understanding the invention. Additional acronyms may be only provided in other parts of this disclosure and acronyms that are well known in the art may not be provided here.

Uncontradicted, any description of ingredient representation as percentage of a composition is percent weight/volume (% w/v).

Uncontradicted, the term "composition" as used herein, is interchangeable with pharmaceutical formulation, liquid composition, liquid formulation, formulation, and solution and refers to preparations comprising pilocarpine in a form suitable for ophthalmic administration to a patient or subject. At times herein, the term "formulation" is used to describe a composition wherein exemplary ranges of composition constituents are provided, and "composition" is used where specific composition constituents are provided in specific exemplary amounts.

Except where explicitly indicated or clearly indicated by context, "improved" herein means "increased." In aspects, readers will understand that "improved" means "reduced," such as with respect to the toxicity of a composition. Uncontradicted, terms such as "enhanced," "improved," and the like are used synonymously.

Terms such as "pharmaceutical suitability", "pharmaceutically suitable", "ophthalmologically suitable" or "ophthalmological suitability" are phrases typically used to refer to compositions that are safe and effective for pharmaceutical administration and application, having sufficient potency, purity, strength, quality, and safety for pharmaceutical application, in cases specifically to the eye, as may be judged by regulatory authority review, and as established by, e.g., one or more well-controlled and adequate clinical studies performed in compliance with generally prevailing regulatory authority standards. Compositions described as "ophthalmologically suitable" should be interpreted to mean suitable for ophthalmic delivery when provided in a potency, purity, strength, or quality making it safe for ophthalmic use. Components described as "ophthalmologically suitable" should be interpreted in a similar manner Uncontradicted, a description of "suitability" implicitly means that the referenced element, step, etc., is ophthalmologically/pharmaceutically suitable or otherwise medically suitable (e.g., safe and effective as determined by proper nonclinical/clinical testing).

Excipients herein are typically present in "effective amounts," and, uncontradicted, any described class of excipient or specific excipient is understood to be present in the associated composition/formulation in an effective amount, which generally means, in this context, an amount that is effective for the described function(s) associated with the excipient (it being understood that some excipient compound(s)/ingredient(s) exhibit more than one effect). E.g., a tonicity agent will be understood to be present in a composition/formulation in an amount that is effective to impart an indicated tonicity effect, a tonicity effect that is required for suitability of the composition, or an effect that imparts a significant tonicity effect on a composition (with respect to a comparator composition lacking the compound(s)/ingredient(s)).

Aspects of the invention are described broadly and generically herein, as well as in narrower species and examples. Each of the narrower species, examples, and subgeneric groupings falling within the generic disclosure also form part of the invention. This includes the generic description of the invention with a proviso or negative limitation removing one or more specific matters from the genus, regardless of whether or not the excised (specifically excluded) material is specifically recited herein.

SUMMARY OF THE INVENTION

The inventions described and claimed herein have many attributes and aspects including, but not limited to, those set forth in, e.g., described or referenced in, this Summary. This Summary of the Invention ("Summary") is not intended to be all-inclusive, and the scope of the invention is not limited to or by the aspects, features, elements, or embodiments provided in this Summary, which is included for illustrative purposes only and not restriction. Any of the aspects described under this section can be combined with any other aspect described in this section or with any other aspect of this disclosure.

In aspects, the invention provides pharmaceutically acceptable and ophthalmologically suitable reduced buffer content composition(s) in the form of a solution. In aspects, such compositions can be used in the treatment of one or more ocular condition(s) via administration to a mammalian eye. According to aspects, provided herein are reduced buffer content composition(s) comprising a therapeutically effective amount of an active pharmaceutical ingredient, in aspects a single active pharmaceutical ingredient, such as, e.g., a parasympathomimetic compound, such as, e.g., a pilocarpine compound. In aspects, a therapeutically effective amount of such an active pharmaceutical ingredient, e.g., pilocarpine compound, is an amount greater than about 1% w/v of the composition, such as, e.g., an amount which is greater than about 1.1% w/v or greater than about 1.2% w/v of the composition. In aspects, the invention provides composition(s) described in this paragraph wherein the compositions further comprise a buffer component. A buffer component of compositions herein can, in aspects, be characterized as a uniform buffering component, wherein the buffer component comprises a single buffering compound representing at least about 99% of the buffer component. In aspects, a buffer component, e.g., a uniform buffering component, is present in a concentration of compositions provided herein such that the concentration of an active pharmaceutical ingredient, e.g., a sole active pharmaceutical ingredient present in the composition, e.g., a pilocarpine compound, in the composition is at least about 1.5 times as high as the concentration of buffer component present in the composition. In aspects, a buffer component, e.g., a uniform buffering component, is present in a concentration of compositions provided herein such that the concentration of an active pharmaceutical ingredient, e.g., a sole active pharmaceutical ingredient present in the composition, e.g., a pilocarpine compound, in the composition is less than about 4 times as high as the concentration of buffering component in the composition. In aspects, the invention provides new ways of ameliorating or reducing an ophthalmic condition, e.g., presbyopia, such as or including, e.g., one or more symptoms of the ophthalmic condition such as presbyopia, for patients who do not wish to undergo surgery (intra-ocular lenses, laser ablation, etc.) or use corrective glasses, such as, e.g., by receipt of topical administration of composition(s) such as those described in this paragraph.

In aspects, the invention described herein provides pharmaceutically acceptable and ophthalmologically suitable compositions comprising pilocarpine hydrochloride for treating an ocular condition, such as or including, e.g., one or more symptoms of the ocular condition, selected from the group consisting of presbyopia, hyperopia, mydriasis, anisocoria, accommodative esotropia, myopia, and astigmatism, wherein compositions exhibit good physical and chemical stability.

In certain aspects, compositions provided by the invention provide a reduced level of irritation compared to marketed pilocarpine composition(s) comprising a plurality of buffers, high buffering capacity, no demulcent, or combination(s) thereof. In aspects, a demulcent can also provide penetration enhancement effect of one or more active pharmaceutical ingredient(s) of the composition(s), such as, e.g., pilocarpine compound(s). In some aspects, a penetration enhancer which does not provide demulcent effect is provided as a constituent of the composition(s). In certain aspects, compositions are provided as aqueous solutions. In alternative aspects, compositions are provided as a gel. In aspects, providing compositions as a gel increases the length of time that an API, e.g., pilocarpine compound, e.g., pilocarpine HCl, is retained in the eye over similar aqueous solution compositions.

In aspects, the invention provides a pharmaceutically acceptable and ophthalmologically suitable composition for treating an ocular condition such as those described in this Summary, wherein the composition maintains (a) a pH of between about 3 and about 6 and (b) at least about 97% of the pilocarpine compound when stored at about 15° C.-about 27° C. and about 60% relative humidity, when stored at about 38° C.-about 42° C. and 75% relative humidity, when stored at 25±2° C. and 40±5% relative humidity, or when stored under any one or more of the three condition(s), for a period of at least about one month, e.g., a period of at least about 3 months. In aspects, the composition maintains (a) a pH of between about 3 and about 6 and (b) at least about 97% of the pilocarpine compound when stored under conditions comprising a temperature of between about 15° C. and about 42° C. and a relative humidity of between about 35% and about 75% relative humidity for a period of at least about one month, such as, e.g., when stored for a period of at least about 3 months.

In aspects, the pilocarpine compound of the compositions of the preceding paragraphs can be a salt of pilocarpine, such as pilocarpine hydrochloride. In aspects, pilocarpine hydrochloride can be present in an amount of between about 1% w/v-about 3% w/v of the composition(s), such as about 1.25% w/v. In aspects, the ocular condition of the preceding paragraphs is selected from the group consisting of presbyopia, hyperopia, mydriasis, anisocoria, accommodative esotropia, myopia, and astigmatism. In aspects, the pH of the compositions of the preceding paragraphs is maintained within a range of about 3.5 to about 5.5. In aspects, the compositions of the preceding paragraphs are provided in the form of a solution.

In aspects, the invention provides the compositions of the preceding paragraphs wherein the composition further comprises one or more additional, or, e.g., non-buffer, excipients, such as one or more excipients selected from a penetration enhancer component, a solubilization component, a demulcent component, a tonicity component, a thickening component, a chelation component, a pH adjusting component, a preservative component, and a carrier component. In aspects, compositions provided by the invention described in preceding paragraphs can comprise a tonicity component. In aspects, compositions provided by the invention described in preceding paragraphs can comprise a preservation component, such as a preservation component comprising a quaternary ammonium salt, e.g., benzalkonium chloride. Further, in aspects, compositions provided by the invention described in preceding paragraphs can comprise a penetration enhancer component, wherein the penetration enhancer provides detectable or significant activity as a penetration enhancer, a solubilizer, and a demulcent, such as, for example polysorbate 80.

In aspects, the invention provides a pharmaceutically acceptable and ophthalmologically suitable composition for treating an ocular condition, such as, or including, one or more symptoms of an ocular condition, comprising a pilocarpine compound in an amount of about 1% w/v-about 3% w/v; a solubilization component in an amount of between about 0.1% w/v-about 0.7% w/v; a preservation component in an amount of about 0.003% w/v-about 0.02% w/v; a tonicity component in an amount of between about 3.5% w/v-about 5.5% w/v; and a viscosity enhancement component (thickening component) in an amount of about 0.1% w/v-about 1% w/v, wherein the composition maintains (a) a pH of between about 3 and about 6 and (b) at least about 97% of the pilocarpine compound when stored at about 15° C.-about 27° C. and about 60% relative humidity, when stored at about 38° C.-about 42° C. and 75% relative humidity, when stored at 25±2° C. and 40±5% relative humidity, or when stored under any one or more of the three condition(s), for at least about one month, such as, e.g. at least about 3 months. In aspects, the composition maintains (a) a pH of between about 3 and about 6 and (b) at least about 97% of the pilocarpine compound when stored under conditions comprising a temperature of between about 15° C. and about 42° C. and a relative humidity of between about 35% and about 75% relative humidity for a period of at least about one month, such as, e.g., when stored for a period of at least about 3 months. In aspects, such a composition is provided as a gel.

In aspects, the invention provides the gel composition of the preceding paragraph wherein the pilocarpine compound is a salt of pilocarpine, such as pilocarpine hydrochloride, in an amount of about 1.25% w/v. In aspects, the invention provides the gel composition described above wherein the ocular condition is selected from the group consisting of presbyopia, hyperopia, mydriasis, anisocoria, accommodative esotropia, myopia, and astigmatism. In aspects, the pH of the gel composition is maintained within a range of between about 3.5-about 5.5. In aspects, the pilocarpine compound of the gel composition is retained in the eye for a detectably or significantly longer period of time than a comparable composition providing the same amount of pilocarpine compound provided in the form of a liquid (e.g., aqueous) solution. In aspects, the composition provided in the form of a gel causes detectably or significantly less blurriness than a comparable composition providing the same amount of pilocarpine compound provided in the form of a liquid (e.g., aqueous) solution.

In aspects, the invention provides compositions according to any of the preceding paragraphs of this section, wherein the composition maintains at least about 98% of the pilocarpine compound when stored at about 15° C.-about 27° C. and about 60% relative humidity, when stored at about 38° C.-about 42° C. and 75% relative humidity, when stored at 25±2° C. and 40±5% relative humidity, or when stored under any one or more of the three condition(s), for at least about three months, such as ≥~6 months, ≥~12 months, ≥~18 months, ≥~24 months, or, e.g., ≥~36 months. In aspects, the composition maintains at least about 98% of the pilocarpine compound when stored under conditions comprising a temperature of between about 15° C. and about 42° C. and a relative humidity of between about 35% and about 75% relative humidity for a period of at least about one month, such as, e.g., when stored for a period of at least about 3 months, such as ≥~6 months, ≥~12 months, ≥~18 months, ≥~24 months, or, e.g., ≥~36 months. In aspects, the invention provides compositions according to any of the preceding paragraphs of this section, wherein the composition comprises less than about 0.5% total impurities after storage at about 15° C.-about 27° C. and about 60% relative humidity, after storage at about 38° C.-about 42° C. and 75% relative humidity, when stored at 25±2° C. and 40±5% relative humidity, or when stored under any one or more of the three condition(s), for a period of at least about 1 month, such as ≥~3 months, ≥~6 months, ≥~12 months, ≥~18 months, ≥~24 months, or, e.g., ≥~36 months. In aspects, the composition comprises less than about 0.5% total impurities when stored under conditions comprising a temperature of between about 15° C. and about 42° C. and a relative humidity of between about 35% and about 75% relative humidity for a period of at least about one month, such as, e.g., when stored for a period of at least about 3 months, such as ≥~6 months, ≥~12 months, ≥~18 months, ≥~24 months, or, e.g., ≥~36 months.

In aspects, the invention provides methods of improving vision, methods of reducing visual impairment, methods of treating an ophthalmic condition, including, e.g., one or more symptoms related to the ophthalmic condition, selected from the group consisting of presbyopia, hyperopia, mydriasis, anisocoria, accommodative esotropia, myopia, and astigmatism, or any combination of such methods, the methods comprising administering an effective amount of any one or more of the compositions described in this section, for an effective period of time to treat the target indication, e.g., for an acute or chronic treatment period. In aspects, the invention provides methods of improving vision, methods of reducing visual impairment, methods of treating an ophthalmic condition, including, e.g., one or more symptoms related to the ophthalmic condition, selected from the group consisting of presbyopia, hyperopia, mydriasis, anisocoria, accommodative esotropia, myopia, and astigmatism, or any combination of such methods, wherein the method comprises the administration of an effective amount of any one or more of the compositions described in this section, and the method(s) is/are clinically demonstrated to be as effective or detectably or significantly more effective than treatment with the product approved under U.S. Food and Drug Administration NDA Number 214028 (as of, e.g., Jan. 1, 2022) (such product being described herein as "VUITY®" for sake of convenience) for the same or similar indication (e.g., improving vision) and for at least substantially the same administration period. In aspects, the invention provides a method of treating presbyopia, including one or more symptoms related to presbyopia, wherein the method comprises administration of an effective amount of a composition described in this section, and wherein the method results in detectably or significantly reduced ocular blurring, ocular discomfort, eye pain, brow ache, blurry vision, light sensitivity, stinging, itching, or any combination of any or all thereof compared to treatment of presbyopia with the product approved under U.S. Food and Drug Administration NDA Number 214028 (VUITY®) for at least substantially the same administration period.

Finally, in aspects, the invention provides methods of manufacturing the liquid solution and gel compositions described in this section, and kits providing the compositions described in this section.

DETAILED DESCRIPTION OF THE INVENTION

For convenience, both combinations of elements/steps and individual elements/steps may be described in this section of this disclosure. Despite the inclusion of passages focused on specific elements/steps, any aspect, facet, embodiment, or other description of particular step(s) or element(s) can be applied to any general description of the compositions/methods of the invention, or any other recited element(s)/step(s) thereof, which are provided in any part of this disclosure.

As used herein, the word "exemplary" means "serving as an example, instance, or illustration." Uncontradicted, the content of the following detailed description is merely exemplary in nature and is not intended to limit application and uses. Any embodiment/aspect described herein as "exemplary" is not necessarily to be construed as preferred or advantageous over other embodiments.

Compositions

In aspects, the invention provides pharmaceutically acceptable and ophthalmologically suitable compositions comprising a parasympathomimetic compound component and one or more excipients. In aspects, compositions are reduced buffer content compositions. In aspects, compositions provided by the invention are characterizable by the amount of a buffer component relative to the amount of active pharmaceutical ingredient(s). In aspects, compositions provided by the invention comprise relative amount(s) of buffer component and active pharmaceutical ingredient(s) which is/are capable of stably maintaining the composition (e.g., maintaining an amount of API which is at least about 97% of an original amount, maintaining a level of impurity(ies) suitable for approval by a recognized regulatory body such as, e.g., the United States Food and Drug Administration), or both) for a commercially relevant period of time under typical storage conditions or conditions utilized for stability study(ies), including accelerated stability studies, known in the art. In aspects, storage conditions herein refer to conditions comprising a temperature of between about 15° C. and about 42° C. and a relative humidity of between about 35% and about 75% relative humidity. Herein, a "commercially relevant period of time" is a period of time of at least about 1 month, e.g., ≥~6 weeks, ≥~2 months, ≥~10 weeks, ≥~3 months, ≥~6 months, ≥~9 months, ≥~12 months, ≥~18 months, ≥~24 months, ≥~28 months, ≥~32 months, or ≥~36 months. In aspects, such compositions are suitable for ophthalmic administration for the treatment of one or more conditions of the eye, such as impaired vision (improving vision or reducing impaired vision) or a specific condition or symptoms related to the specific condition, such as, e.g., presbyopia. In aspects, the parasympathomimetic compound component comprises the only active pharmaceutical ingredient (API) in the composition.

Parasympathomimetic Compound Component (PCC)

In aspects, compositions provided by the invention comprise a parasympathomimetic compound component ("PCC"). In aspects, the PCC comprises one or more parasympathomimetic agents (or parasympathomimetic drug). In aspects, the term "parasympathomimetic agent or drug" used herein refers to include to any cholinergic drug that enhances the effects mediated by acetylcholine in the central nervous system, the peripheral nervous system, or both. In aspects, a "parasympathomimetic agent or drug" is a muscarinic agonist. In aspects, a "parasympathomimetic agent or drug" is a muscarinic antagonist.

In aspects, the PCC can comprise any pharmaceutically acceptable and ophthalmologically suitable parasympathomimetic agent/drug. Examples of suitable cholinergic compounds are alpha androgenic agonists such as, e.g., acetylcholine, muscarine, pilocarpine, nicotine, suxamethonium, bethanechol, carbachol, methacholine, phenylpropanolamine, amphetamine, ephedrine, phentolamine, fenfluramine, etc. In certain aspects, suitable PCC constituents are muscarinic cholinergic agonists provided in ophthalmologically suitable form, such as, e.g., bethanechol compound(s), cevimeline compound(s), pilocarpine compound(s), methacholine compound(s), and xanomeline compound(s). In certain aspects, the PCC comprises one or more pilocarpine compounds. In certain aspects, the PCC comprises only one or more pilocarpine compound(s). In certain aspects, compositions comprise a single active pharmaceutical ingredient, e.g., a pilocarpine compound.

Pilocarpine Compounds

In aspects, the PCC of compositions provided by the invention comprises one or more pilocarpine compounds (compounds that comprise pilocarpine, including derivatives thereof, or that include another compound that is a pharmaceutically acceptable analog of pilocarpine that exhibits at least similar physiological/therapeutic effects as pilocarpine). Analogs of pilocarpine are known in the art (see, e.g., U.S. Pat. No. 5,025,027) and such analogs may be suitable in compositions/methods of the invention and other such analogs can be generated by application of routine methods. However, in aspects, certain compounds or groups of compounds may offer one or more different properties, such that each such compound can be considered its own aspect or to define a category of aspects of the invention. In aspects, the PCC does not include analogs, only pilocarpine, pilocarpine derivatives (a molecule comprising a pilocarpine core and additional groups), or a related compound (e.g., a salt of either or both thereof). In aspects, a PCC only comprises pilocarpine or a related compound, such as a salt thereof.

Pilocarpine (C11H16N2O2) is a muscarinic cholinergic agonist having a molecular weight of about 208 Da having the structure provided below.

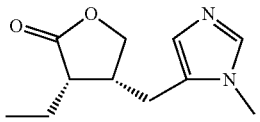

Pilocarpine

In aspects, the pilocarpine compound can be any pharmaceutically acceptable and ophthalmologically suitable pilocarpine compound, such as, e.g., any pharmaceutically acceptable salts, pharmaceutically acceptable solvates, pharmaceutically acceptable hydrates, pharmaceutically acceptable enantiomers, pharmaceutically acceptable derivatives, pharmaceutically acceptable polymorphs, and pharmaceutically acceptable prodrugs thereof. In aspects, a pilocarpine compound is limited to one or some of these types of compound(s) but excludes other type(s) of any such compounds. E.g., in aspects, a pilocarpine compound does not include a polymorph, but does include two or more salts of pilocarpine.

Examples of pilocarpine salts include, e.g., the acetate, succinate, tartrate, bitartrate, dihydrochloride, salicylate, hemisuccinate, citrate, maleate, hydrochloride, carbamate, sulfate, nitrate, and benzoate salt forms of pilocarpine, and, e.g., quaternary pilocarpine salts (see, e.g., Wojciechowski thesis, University of Illinois, 1961; doi.org/10.1002/jps.2600501012), (1)-acyloxy-alkyl-pilocarpine salts described in U.S. Pat. No. 4,061,722A, piloplex (see Ticho, et. Al. in "Piloplex, a new long-acting pilocarpine polymer salt. A long-term study," in British Journal of Ophthalmology, 1979, 63; 45-47), etc.

Pilocarpine enantiomers include, e.g., the (+)-1 and (−)-1 enantiomers of pilocarpine (see, e.g., Schmidt, Theresa et al. "Concise Synthesis of Both Enantiomers of Pilocarpine." Molecules (Basel, Switzerland) vol. 26, 12 3676. 16 Jun. 2021, doi:10.3390/molecules26123676).

Examples of pilocarpine derivatives include ophthalmologically suitable forms of quaternary pilocarpine derivatives described in, for example, Druzgala P, et. Al. in, "New water-soluble pilocarpine derivatives with enhanced and sustained muscarinic activity," Pharm Res. 1992 March; 9(3):372-7. Doi: 10.1023/a:1015847103862. PMID: 1614970; in, e.g., Ben-Bassat A A, et. Al., "Quaternary pilocarpine derivatives as potential acetylcholine antagonists. 2. Alterations in the lactone and imidazole moieties," J Med Chem. 1976 July; 19(7):928-33; and in, e.g., U.S. Pat. Nos. 5,530,136A, 4,835,174A, EP559700B1, etc. Pilocarpine derivatives also include, e.g., Pilo-OEG (Wang and Yang, described at innovationgateway.vcu.edu/technologies/biomedical/comeal-permeable-anti-glaucoma-drug) (Virginia Commonwealth University (VCU) tech number 19-080F).

Exemplary prodrugs of pilocarpine include, e.g., ophthalmologically suitable forms of various alkyl and aralkyl esters of pilocarpic acid described in, e.g., Bundgaard H, et. al. "Pilocarpine prodrugs I. Synthesis, physicochemical properties and kinetics of lactonization of pilocarpic acid esters," J Pharm Sci. 1986 January; 75(1):36-43. doi: 10.1002/jps.2600750109. PMID: 3958903; in, e.g., Bundgaard H, et. al. in "Pilocarpine prodrugs. II. Synthesis, stability, bioconversion, and physicochemical properties of sequentially labile pilocarpine acid diesters," J Pharm Sci. 1986 August; 75(8):775-83. doi: 10.1002/jps.2600750811. PMID: 3772750; in, e.g., Jarvinen, et. al. "Synthesis and identification of pilocarpic acid diesters, prodrugs of pilocarpine," 1991, Journal of Pharmaceutical and Biomedical Analysis, Vol. 9, Issue 6, pp. 457-464, DOI 10.1016/0731-7085(91)80247-7; in, e.g., EP0106541A2, etc.

Herein, uncontradicted, the term "pilocarpine" or "pilocarpine compound" refers to not only pilocarpine directly, but also its other pharmaceutically acceptable and ophthalmologically suitable salts, pharmaceutically acceptable solvates, pharmaceutically acceptable hydrates, pharmaceutically acceptable enantiomers, pharmaceutically acceptable derivatives, pharmaceutically acceptable polymorphs, and pharmaceutically acceptable prodrugs thereof such as those exemplified above. However, as noted, combinations of two or more thereof, but less than all, of such compound types; each individual compound type; and individual compounds/compositions described herein, each represent different aspects of the invention and in cases exclude some or more of such other compounds.

In certain aspects, the compositions provided by the invention comprise a pilocarpine compound which is a pharmaceutically acceptable salt of pilocarpine. In aspects, the pharmaceutically acceptable salt of pilocarpine is pilocarpine hydrochloride.

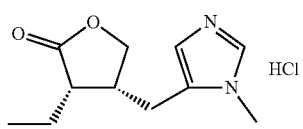

Pilocarpine Hydrochloride

In aspects, the PCC is present in compositions in a therapeutically effective amount (e.g., an effective amount).

In aspects, the PCC is present in compositions provided by the invention in an amount representing between about 0.5% w/v to about 4% w/v, such as, for example, ~0.5% w/v-~3.8% w/v, ~0.5% w/v-~3.6% w/v, ~0.5% w/v-~3.4% w/v, ~0.5% w/v-~3.2% w/v, or ~0.5% w/v-~3% w/v, such as ~0.6% w/v-~4% w/v, ~0.7% w/v-~4% w/v, ~0.8% w/v-~4% w/v, ~0.9% w/v-~4% w/v, or ~1% w/v-~4% w/v, such as for example ~0.6% w/v-~3.8% w/v, ~0.7% w/v-~3.6% w/v, ~0.8% w/v-~3.4% w/v, ~0.9% w/v-~3.2% w/v, or, e.g., ~1% w/v-~3% w/v. In aspects, compositions comprise between about 1% w/v to about 2% w/v of a PCC, such as, e.g., about 1.25% w/v of a PCC.

In certain embodiments, composition(s) comprise an amount of pilocarpine which is significantly greater than 1.5% w/v, such as, e.g., at least about 1.65% w/v, $\geq$~1.7% w/v, $\geq$~1.75% w/v, $\geq$~1.8% w/v, $\geq$~1.85% w/v, $\geq$~1.9% w/v, 1.95% w/v, or $\geq$~2% w/v, $\geq$~2.1% w/v, $\geq$~2.2% w/v, $\geq$~2.3% w/v, $\geq$~2.4% w/v, or $\geq$~2.5% w/v, such as, e.g., between about 1.65% w/v and about 3% w/v pilocarpine compound. In certain embodiments, composition(s) comprise an amount of pilocarpine which is significantly less than 1% w/v, such as, e.g., less than about 0.9% w/v, $\geq$~0.85% w/v, 0.8% w/v, $\geq$~0.75% w/v, 0.7% w/v, $\geq$~0.65% w/v, $\geq$~0.6% w/v, $\geq$~0.55% w/v, or, e.g., $\geq$~0.5% w/v, such as, e.g., between about 0.5% w/v and about 1% w/v pilocarpine compound.

In certain aspects, compositions comprise at least about 0.5% w/v pilocarpine compound, such as at least about 0.6% w/v, at least about 0.7% w/v, at least about 0.8% w/v, at least about 0.9% w/v, at least about 1% w/v, at least about 1.1% w/v, or, e.g., at least about 1.2% w/v of a pilocarpine compound, for example at least 1.2% w/v of a pilocarpine compound.

In aspects, the PCC comprises two or more PCC constituents, wherein the total amount of such constituents is represented by the concentrations/amounts provided above. In aspects, compositions comprise a PCC comprising a single PCC constituent, wherein the total amount of such single constituent is represented by the concentrations/amounts provided above. In aspects, the PCC comprises a pharmaceutically acceptable and ophthalmologically suitable pilocarpine compound, such as a pharmaceutically acceptable and ophthalmologically suitable salt of pilocarpine, e.g., pilocarpine hydrochloride (pilocarpine HCL). In aspects, the PCC comprises a single constituent which is a pharmaceutically acceptable and ophthalmologically suitable pilocarpine compound, such as a pharmaceutically acceptable and ophthalmologically suitable salt of pilocarpine, e.g., pilocarpine HCl. In aspects, the single pilocarpine compound constituent, e.g., the pharmaceutically acceptable and ophthalmologically suitable salt of pilocarpine, e.g., pilocarpine HCl is present in compositions in the above-identified amounts. In aspects, compositions comprise pilocarpine hydrochloride (HCl) at a concentration of about 1.0% w/v to 3.0% w/v, such as about 1% w/v-about 2% w/v, e.g., about 1% w/v-about 1.5% w/v, e.g., about 1.25% w/v. In aspects, 1.25% w/v pilocarpine hydrochloride (or about 12.5 mg of pilocarpine hydrochloride) is equivalent to about 1.06% w/v pilocarpine free base (or about 10.6 mg pilocarpine free base). Such a conversion can be applied elsewhere as applicable herein, as is routinely understood in the art.

Excipients

According to certain aspects, compositions provided by the invention comprise one or more excipients, which are a type of, or alternatively can be characterized as, a composition constituent/component or ingredient. In aspects, the one or more excipients can be any pharmaceutically acceptable and ophthalmologically acceptable excipients provided that the excipient(s) does/do not detectably or significantly interfere with the activity or stability of the PCC or the activity or stability of any other excipient(s).

Buffer Component (Buffer(s))

In aspects, compositions provided by the invention comprise an effective amount of a buffer component. In aspects a buffer component can be referred to as a reduced buffer content component. In aspects, the presence of a buffer component, e.g., a reduced buffer component, yields a reduced buffer content composition. Herein, reference to a buffer component should be interpreted as, in aspects, also incorporating reference to the buffer component as a reduced buffer content component. In aspects, the buffer component comprises any one or more pharmaceutically acceptable and ophthalmologically suitable buffer system(s)/constituent(s) (e.g., pharmaceutically acceptable and ophthalmologically suitable systems/compounds) which provide detectable or significant pH buffering effect, such that, e.g., the compositions maintain a pH within the pH ranges described herein for extended periods of time (e.g., a pH of between about 3 and 6) when stored under conditions comprising a temperature of between about 15° C. and about 42° C. and a relative humidity of between about 35% and about 75% relative humidity, such as when stored at about 15° C.-about 27° C. and about 60% relative humidity, when stored at about 38° C.-about 42° C. and 75% relative humidity, or when stored under either/or any such condition for a period of at least about 1 month, e.g., $\geq$~3, $\geq$~6, $\geq$~9, $\geq$~12, $\geq$~18, $\geq$~24, or, e.g., at least about 36 months. In certain aspects, compositions comprise a buffer component comprising a single buffer system (or, e.g., a single compound, providing detectable or significant buffering capacity to the composition). In certain aspects, compositions lack a buffer component.

In aspects, compositions provided by the invention comprise a buffer component characterizable as a reduced buffer content component. In aspects, "reduced buffer content", in reference to a component or a composition, refers to the presence of an amount of a buffer component which is detectably or significantly different, more specifically, is detectably or significantly less than (in terms of concentration) that of comparable reference product(s). In aspects, a reference product is a product can be a composition comprising at least mostly the same, at least generally the same, at least essentially the same, essentially the same, at least substantially the same, or the same active pharmaceutical ingredient(s) delivered by topical application. In aspects, a reference product can be a composition comprising at least mostly the same, at least generally the same, at least essentially the same, essentially the same, at least substantially the same, or the same active pharmaceutical ingredient(s) delivered by topical application, present in at least essentially the same, essentially the same, at least substantially the same, or the same amount(s). In aspects, a reference product can be a composition sharing one or more excipient(s). In aspects, a reference product can be a composition sharing one or more excipient(s) in the same amount(s). In aspects, a reference product can be a composition comprising (a) at least mostly the same, at least generally the same, at least essentially the same, essentially the same, at least substantially the same, or the same active pharmaceutical ingredient(s), (b) at least mostly the same, at least generally the same, at least essentially the same, essentially the same, at least substantially the same, or the same active pharmaceutical ingredient(s) present in at least essentially the same, essentially the same, at least substantially the same, or the same amount(s); (c) one or more of the same excipient(s); (d) one or more of the same excipient(s) in at least mostly the same, at least generally the same, at least essentially the same, essentially the same, at least substantially the same, or the same amount(s); or (e) any combination thereof, administered by topical application. In aspects, a reference composition can be a composition having demonstrated bioequivalence to any such composition(s) described herein, wherein bioequivalence is demonstrated in an appropriately conducted study acceptable by a recognized regulatory authority, such as the United States Food and Drug Administration.

In aspects, a buffer component of a composition can comprise any ophthalmologically suitable and pharmaceutically acceptable buffer which does not detectably or significantly interfere with the required functionality of any one or more other composition constituents. In aspects, exemplary constituents of a buffer component comprise, e.g., one or more buffer systems, e.g., one or more of a phosphate buffer (e.g., sodium phosphate), acetate buffer (e.g., sodium acetate), citrate buffer (e.g., sodium citrate compound, e.g., sodium citrate dihydrate), tris buffer, carbonate buffer (e g, ammonium carbonate, sodium carbonate or sodium bicarbonate), succinate buffer, maleate buffer, a borate buffer, combinations of sodium hydroxide, potassium hydroxide, hydrochloric acid, lactic acid, phosphoric acid, sulfuric acid, etc. or combinations thereof. In specific aspects, compositions provided by the invention do not comprise a borate buffer, e.g., compositions do not comprise boric acid. In other specific aspects, compositions provided by the invention do not comprise a citrate buffer, e.g., compositions do not comprise a sodium citrate compound, e.g., sodium citrate dihydrate. In yet other specific aspects, compositions provided by the invention do not comprise a citrate buffer or a borate buffer, e.g., compositions provided by the invention do not comprise boric acid or a sodium citrate compound, e.g., sodium citrate dihydrate.

In aspects, one or more constituents of the buffer component can further provide one or more additional detectable or significant functionalities, such as, for example, detectable or significant pH adjusting effects.

In aspects, compositions comprise an amount of buffer component which is detectably or significantly less than the amount of buffer component present in a reference product, such a reference product being a composition approved under the United States Food and Drug Administration NDA number 21408 (VUITY). In aspects, compositions comprise a buffer component which represents an amount which is at least about 2%, ≥~5%, ≥~10%, ≥~15%, ≥~20%, ≥~25%, ≥~30%, ≥~35%, ≥~40%, ≥~45%, ≥~50%, ≥~55%, ≥~60%, ≥~65%, ≥~70%, ≥~75%, ≥~80%, ≥~85%, ≥~90%, or, e.g., even ≥~95% less than a reference product, such as, e.g., a composition approved under U.S. FDA number 21408.

In aspects, compositions comprise a buffer component which provides detectably or significantly different buffering capacity than that of a reference product, such as, e.g., a composition approved under U.S. FDA number 21408. In aspects, compositions comprise a buffer component which provides a buffering capacity which is no more than about 95% of that of a reference product, such as a buffering capacity which is less than or equal to about 90%, ≤~85%, ≤~80%, ≤~75%, ≤~70%, ≤~65%, ≤~60%, ≤~55%, ≤~50%, ≤~45%, ≤~40%, ≤~35%, ≤~30%, ≤~25%, ≤~20%, ≤~15%, ≤~10%, or no more than, e.g., less than about 5% of the buffering capacity of a reference product. In aspects, compositions comprise a buffer component which provides a detectably or significantly reduced buffering capacity compared to the buffering capacity of a reference product, such as, e.g., a composition approved under U.S. FDA number 21408.

In aspects, compositions can comprise a buffer component having the characteristics described in any of the two preceding paragraphs wherein the characteristic is formed by a range of any of the specific cited values (e.g., a buffering capacity that is between about 30% and about 80% of a reference product). In aspects, a buffer having a pKa in a certain range (e.g., any one or more buffers or any buffer element(s)/compounds having a pKa of ~3-5, ~3-~4, or about 3) is reduced in a composition of the invention as compared to a reference product, such as a composition approved under U.S. FDA number 21408, by at least about 33%, at least about 50%, at least about 65%, ≥~75%, ≥~85%, ≥~90%, ≥~95%, or ~100%.

According to certain aspects, the invention provides a reduced buffering capacity compositions which provides statistically significantly similar stability as a reference product, such as, e.g., a marketed composition, such as, e.g., a composition approved under U.S. FDA number 21408, while concurrently providing statistically significantly similar stability to such a reference product.

In aspects, compositions comprise an effective amount of a buffer component characterizable as a "uniform" buffer component. In aspects, a uniform buffer component wherein at least about 99% of the buffer component, such as ≥~99.25%, ≥~99.5%, or ≥~99.75% (or about 100%) is composed of a single type of buffer (e.g., a single compound/constituent/agent). In aspects, a buffer component comprises a single buffer compound (single buffer constituent or single buffer agent).

In certain aspects, compositions comprise a buffer component (also referred to herein as a buffering component) in an amount such that the concentration of active pharmaceutical ingredient(s) in the composition is at least about 1.5, at least about 2, at least about 2.5, or, e.g., at least about 3 times as high as, such as is at least about 1.5 times or, e.g., is at least about 3 times higher than, the concentration of the buffer component present in the composition. In certain aspects, composition comprise a buffer/buffering component in an amount such that the concentration of active pharmaceutical ingredient(s) in the composition is at least about 3.5, at least about 4, at least about 4.5, or, e.g., is at least about 5 times as high as, e.g., is at least 5 times higher than, the concentration of the buffer component present in the composition. In certain aspects, composition comprise a buffer/buffering component in an amount such that the concentration of active pharmaceutical ingredient(s) in the composition is at least about 6, ≥~7, ≥~8, ≥~9, ≥~10, ≥~11, ≥~12, ≥~13, ≥~14, ≥~15, ≥~16, ≥~17, ≥~18, ≥~19, ≥~20, ≥~21, ≥~22, ≥~23, ≥~24, ≥~25, times as high as, e.g., is at least about 25 times higher than, the concentration of the buffer component present in the composition.

In certain aspects, composition comprise a buffer/buffering component in an amount such that the concentration of active pharmaceutical ingredient(s) in the composition is at least about 26, ≥~27, ≥~28, ≥~29, ≥~30, ≥~31, ≥~32, ≥~33, ≥~34, ≥~35, ≥~36, ≥~37, ≥~38, ≥~39, or ≥~40, time as high as, e.g., is at least about 40 times higher than, the concentration of the buffer component present in the composition.

In certain aspects, composition comprise a buffer/buffering component in an amount such that the concentration of active pharmaceutical ingredient(s) in the composition is at least about 41, ≥~42, ≥~43, ≥~44, ≥~45, ≥~46, ≥~47, ≥~48, ≥~49, or ≥~50, as times high as, e.g., is at least about 50 times higher than, the concentration of the buffer component present in the composition.

In certain aspects, composition comprise a buffer/buffering component in an amount such that the concentration of active pharmaceutical ingredient(s) in the composition is at least about 51, ≥~52, ≥~53, ≥~54, ≥~55, ≥~56, ≥~57, ≥~58, ≥~59, or ≥~60, time as high as, e.g., is at least about 60 times higher than, the concentration of the buffer component present in the composition.

In certain aspects, compositions comprise a buffer/buffering component in an amount such that the concentration of active pharmaceutical ingredient(s) in the composition is less than about 5 times more than, less than about 4 times more than, less than about 3 times more than, or, e.g., is less than about 2.5 times more than, the concentration of the buffer component present in the composition. In certain specific aspects, compositions can comprise an amount of pilocarpine which is at least about 1.5 times greater than, but no more than (e.g., less than), 4 times as high as, the amount of buffer/buffering component in the composition.

In aspects, as is stated elsewhere herein, a buffer component can be, in aspects, characterizable as a uniform buffer component. In aspects, as is stated elsewhere herein, a buffer component can characterizable as a reduced buffer content buffer component (e.g., rendering a reduced buffer content composition).

In aspects, compositions comprise a buffer component present in an amount no greater than 1% w/v of a composition, such as, e.g., in an amount no greater than about 0.95% w/v, ≤~0.9% w/v, ≤~0.85% w/v, ≤~0.8% w/v, or, e.g., ≤~0.75% w/v of a composition.

In aspects, compositions comprise a buffer component present in an amount no greater than about 0.7% w/v of a composition, such as, e.g., in an amount no greater than about 0.65% w/v, ≤~0.5% w/v, ≤~0.55% w/v, ≤~0.5% w/v, ≤~0.45% w/v, ≤~0.4% w/v, ≤~0.35% w/v, ≤~0.3% w/v, ≤~0.25% w/v, ≤~0.2% w/v, ≤~0.15% w/v, or, e.g., ≤~0.1% w/v of a composition.

In aspects, compositions comprise a buffer component present in an amount no greater than about 0.095% w/v of a composition, such as, e.g., in an amount no greater than about 0.09% w/v. ≤~0.085% w/v, ≤~0.08% w/v, ≤~0.075% w/v, ≤~0.07% w/v, ≤~0.065% w/v, ≤~0.06% w/v, ≤~0.055% w/v, ≤~0.05% w/v, ≤~0.045% w/v, ≤~0.04% w/v, ≤~0.035% w/v, or ≤~0.03% w/v, such as ≤~0.025% w/v of a composition.

In aspects, compositions provided by the invention comprise a buffer component comprising one or more buffering agents, wherein the buffer component is present in the composition in a concentration representing between about 0.005% w/v to about 1.5% w/v of the composition, such as, e.g., ~0.01% w/v-~0.5% w/v, ~0.015% w/v-~0.5% w/v, or ~0.02% w/v-~0.5% w/v, e.g., ~0.01% w/v-~0.4% w/v, ~0.01% w/v-~0.3% w/v, ~0.01% w/v-~0.2% w/v, ~0.01% w/v-~0.1% w/v, or ~0.01% w/v-~0.05% w/v or ~0.02% w/v-~0.09% w/v. In one exemplary aspect, compositions comprise sodium citrate dihydrate in an amount of between about ~0.005% w/v-~0.09%, e.g., between about 0.01% w/v to about 0.05% w/v, such as about 0.02% w/v to about 0.03% w/v, e.g., about 0.022% w/v of the composition.

According to certain aspects, composition(s) provided by the invention comprise a buffer component present in the composition in an amount representing significantly greater than 0.015% w/v of the composition(s). In aspects, composition(s) comprise a buffer component present in a concentration representing at least about 0.016% w/v, such as, e.g., an amount between about 0.017% w/v, 0.018% w/v, 0.019% w/v, 0.02% w/v, 0.021% w/v, 0.022% w/v, 0.023% w/v, 0.024% w/v, or 0.025% w/v and about 0.09% w/v. In one specific example, compositions comprise an amount of sodium citrate dihydrate which is significantly greater than 0015% w/v.

In aspects, compositions provided by the invention comprise a buffer component comprising one or more buffering agents, wherein the buffer component is present in the composition in a concentration representing between about 0.01% w/v to about 1.5% w/v of the composition, such as, e.g., ~0.5% w/v-~5% w/v, ~0.6% w/v-~5% w/v, ~0.7% w/v-~5% w/v, ~0.8% w/v-~5% w/v, ~0.9% w/v-~5% w/v, or ~1% w/v-~5% w/v, e.g., ~0.5% w/v-~4.5% w/v, ~0.5% w/v-~4% w/v, ~0.5% w/v-~3.5% w/v, ~0.5% w/v-~3% w/v, ~0.5% w/v-~2.5% w/v, ~0.5% w/v-~2% w/v, ~0.5% w/v-~1.5% w/v, or ~0.5% w/v-~1% w/v. In one exemplary aspect, compositions comprise boric acid in an amount of between about 0.5% w/v-about 1.5% w/v, such as between ~0.75% w/v-~1.25% w/v, e.g., about 1% w/v of the composition.

In certain specific aspects, compositions comprise a buffer component comprising a single buffer system, e.g., a single buffer compound/constituent. That is, in certain specific aspects, no more than a single buffer constituent is present in the compositions. In aspects, such a single buffer constituent can be any single buffer constituent described herein, such as boric acid, sodium citrate dihydrate, an acetate buffer, a phosphate buffer, etc. In aspects, such single buffer component constituents can be present in the amounts described herein. In aspects, compositions do not comprise a buffer component. In aspects, compositions provided by the invention do not comprise any constituent characterizable as a buffer.

According to certain aspects, compositions can comprise a buffer component wherein the buffer component is a uniform buffer component, and the at least primary (e.g., representing at least 99% of the buffer component) buffer compound present in the buffer component has a pKa of less than about 5, such as, less than, e.g., no greater than, about 4.9, ≤~4.8, ≤~4.7, ≤~4.6, ≤~4.5, ≤~4.4, ≤~4.3, ≤~4.2, or ≤~4.1.

In other aspects, compositions can comprise a buffer component wherein the buffer component is a uniform buffer component, and the at least primary buffer compound present in the buffer component has a pKa of less than, e.g., no greater than, about 4, such as less than about 3.9, ≤~3.8, ≤~3.7, ≤~3.6, ≤~3.5, ≤~3.4, ≤~3.3, ≤~3.2, or, e.g., ≤~3.1.

In still other aspects, compositions can comprise a buffer component wherein the buffer component is a uniform buffer component, and the at least primary buffer compound present in the buffer component has a pKa of at least about 7.5, such as at least about 7.6, ≥~7.7, ≥~7.8, ≥~7.9, or ≥~8, such as at least about 8.1, ≥~8.2, ≥~8.3, ≥~8.4, ≥~8.5, ≥~8.6, ≥~8.7, ≥~8.8, or, e.g., ≥~8.9.

In still other aspects, compositions can comprise a buffer component wherein the buffer component is a uniform buffer component, and the at least primary buffer compound present in the buffer component has a pKa of at least about 9, such as at least about 9.1, ≥~9.2, ≥~9.3, ≥~9.4, or, e.g., ≥~9.5.

In certain aspects, compositions can comprise a buffer component wherein the buffer component is a uniform buffer component, and the at least primary buffer compound present in the buffer component is a compound having at least two different ionizable functional groups, such as, e.g., 2 or 3 or more ionizable functional groups. In aspects, compositions comprise a buffer component, e.g., a uniform buffer component, comprising a compound having three different ionizable functional groups. In aspects, a compound having multiple ionizable functional groups can comprise pKa values of between about zero and about 12.

In aspects, a buffer compound of a buffer component, or, e.g., a compound having multiple ionizable functional groups, can comprise at least one pKa value of less than zero; between about 1 and about 3; about 3 and about 5; about 3 and about 8; about 8 and about 13; about 14 or higher; or, e.g., combinations of any or all thereof.

In aspects, a buffer compound of a buffer component, or, e.g., a compound having multiple ionizable functional groups, can comprise at least one pKa value of less than zero.

In aspects, a buffer compound of a buffer component, or, e.g., a compound having multiple ionizable functional groups, can comprise at least one pKa value of ~0-~12, ~0-~11, ~0-~10, ~0-9, ~0-8, ~0-7, ~0-6, ~0-5, ~0-4, ~0-3, ~0-2, or, e.g., ~0-~1.

In aspects, a buffer compound of a buffer component, or, e.g., a compound having multiple ionizable functional groups, can comprise at least one pKa value of ~1-~12, ~1-~11, ~1-~10, ~1-~9, ~1-~8, ~1-~7, ~1-~6, ~1-~5, ~1-~4, ~1-~3, or, e.g., ~1-~2.

In aspects, a buffer compound of a buffer component, or, e.g., a compound having multiple ionizable functional groups, can comprise at least one pKa value of ~2-~12, ~2-~11, ~2-~10, ~2-~9, ~2-~8, ~2-~7, ~2-~6, ~2-~5, ~2-~4, or, e.g., 2-~3.

In aspects, a buffer compound of a buffer component, or, e.g., a compound having multiple ionizable functional groups, can comprise at least one pKa value of ~3-~12, ~3-~11, ~3-~10, ~3-~9, ~3-~8, ~3-~7, ~3-~6, ~3-~5, or, e.g., 3-~4.

In aspects, a buffer compound of a buffer component, or, e.g., a compound having multiple ionizable functional groups, can comprise at least one pKa value of ~4-~12, ~4-~11, ~4-~10, ~4-~9, ~4-~8, ~4-~7, ~4-~6, or, e.g., 4-~5.

In aspects, a buffer compound of a buffer component, or, e.g., a compound having multiple ionizable functional groups, can comprise at least one pKa value of ~5-~12, ~5-~11, ~5-~10, ~5-~9, ~5-~8, ~5-~7, or, e.g., 5-~6.

In aspects, a buffer compound of a buffer component, or, e.g., a compound having multiple ionizable functional groups, can comprise at least one pKa value of ~6-~12, ~6-~11, ~6-~10, ~6-~9, ~6-~8, or, e.g., 6-~7.

In aspects, a buffer compound of a buffer component, or, e.g., a compound having multiple ionizable functional groups, can comprise at least one pKa value of ~7-~12, ~7-~11, ~7-~10, ~7-~9, or, e.g., 7-~8.

In aspects, a buffer compound of a buffer component, or, e.g., a compound having multiple ionizable functional groups, can comprise at least one pKa value of ~8-~12, ~8-~11, ~8-~10, or, e.g., 8-~9.

In aspects, a buffer compound of a buffer component, or, e.g., a compound having multiple ionizable functional groups, can comprise at least one pKa value of ~9-~12, ~9-~11, or, e.g., 9-~10.

In aspects, a buffer compound of a buffer component, or, e.g., a compound having multiple ionizable functional groups, can comprise at least one pKa value of ~10-~12, or, e.g., ~10-~11.

In aspects, a buffer compound of a buffer component, or, e.g., a compound having multiple ionizable functional groups, can comprise at least one pKa value of ~11-~12.

In aspects, a buffer compound of a buffer component, or, e.g., a compound having multiple ionizable functional groups, can comprise at least one pKa value of greater than 12.

In aspects, compositions of the invention are characterized by having a single buffer compound/element/agent having a PKa as indicated in any of the preceding ~20 paragraphs relating to pKa characteristics. In aspects, compositions exclude (are free of) buffering compounds having different pKa characteristics from a single buffering agent in the composition (e.g., in aspects the compositions comprising only a buffering agent with a PKa of ~8-9 or ~3 or ~4.5).

In one aspect, compositions comprise a buffer component, wherein the buffer component does not comprise a borate buffer (e.g., does not comprise boric acid) and, further, does not comprise a citrate buffer (e.g., does not comprise sodium citrate, e.g., does not comprise sodium citrate dihydrate). In aspects, such a buffer component which does not comprise a borate or citrate buffer can comprise one or more other buffer component constituents, such as, for example, an acetate buffer, a phosphate buffer, or both, in an amount described in this section (in aspects, e.g., wherein such an amount may be herein described as, e.g., an amount associated with a citrate compound, a borate compound, or both). In aspects, such a buffer component which does not comprise a borate or a citrate buffer can comprise a buffer component comprising a single buffer system (e.g., single buffer component constituent), such as an acetate buffer or a phosphate buffer. In aspects, compositions comprise a buffer component, wherein the buffer component comprises a single buffer component constituent, and further wherein the single buffer component constituent is not a borate buffer or a citrate buffer, in an amount described in this section. In aspects, the single buffer constituent is an acetate buffer. In aspects, the single buffer constituent is an acetate buffer in an amount described in this section. In aspects, compositions comprise a single buffer system present in the composition in an amount of between about 0.5% w/v and about 1.5% w/v. In aspects, compositions comprise a single buffer system present in the composition in an amount described in this section.

In this and any other ingredient aspect of the invention, the invention also can be characterized as comprising a "means" for providing a recited function, here imparting/providing an effective, detectable, or significant pH buffering effect. In such a respect, any known equivalents of such named agents can also be, e.g., are, incorporated into compositions or methods of the invention. As with other sections similarly described herein, any of the components of the invention can be, where suitable, described as means (e.g., the above-described buffering agents/compounds or components can be described as buffering means/buffer means or means for providing effective, detectable, or significant pH buffering activity/characteristics to the composition.)

Penetration Enhancer Component (Penetration Enhancer(s))

In certain aspects, compositions provided by the invention comprise a penetration enhancer component (a part of the composition that comprises one or more penetration enhancer(s) in effective amounts for detectably or significantly enhancing penetration of other constituents, such as the PCC or compound(s) thereof). In aspects, a penetration enhancer component comprises any one or more pharmaceutically acceptable and ophthalmologically suitable penetration enhancer(s) (which can be referred to as penetration agents or penetration enhancing agents/constituents), which provide detectable or significant penetration enhancement effect of any one or more constituents of the PCC. In aspects, the penetration enhancer component (e.g., constituents of the penetration enhancer component) is any pharmaceutically acceptable and ophthalmologically suitable compound capable of (when present in a suitable amount and under suitable conditions) detectably or significantly increasing the amount of a PCC constituent, e.g., a pilocarpine compound, such as a salt of pilocarpine, e.g., pilocarpine HCl, which penetrates eye tissue in a given period of time (e.g., the period of time between doses, such as within a 24-hour period). In aspects, the penetration enhancer component or constituent(s) thereof is/are pharmaceutically acceptable and ophthalmologically suitable compound(s) which detectably or significantly increase the amount of a PCC constituent (e.g., pilocarpine HCl) penetrating eye tissue within a 24-hour, 22-hour, 20-hour, 18-hour, 16-hour, 14-hour, 12-hour, 10-hour, 8-hour, 6-hour, 4-hour, 2-hour, or 1-hour period of time, such that a detectably or significantly greater amount of the PCC constituent(s) (e.g., pilocarpine HCl) is available within the eye tissue for treating the condition of the eye to which the treatment is directed. In aspects, the presence of a penetration enhancer component detectably or significantly increases the amount of a PCC constituent (e.g., pilocarpine HCl) which penetrates eye tissue over the amount of the same PCC constituent present in the same amount in a comparable composition lacking the penetration enhancer component.

In aspects, the penetration enhancer component or constituent(s) of the penetration enhancer component is or are any pharmaceutically acceptable and ophthalmologically suitable compound(s) capable of detectably or significantly increasing the rate of penetration into an eye tissue of a PCC constituent, e.g., a pilocarpine compound, such as a salt of pilocarpine, e.g., pilocarpine HCl. In aspects, a constituent of the penetration enhancer component detectably or significantly increases the amount of a PCC constituent penetrating eye tissue per unit time compared to the amount per unit time of the same PCC constituent present in the same amount in a comparable composition lacking the penetration component.

In aspects, a penetration enhancer component constituent is a compound or composition capable of detectably or significantly enhancing penetration of an active pharmaceutical ingredient, e.g., a PCC constituent, e.g., a pilocarpine compound, e.g., a salt of pilocarpine, e.g., pilocarpine HCl, in mammalian eye tissue (e.g., in human eye tissue, such as in the tissue of human patients). In some respects, a penetration enhancer component constituent can be any ophthalmologically suitable compound or mixture of compounds capable of exerting the effect of increasing the speed of penetration of an API present in the formulation (e.g., a pilocarpine compound) into ocular cells, e.g., corneal cells, or improving (e.g., increasing) the uptake or retention of an API present in the formulation (e.g., a pilocarpine compound) into ocular tissue or ocular cells. In aspects, a penetration enhancer detectably or significantly enhances penetration of an API, e.g., a pilocarpine compound, e.g., pilocarpine HCl, into ocular tissue by at least about 10%, at least about 20%, at least about 30%, at least about 40%, at least about 50%, at least about 60%, at least about 70%, at least about 80%, at least about 90%, or by at least about 100%, such as at least approximately 120%, at least approximately 140%, at least approximately 160%, at least approximately 180%, or at least approximately 200% or even more, over similar formulations lacking such a penetration enhancer.

In aspects, a penetration enhancer component of a composition can comprise any ophthalmologically suitable and pharmaceutically acceptable penetration enhancing agent which does not detectably or significantly interfere with the required functionality of any one or more other composition constituents. In aspects, the penetration enhancer component can comprise, most comprise, generally consist of, substantially consist of, consist essentially of, or consist of a non-ionic penetration enhancer constituent (e.g., polysorbate 80). In aspects, the only agent/compound capable of detectably or significantly enhancing the speed of (e.g., rate of) penetration of API(s) into ocular tissue, the amount of API(s) having penetrated ocular tissue after a given time period, or, both, present in composition(s) provided by the invention is polysorbate 80.

In aspects, exemplary constituents of a penetration enhancer component comprise, at least generally consist of, at least substantially consist of, at least essentially consist of, primarily consists of, or, e.g., consists of, e.g., one or more of pharmaceutically acceptable and ophthalmologically suitable polyoxyethylene sorbitan fatty acid esters, tocopheryl polyethylene glycol succinate (TPGS), poly-arginine, polyserine, tromethamine (tris), sesame seed oil or oils having similar compositions and functional characteristics suitable for ophthalmic use, etc. Exemplary polyoxyethylene sorbitan fatty acid esters include but not limited to polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65). In some aspects the polyoxyethylene sorbitan fatty acid ester can be a polyoxyethylene sorbitan oleate/polyoxyethylene sorbitan mono-oleate ester (e.g., polysorbate 80).

In aspects, additional compounds suitable for use in the present invention for increasing the penetration of an API of the composition within ocular tissue also can include quaternary ammonium compounds, such as, e.g., an ophthalmologically suitable quaternary ammonium salt. Quaternary ammonium compounds include ammonium salts in which organic radicals have been substituted for all four hydrogens of the original ammonium cation. Such compounds typically have a structure comprising a central nitrogen atom which is joined to four organic radicals and one acid radical. The organic radicals may be alkyl, aryl, or aralkyl, and the nitrogen can be part of a ring system. Examples of such compounds include benzalkonium chloride (e.g., CAS RN: 8001-54-5); benzethonium chloride CAS 121-54-0; cetalkonium chloride (e.g., CAS 122-18-9); cetrimide (e.g., CAS 8044-71-1); cetrimonium bromide (e.g., CAS 57-09-0); cetylpyridinium chloride (e.g., CAS 123-03-5); and stearalkonium chloride (e.g., CAS 122-19-0), provided that typically the quaternary ammonium compound included in any composition provided herein is of a nature and amount that is ophthalmologically safe.

In aspects, a penetration enhancer component can comprise benzalkonium chloride, benzethonium chloride, benzyltrimethylammonium chloride (also known as Triton B or trimethylbenzylammonium hydroxide), or lauryltrimethylammonium chloride (also known as dodecyltrimethylammonium chloride). In some embodiments, the ophthalmic formulations of the invention lack any quaternary ammonium salt. In aspects, the only agent/compound capable of detectably or significantly enhancing the speed of (e.g., rate of) penetration of API(s) into ocular tissue, the amount of API(s) having penetrated ocular tissue after a given time period, or, both, present in composition(s) provided by the invention is a quaternary ammonium salt, e.g., benzalkonium chloride. In aspects, the only agent(s)/compound(s) capable of detectably or significantly enhancing the speed of (e.g., rate of) penetration of API(s) into ocular tissue, the amount of API(s) having penetrated ocular tissue after a given time period, or, both, present in composition(s) provided by the invention is a quaternary ammonium salt, e.g., benzalkonium chloride, polysorbate 80, or both a quaternary ammonium salt, e.g., benzalkonium chloride, and polysorbate 80 are present.

In some aspects, formulations described herein also or alternatively comprise polyoxyl n castor oils (n=35-40) and polyoxyl hydrogenated castor oils, such as for example polyoxyl 35 castor oil (e.g., Cremophor EL), polyoxyl 40 castor oil (e.g., Marlowet 40, Emulgin RO 40), a polyoxyethylene hydrogenated castor oil (such as, e.g., polyoxyethylene hydrogenated castor oil 10/polyoxyl 10 hydrogenated castor oil, polyoxyethylene hydrogenated castor oil 40/polyoxyl 40 hydrogenated castor oil (Cremophor RH 40), polyoxyethylene hydrogenated castor oil 50/polyoxyl 50 hydrogenated castor oil, and polyoxyethylene hydrogenated castor oil 60/polyoxyl 60 hydrogenated castor oil (Cremophor RH 60)). In aspects, one suitable polyoxyl castor oil is polyoxyl-35-castor oil. In certain aspects, composition(s) lack a polyoxyl castor oil. In certain aspects, composition(s) lack polyoxyl-35-castor oil. In aspects, the only agent/compound capable of detectably or significantly enhancing the speed of (e.g., rate of) penetration of API(s) into ocular tissue, the amount of API(s) having penetrated ocular tissue after a given time period, or, both, present in composition(s) provided by the invention is a polyoxyl castor oil, e.g., polyoxyl-35-castor oil. In aspects, the only agent(s)/compound(s) capable of detectably or significantly enhancing the speed of (e.g., rate of) penetration of API(s) into ocular tissue, the amount of API(s) having penetrated ocular tissue after a given time period, or, both, present in composition(s) provided by the invention is a quaternary ammonium salt, e.g., benzalkonium chloride, polysorbate 80, a polyoxyl castor oil, e.g., polyoxyl-35-castor oil, or a combination of two or more of a quaternary ammonium salt, e.g., benzalkonium chloride, polysorbate 80, and, e.g., a polyoxyl castor oil, e.g., polyoxyl-35-castor oil, are present.

In aspects, a penetration enhancer component can comprise, e.g., a polyoxyethylene polyoxypropylene glycol, e.g., a polyoxyethylene (160) polyoxypropylene (30) glycol (Pluronic F68), a polyoxyethylene (42) polyoxypropylene (67) glycol (Pluronic P123), a polyoxyethylene (54) polyoxypropylene (39) glycol (Pluronic P85); a polyoxyethylene (196) polyoxypropylene (67) glycol (Pluronic F127) and a polyoxyethylene (20) polyoxypropylene (20) glycol (Pluronic L-44); or a polyethyleneglycol fatty acid ester, such as mono-lauric acid polyethyleneglycol, monostearin acid ethylene glycol, monostearin acid polyethyleneglycol, the mono-oleic acid polyethyleneglycol, monostearin acid ethylene glycol, an ethylene glycol distearate, the distearic acid polyethyleneglycol, and diiso stearic-acid polyethyleneglycol. In aspects, a suitable compound is polyoxyl 40 stearate. In other aspects, a penetration enhancer component can comprise tyloxapol. In further aspects, poloxamers (block copolymers) of certain examples above, such as a polyoxyethylene-polyoxypropylene block copolymer (e.g., Pluronic F-68 from BASF) and polaxamines (copolymers of three long chains of ethylene oxide and a single chain of propylene oxide that are used as nonionic surfactants) are compounds suitable for penetration enhancer components of compositions herein. In aspects, composition(s) lack one or more of a polyoxyethylene polyoxypropylene glycol, e.g., a polyoxyethylene (160) polyoxypropylene (30) glycol (Pluronic F68), a polyoxyethylene (42) polyoxypropylene (67) glycol (Pluronic P123), a polyoxyethylene (54) polyoxypropylene (39) glycol (Pluronic P85); a polyoxyethylene (196) polyoxypropylene (67) glycol (Pluronic F127) and a polyoxyethylene (20) polyoxypropylene (20) glycol (Pluronic L-44). In aspects, composition(s) lack one or more of a polyethyleneglycol fatty acid ester, such as mono-lauric acid polyethyleneglycol, monostearin acid ethylene glycol, monostearin acid polyethyleneglycol, the mono-oleic acid polyethyleneglycol, monostearin acid ethylene glycol, an ethylene glycol distearate, the distearic acid polyethyleneglycol, and diiso stearic-acid polyethyleneglycol. In aspects, composition(s) lack one polyoxyl 40 stearate, tyloxapol, poloxamers (block copolymers) of certain examples above/herein, such as, e.g., a polyoxyethylene-polyoxypropylene block copolymer (e.g., Pluronic F-68 from BASF) and polaxamines (copolymers of three long chains of ethylene oxide and a single chain of propylene oxide), or combinations of two or more thereof. In certain aspects, compositions comprise at least one polymer. In aspects, compositions lack a polymer. In aspects, the only agent(s)/compound(s) capable of detectably or significantly enhancing the speed of (e.g., rate of) penetration of API(s) into ocular tissue, the amount of API(s) having penetrated ocular tissue after a given time period, or, both, present in composition(s) provided by the invention is one or more compound(s) provided in this paragraph, a quaternary ammonium salt, e.g., benzalkonium chloride, polysorbate 80, a polyoxyl castor oil, polyoxyl-35-castor oil, or a combination of two or more thereof are present.

As noted above, any ingredient/constituent/excipient described herein typically is present in an effective amount (an amount that alone or in combination with other present agents provides a measurable or significant desired effect, such as penetration enhancement). Any ingredient/constituent described here with respect a component/composition comprising that ingredient/component, again, provides implicit support for corresponding aspects in which the described component mostly comprises, generally consists of, substantially consists of, consists essentially of, or consists only of the recited constituent, type of constituent, etc.

In aspects, compositions provided by the invention comprise a penetration enhancer component comprising one or more penetration enhancing agents, wherein the penetration enhancer component is present in the composition in a concentration representing between about 0.05% w/v to about 5% w/v of the composition, such as, e.g., ~0.1% w/v-~5% w/v, ~0.15% w/v-~5% w/v, ~0.2% w/v-~5% w/v, or ~0.25% w/v-~5% w/v, such as ~0.05% w/v-~5% w/v, ~0.05% w/v-~4.5% w/v, ~0.05% w/v-~4% w/v, ~0.05% w/v-~3.5% w/v, ~0.05% w/v-~3% w/v, ~0.05% w/v-~2.5% w/v, ~0.05% w/v-~2% w/v, ~0.05% w/v-~1.5% w/v, or ~0.05% w/v-~1% w/v, such as ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v of the composition.

In aspects, compositions provided by the invention comprise a penetration enhancer component comprising one or more penetration enhancing agents, wherein the penetration enhancer component is present in the composition in a concentration representing between about 0.005% w/v to about 0.01% w/v of the composition, such as, e.g., ~0.005% w/v-~0.009% w/v, or ~0.005% w/v-~0.008% w/v, such as, e.g., ~0.006% w/v-~0.01% w/v or ~0.007% w/v-~0.01% w/v, as in, e.g., between ~0.006% w/v-~0.009% w/v or ~0.007% w/v-~0.008% w/v of the composition.

In certain aspects, the penetration enhancer component comprises two or more constituents wherein the total concentration/amount of the two or more penetration enhancer component constituents is represented by the concentrations/amounts provided above. For example, in some aspects, compositions comprise a penetration enhancer component comprising polysorbate 80 present in an amount representing ~0.05% w/v-~5% w/v, ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v of the composition, and benzalkonium chloride in an amount representing between about 0.005% w/v to about 0.01% w/v of the composition, such as, e.g., between ~0.006% w/v-~0.009% w/v or ~0.007% w/v-~0.008% w/v of the composition. In aspects, compositions can comprise a penetration enhancer component comprising two or more constituents, such as, e.g., polysorbate 80 and benzalkonium chloride, wherein the penetration component represents between about 0.05% w/v to about 0.5% w/v, such as, e.g., between about 0.1% w/v to about 0.3% w/v of a composition. This principle can be applied to combinations of any of the specific penetration enhancers described herein, any combination of classes of penetration enhancers, or any mixture thereof, and can include three or more of such compounds/classes of compounds.

According to some aspects, composition(s) comprise a penetration enhancement agent, e.g., a quaternary ammonium salt, e.g., benzalkonium chloride (which, e.g., may provide one or more additional functional activity(ies) described herein), in an amount which is detectably or significantly less than 0.1% w/v; that is, an amount which is not equal to or greater than 0.1% w/v, such as, e.g., an amount which less than or equal to 0.095% w/v, ≤0.09% w/v, ≤0.085% w/v, ≤0.08% w/v, ≤0.075% w/v, ≤0.07% w/v, ≤0.065% w/v, ≤0.06% w/v, ≤0.055% w/v, ≤0.05% w/v, ≤0.045% w/v, ≤0.04% w/v, ≤0.035% w/v, ≤0.03% w/v, ≤0.025% w/v, or, e.g., ≤0.02% w/v. In aspects, composition(s) comprise a penetration enhancement agent, e.g., a quaternary ammonium salt, e.g., benzalkonium chloride (which, e.g., may provide one or more additional functional activity(ies) described herein), in an amount which is less than or equal to 0.02% w/v, such as, e.g., ≤0.015% w/v, ≤0.01% w/v, ≤0.009% w/v, ≤0.008% w/v, ≤0.007% w/v, ≤0.006% w/v, ≤0.005% w/v, ≤0.004% w/v, or ≤0.003% w/v. In certain aspects, compositions comprise an amount of benzalkonium chloride which is significantly less than about 0.0075% w/v. In other aspects, composition(s) comprise an amount of benzalkonium chloride which is significantly greater than about 0.0075% w/v.

In aspects, the penetration enhancer component comprises/consists essentially of/consists of a single constituent wherein the single constituent is present in an amount represented by the concentrations/amounts provided above. In aspects, the penetration enhancer component comprises/ consist essentially of/consists of at least two constituents, wherein the at least two constituents are present in composition(s) in a total amount represented by the concentrations/ amounts provided above. In aspects, composition(s) lack a penetration enhancer component.

In certain aspects, the penetration enhancer component comprises/consists essentially of (and, of course, by implication, alternatively consists of) two or more polyoxyethylene sorbitan fatty acid esters wherein the total amount of the two or more polyoxyethylene sorbitan fatty acid esters is represented by the concentrations/amounts above.

In aspects, the penetration enhancer component comprises/consists essentially of a single polyoxyethylene sorbitan fatty acid ester, wherein the total amount of the single polyoxyethylene sorbitan fatty acid ester is represented by the concentrations/amounts provided above. In certain aspects, the penetration enhancer component comprises a single constituent, the single constituent being a polyoxyethylene sorbitan fatty acid ester, such as, e.g., polysorbate 80, wherein the single polyoxyethylene sorbitan fatty acid ester, e.g., polysorbate 80, is present in an amount representing ~0.05% w/v-~5% w/v, ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v of the composition.

In aspects, a single constituent of the penetration enhancer component is/consists essentially of polysorbate 80. In certain alternative aspects, the penetration enhancer component comprises a single constituent, wherein the single constituent is a quaternary ammonium compound, e.g., a quaternary ammonium salt, e.g., benzalkonium chloride, present in an amount representing between about 0.005% w/v to about 0.01% w/v of the composition, such as, e.g., between ~0.006% w/v-~0.009% w/v or ~0.007% w/v-~0.008% w/v of the composition.

In aspects, one or more constituents of the penetration enhancer component can further provide one or more additional detectable or significant functionalities to a formulation/composition, such as, for example, a detectable or significant solubilization effect (such as is described elsewhere herein), detectable or significant demulcent effect, detectable or significant preservation effect, or any combination thereof. In aspects, one or more constituents of the penetration enhancer component can further provide preservation effect. In one aspect, a penetration enhancing agent of the penetration enhancer component also provides detectable or significant solubilization effect. In one aspect, a penetration enhancing agent of the penetration enhancer component also provides detectable or significant demulcent effect. In one aspect, a penetration enhancing agent of the penetration enhancer component also provides both detectable or significant solubilization enhancement effect and detectable or significant demulcent effect. In one aspect, a penetration enhancing agent of the penetration enhancer component also provides detectable or significant preservation effect and detectable or significant solubilization effect. In certain aspects, a penetration enhancing agent of the penetration enhancer component does not provide a solubilization effect, does not provide a preservation effect, does not provide a demulcent effect, or does not provide any combination of such additional effects. That is, in aspects, a penetration enhancer and a solubilizing agent, or a penetration enhancer and a demulcent, or, e.g., a penetration agent and a preservation agent can be differing compounds.

In this and any other ingredient aspect of the invention, the invention also can be characterized as comprising a "means" for providing a recited function, here imparting/ providing an effective, detectable, or significant penetration effect to one or more constituents of composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described penetration enhancement agents/compounds or components can be described as penetration enhancer means (or penetration means) or means for providing effective, detectable, or significant penetration activity/characteristics to one or more constituents of the composition.)

Solubilization Component (Solubilizing Agent(s))

In aspects, compositions provided by the invention comprise a solubilization component. In aspects, the solubilization component comprises any one or more pharmaceutically acceptable and ophthalmologically suitable constituents (e.g., pharmaceutically acceptable and ophthalmologically suitable compounds) which detectably or significantly increase the solubilization of one or more other constituents of the composition, detectably or significantly increase the period of time that one or more other constituents of the composition remain solubilized, or both. In aspects, the solubilization component can comprise any one or more pharmaceutically acceptable or ophthalmologically suitable compounds capable of demonstrating such an effect. In aspects, a solubilizing agent of a solubilization component can be a surfactant, e.g., demonstrating detectable or significant surfactant properties/functions, e.g., in the context of the associated composition/formulation. In aspects, a solubilization component of a composition (e.g., a surfactant) can comprise any ophthalmologically suitable and pharmaceutically acceptable solubilizing agent (or, e.g., surfactant) which does not detectably or significantly interfere with the required functionality of any one or more other composition constituents.

In aspects, one or more constituents of the solubilization component can further provide one or more additional detectable or significant functionalities, such as, for example, detectable or significant penetration enhancement effect (such as is described elsewhere herein), detectable or significant demulcent effect, or both. That is, in one aspect, a solubilizing agent of the solubilizing component also provides detectable or significant penetration enhancement effect. In one aspect, a solubilizing agent of the solubilizing component also provides detectable or significant demulcent effect. In one aspect, a solubilizing agent of the solubilizing component also provides both detectable or significant penetration enhancement effect and detectable or significant demulcent effect. In certain aspects, a solubilizing agent of the solubilizing component does not provide either a penetration enhancement effect or a demulcent effect. That is, in aspects, a penetration enhancer and a solubilizing agent, or a penetration enhancer and a demulcent, can be differing compounds.

In aspects, exemplary constituents of a solubilization component comprise, e.g., one or more of pharmaceutically acceptable and ophthalmologically suitable polyoxyethylene sorbitan fatty acid esters, tocopheryl polyethylene glycol succinate (TPGS), poly-arginine, polyserine, tromethamine (tris), sesame seed oil or oils having similar compositions and functional characteristics suitable for ophthalmic use, etc. Exemplary polyoxyethylene sorbitan fatty acid esters include but not limited to polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65). In some aspects the polyoxyethylene sorbitan fatty acid ester can be a polyoxyethylene sorbitan oleate/polyoxyethylene sorbitan mono-oleate ester (e.g., polysorbate 80). In certain aspects, constituents of a solubilization component can comprise, e.g., one or more polyethyoxylated castor oils, such as, e.g., polyethyoxylated castor oils characterizable as cremophor(s).

In aspects, one or more compounds provided in the section entitled "Penetration Enhancer Component (Penetration Enhancer(s))" also have solubilization properties, and, thus, may be considered a constituent of a solubilization component.

In aspects, compositions provided by the invention comprise a solubilization component comprising one or more solubilizing agents, wherein the solubilization component is present in the composition in a concentration representing between about 0.05% w/v to about 5% w/v of the composition, such as, e.g., ~0.1% w/v–~5% w/v, ~0.15% w/v–~5% w/v, ~0.2% w/v–~5% w/v, or ~0.25% w/v–~5% w/v, such as ~0.05% w/v–~5% w/v, ~0.05% w/v–~4.5% w/v, ~0.05% w/v–~4% w/v, ~0.05% w/v–~3.5% w/v, ~0.05% w/v–~3% w/v, ~0.05% w/v–~2.5% w/v, ~0.05% w/v–~2% w/v, ~0.05% w/v–~1.5% w/v, or ~0.05% w/v–~1% w/v, such as ~0.1% w/v–~4% w/v, ~0.15% w/v–~3% w/v, ~0.2% w/v–~2% w/v, ~0.2% w/v–~1% w/v, or ~0.2% w/v–~0.5% w/v, such as for example about 0.25% w/v of the composition.

In certain aspects, the solubilization component comprises two or more constituents wherein the total concentration/amount of the two or more solubilization component constituents is represented by the concentrations/amounts provided above. For example, in some aspects, compositions can comprise a solubilization component comprising a constituent characterizable as a polyethoxylated castor oil and tromethamine. In aspects, compositions can comprise, e.g., a polyethoxylated castor oil, e.g., cremophor, in an amount representing between about 0.1% w/v to about 0.5% w/v, such as, e.g., ~0.1% w/v–~0.4% w/v, or ~0.1% w/v–~0.3% w/v, such as, e.g., about 0.25% w/v of the composition. In aspects, compositions can comprise, e.g., tromethamine, in an amount representing between about 0.1% w/v to about 0.5% w/v, such as, e.g., ~0.1% w/v–~0.4% w/v, ~0.1% w/v–~0.3% w/v, or ~0.1% w/v–~0.2% w/v, such as, e.g., about 0.185% w/v of the composition. In aspects, compositions can comprise a solubilization component comprising at least two solubilization constituents, wherein the total amount of the at least two solubilization constituents represents between about 0.2% w/v to about 0.6% w/v of the composition, such as, e.g., ~0.3% w/v–~0.5% w/v, e.g., ~0.4% w/v or, e.g., ~0.435% w/v of the composition.

In aspects, the solubilization component comprises a single constituent wherein the single constituent is present in an amount represented by the concentrations/amounts provided above. In certain aspects, the solubilization component comprises two or more polyoxyethylene sorbitan fatty acid esters wherein the total amount of the two or more polyoxyethylene sorbitan fatty acid esters is represented by the concentrations/amounts provided above. In aspects, the solubilization component comprises a single polyoxyethylene sorbitan fatty acid ester, wherein the total amount of the single polyoxyethylene sorbitan fatty acid ester is represented by the concentrations/amounts provided above. In certain aspects, the solubilization component comprises a single constituent, the single constituent being a polyoxyethylene sorbitan fatty acid ester, such as, e.g., polysorbate 80, wherein the single polyoxyethylene sorbitan fatty acid ester, e.g., polysorbate 80, is present in an amount representing ~0.05% w/v–~5% w/v, ~0.1% w/v–~4% w/v, ~0.15% w/v–~3% w/v, ~0.2% w/v–~2% w/v, ~0.2% w/v–~1% w/v, or ~0.2% w/v–~0.5% w/v, such as for example about 0.25% w/v of the composition. In aspects, the single constituent of the solubilization component is polysorbate 80.

In this and any other ingredient aspect of the invention, the invention also can be characterized as comprising a "means" for providing a recited function, here imparting/ providing an effective, detectable, or significant solubilization effect (e.g., increased solubilization) to one or more constituents of composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described solubilization agents/compounds or components can be described as solubilization means or means for providing effective, detectable, or significant solubilization activity/characteristics to one or more constituents of the composition.)

Combination Solubilization/Penetration Enhancer Component (Solubilizing Agent(s)/Penetration Enhancer(s))

In certain aspects, a single ingredient of compositions provided by the invention can be a constituent of both a penetration enhancer component and a solubilization component. E.g., in aspects, a single ingredient of compositions provided by the invention can be characterized as capable of providing both detectable and significant solubilization effect and detectable and significant penetration enhancement effect, such affects being described above in each of the solubilization component and penetration enhancer component sections, respectively. Therefore, in aspects, one or more compounds provided in the section entitled "Penetration Enhancer Component (Penetration Enhancer(s))," having penetration enhancing effect(s), can, in aspects be interpreted as being repeated in the section entitled "Solubilization Component (Solubilizing Agent(s))," having solubilization effect(s). Further, in aspects, one or more compounds provided in the section entitled "Solubilization Component (Solubilizing Agent(s))," having solubilization effect(s), can, in aspects, be interpreted as being repeated in the section entitled "Penetration Enhancer Component (Penetration Enhancer(s))," having penetration enhancing effect(s).

In aspects, one or more ingredients providing both a detectable or significant penetration enhancing effect and a detectable or significant solubilization effect can further provide detectable or significant demulcent effect. In certain aspects, an ingredient providing both a detectable or significant penetration enhancing effect and a detectable or significant solubilization effect does not provide detectable or significant demulcent effect. That is, in aspects, a single ingredient providing both penetration enhancer functionality and solubilizing functionality, and a demulcent, can be differing compounds.

Exemplary combination solubilizer and the penetration enhancer compounds include, e.g., one or more of pharmaceutically acceptable and ophthalmologically suitable polyoxyethylene sorbitan fatty acid esters, tocopheryl polyethylene glycol succinate (TPGS), poly-arginine, polyserine, tromethamine (tris), sesame seed oil or oils having similar compositions and functional characteristics suitable for ophthalmic use, etc. Exemplary polyoxyethylene sorbitan fatty acid esters include but not limited to polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65). In some aspects the polyoxyethylene sorbitan fatty acid ester can be a polyoxyethylene sorbitan oleate/polyoxyethylene sorbitan mono-oleate ester (e.g., polysorbate 80).

In aspects, compositions provided by the invention comprise a single ingredient providing both penetration enhancement and solubilization functionality, wherein the single ingredient is present in the composition in a concentration representing between about 0.05% w/v to about 5% w/v of the composition, such as, e.g., ~0.1% w/v-~5% w/v, ~0.15% w/v-~5% w/v, ~0.2% w/v-~5% w/v, or ~0.25% w/v-~5% w/v, such as ~0.05% w/v-~5% w/v, ~0.05% w/v-~4.5% w/v, ~0.05% w/v-~4% w/v, ~0.05% w/v-~3.5% w/v, ~0.05% w/v-~3% w/v, ~0.05% w/v-~2.5% w/v, ~0.05% w/v-~2% w/v, ~0.05% w/v-~1.5% w/v, or ~0.05% w/v-~1% w/v, such as ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v of the composition. In certain aspects, the single ingredient is a polyoxyethylene sorbitan fatty acid ester, such as, e.g., polysorbate 80, wherein the single polyoxyethylene sorbitan fatty acid ester, e.g., polysorbate 80, is present in an amount representing ~0.05% w/v-~5% w/v, ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v of the composition. In aspects, the single constituent of the solubilization component is polysorbate 80. In aspects, the single ingredient, e.g., the single polyoxyethylene sorbitan fatty acid ester, e.g., polysorbate 80, further provides detectable or significant demulcent effect.

Demulcent Component (Demulcent(s))

In aspects, compositions provided by the invention comprise a demulcent component. In aspects, the demulcent component comprises any one or more pharmaceutically acceptable and ophthalmologically suitable constituents (e.g., pharmaceutically acceptable and ophthalmologically suitable compounds) which detectably or significantly increase the soothing effect of the composition; detectably or significantly reduce the degree of, or prevent, irritation caused by the composition or caused by one or more other constituents of the composition; detectably or significantly reduce the degree of, or prevent, inflammation caused by the composition or caused by one or more other constituents of the composition; or a combination thereof. In aspects, the demulcent component can comprise any one or more pharmaceutically acceptable or ophthalmologically suitable compounds capable of demonstrating such an effect.

In aspects, one or more constituents of the demulcent component can further provide one or more additional detectable or significant functionalities, such as, for example, detectable or significant penetration enhancement effect (such as is described elsewhere herein), detectable or significant solubilization effect, detectable or significant viscosity enhancing effect/thickening effect, or a combination thereof. That is, in one aspect, a demulcent constituent of the demulcent component also provides detectable or significant penetration enhancement effect. In one aspect, a demulcent constituent of the demulcent component also provides detectable or significant solubilization effect. In one aspect, a demulcent constituent of the demulcent component also provides detectable or significant viscosity enhancing/thickening effect. In one aspect, a demulcent constituent of the demulcent component also provides both detectable or significant penetration enhancement effect and detectable or significant solubilization effect. In one aspect, a demulcent constituent of the demulcent component also provides detectable or significant viscosity enhancing/thickening effect. In certain aspects, a demulcent constituent of the demulcent component does not provide a penetration enhancement effect, a solubilization effect, or a viscosity enhancing/thickening effect. That is, in aspects, a penetration enhancer and a demulcent, a solubilizer and a demulcent, or, e.g., a demulcent and a thickening agent can be differing compounds.

In aspects, a demulcent component of a composition can comprise any ophthalmologically suitable and pharmaceutically acceptable demulcent which does not detectably or significantly interfere with the required functionality of any one or more other composition constituents In aspects, exemplary constituents of a demulcent component comprise, e.g., a constituent which also provides detectable or significant penetration enhancement activity, solubilization activity, or both penetration enhancement activity and solubilization activity, such as, e.g., polysorbate 80. In some aspects the polyoxyethylene sorbitan fatty acid ester can be a polyoxyethylene sorbitan oleate/polyoxyethylene sorbitan mono-oleate ester (e.g., polysorbate 80). In some aspects, exemplary constituents of a demulcent component comprise, e.g., one or more polyols (sugar-like hydrogenated carbohydrates; sometimes referred to as polyhydric alcohols), e.g., polyols in liquid form, such as for example glycerin, polyethylene glycol 300, polyethylene glycol 400, polysorbate 80 as described previously, propylene glycol, etc.

In aspects, exemplary constituents of a demulcent component comprise, e.g., one or more of pharmaceutically acceptable and ophthalmologically suitable cellulose derivatives, such as, e.g., carboxymethylcellulose sodium, hydroxyethyl cellulose, hypromellose, methylcellulose, etc.

In alternative aspects, an exemplary constituent of a demulcent component is, e.g., a high-molecular-weight polysaccharide, e.g., dextran 70. In still further aspects, an exemplary constituent of a demulcent component is, e.g., gelatin. In yet further aspects, an exemplary constituent of a demulcent component is, e.g., polyvinyl alcohol (PVA). In some aspects, an exemplary constituent of a demulcent component is, e.g., povidone.

In aspects, compositions provided by the invention comprise a demulcent component comprising one or more demulcent constituents, wherein the demulcent component is present in the composition in a concentration representing between about 0.01% w/v to about 5% or about 0.05% w/v to about 5% w/v of the composition, such as, e.g., ~0.1% w/v-~5% w/v, ~0.15% w/v-~5% w/v, ~0.2% w/v-~5% w/v, or ~0.25% w/v-~5% w/v, such as ~0.05% w/v-~5% w/v, ~0.05% w/v-~4.5% w/v, ~0.05% w/v-~4% w/v, ~0.05% w/v-~3.5% w/v, ~0.05% w/v-~3% w/v, ~0.05% w/v-~2.5% w/v, ~0.05% w/v-~2% w/v, ~0.05% w/v-~1.5% w/v, or ~0.05% w/v-~1% w/v, such as ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v of the composition.

In certain aspects, the demulcent component comprises two or more constituents wherein the total concentration/amount of the two or more demulcent component constituents is represented by the concentrations/amounts provided above. In aspects, the demulcent component comprises a single constituent wherein the single constituent is present in an amount represented by the concentrations/amounts provided above. In certain aspects, the demulcent component comprises two or more of polyoxyethylene sorbitan fatty acid esters wherein the total amount of the two or more polyoxyethylene sorbitan fatty acid esters is represented by the concentrations/amounts provided above. In aspects, the solubilization component comprises a single polyoxyethylene sorbitan fatty acid ester, wherein the total amount of the single polyoxyethylene sorbitan fatty acid ester is represented by the concentrations/amounts provided above. In certain aspects, the solubilization component comprises a single constituent, the single constituent being a polyoxyethylene sorbitan fatty acid ester, such as, e.g., polysorbate 80, wherein the single polyoxyethylene sorbitan fatty acid ester, e.g., polysorbate 80, is present in an amount representing ~0.05% w/v-~5% w/v, ~0.1% w/v-~4% w/v, ~0.15% w/v-~3% w/v, ~0.2% w/v-~2% w/v, ~0.2% w/v-~1% w/v, or ~0.2% w/v-~0.5% w/v, such as for example about 0.25% w/v of the composition. In aspects, the single constituent of the solubilization component is polysorbate 80.

In certain alternative aspects, compositions comprise a demulcent component wherein the demulcent component comprises a cellulose derivative in an amount of between about 0.2% w/v-about 2.5% w/v of the composition, typically in an amount of less than or equal to about 1% w/v. In aspects, compositions comprise a demulcent component wherein the demulcent component comprises dextran 70 in an amount of about 0.1% w/v of the composition. In aspects, a demulcent component comprising dextran 70 further comprises one or more additional demulcent constituents. In aspects, compositions comprise a demulcent component wherein the demulcent component comprises gelatin in an amount of about 0.01% w/v of the composition. In aspects, compositions comprise a demulcent component wherein the demulcent component comprises polyvinyl alcohol (PVA) in an amount of about 0.1% w/v-about 4% w/v of the composition. In aspects, compositions comprise a demulcent component wherein the demulcent component comprises povidone in an amount of about 0.1% w/v-about 2% w/v of the composition.

In this and any other ingredient aspect of the invention, the invention also can be characterized as comprising a "means" for providing a recited function, here imparting/providing an effective, detectable, or significant demulcent effect (e.g., soothing, or reduced irritation effect) to one or more constituents of composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described demulcent agents/compounds or components can be described as demulcent means or means for providing effective, detectable, or significant demulcent activity/characteristics to one or more constituents of the composition.)

In aspects, treatment of an ophthalmic condition/ocular condition with compositions provided by the invention comprising a demulcent component, e.g., comprising polysorbate 80 or one or more other demulcents of a demulcent component, detectably or significantly reduce or prevent inflammation, irritation, or both, over similar compositions not comprising a demulcent.

Tonicity Component (Tonicity Agent(s))

In aspects, compositions provided by the invention comprise a tonicity component. In aspects, the tonicity component comprises any one or more pharmaceutically acceptable and ophthalmologically suitable constituents (e.g., pharmaceutically acceptable and ophthalmologically suitable compounds) which detectably or significantly modify or aid in the establishment of the tonicity of the composition. In aspects, the tonicity component can comprise any one or more pharmaceutically acceptable or ophthalmologically suitable compounds capable of demonstrating such an effect. In aspects, the tonicity agents/constituents of the tonicity component are suitable for establishing compositions having a targeted isotonic range, e.g., an osmolality of about 171 mOsm/Kg-about 1711 mOsm/K, such as, e.g., about 200 mOsm/Kg-about 1000 mOsm/K, about 250 mOsm/Kg-about 500 mOsm/Kg, or, e.g., about 280 mOsm/Kg to about 370 mOsm/Kg.

In aspects, a tonicity component of a composition can comprise any ophthalmologically suitable and pharmaceutically acceptable tonicity agent which does not detectably or significantly interfere with the required functionality of any one or more other composition constituents. In aspects, exemplary constituents of a tonicity component comprise, e.g., any one or more pharmaceutically acceptable and ophthalmologically suitable tonicity agents including, e.g., sodium chloride, potassium chloride, dextrose, glucose, glycerol, mannitol, other electrolytes, etc.

In aspects, compositions provided by the invention comprise a tonicity component comprising one or more tonicity agents, wherein the tonicity component is present in the composition in a concentration representing between about 0.005% w/v to about 1% w/v of the composition, such as, e.g., ~0.005% w/v-~0.95% w/v, ~0.005% w/v-~0.9% w/v, ~0.005% w/v-~0.85% w/v, or ~0.005% w/v-~0.8% w/v, such as, e.g., ~0.05% w/v-~1% w/v, ~0.1% w/v-~1% w/v, ~0.2% w/v-~1% w/v, ~0.3% w/v-~1% w/v, ~0.4% w/v-~1% w/v, ~0.5% w/v-~1% w/v, ~0.6% w/v-~1% w/v, ~0.7% w/v-~1% w/v, or ~0.8% w/v-~1% w/v. In aspects, the tonicity component is present in compositions provided by the invention in an amount of between about 0.5% w/v and about 1% w/v of the composition.

In certain aspects, compositions provided by the invention comprise a tonicity component comprising one or more tonicity agents, wherein the tonicity component is present in the composition in a concentration representing between about 0.005% w/v to about 0.1% w/v of the composition, such as, e.g., ~0.005% w/v-~0.095% w/v, ~0.005% w/v-~0.09% w/v, ~0.005% w/v-~0.085% w/v, or ~0.005% w/v-~0.08% w/v, e.g., ~0.01% w/v-~0.1% w/v, ~0.02% w/v-~0.1% w/v, ~0.03% w/v-~0.1% w/v, ~0.04% w/v-~0.1% w/v, ~0.05% w/v-~0.1% w/v, ~0.06% w/v-~0.1% w/v, ~0.07% w/v-~0.1% w/v, or ~0.08% w/v-~0.1% w/v of the composition.

In certain aspects, compositions provided by the invention comprise a tonicity component comprising one or more tonicity agents, wherein the tonicity component is present in the composition in a concentration representing between about 2% w/v to about 6% w/v of the composition, such as, e.g., ~2.5% w/v-~6% w/v, ~3% w/v-~6% w/v, ~3.5% w/v-~6% w/v, ~4% w/v-~6% w/v, or ~4.5% w/v-~6% w/v, e.g., ~2% w/v-~5.5% w/v, or ~2% w/v-~4.5% w/v, such as, e.g., ~2.5% w/v-~5.5% w/v, ~3% w/v-~5% w/v, ~3.5% w/v-~5% w/v, or ~4% w/v-~5% w/v, such as, e.g., ~4.5% w/v.

In certain aspects, the tonicity component comprises two or more constituents wherein the total concentration/amount of the two or more tonicity component constituents is represented by the concentrations/amounts provided above. In aspects, the tonicity component comprises a single constituent wherein the single constituent is present in an amount represented by the concentrations/amounts provided above. In certain aspects, the tonicity component comprises a single constituent, the single constituent being sodium chloride, wherein the sodium chloride is present in an amount representing between about 0.005% w/v to about 0.1% w/v of the composition, such as, e.g., ~0.005% w/v-~0.095% w/v, ~0.005% w/v-~0.09% w/v, ~0.005% w/v-~0.085% w/v, or ~0.005% w/v-~0.08% w/v, such as, e.g., ~0.01% w/v-about 0.1% w/v, ~0.02% w/v-~0.1% w/v, ~0.03% w/v-~0.1% w/v, ~0.04% w/v-~0.1% w/v,~0.05% w/v-~0.1% w/v, ~0.06% w/v-~0.1% w/v, ~0.07% w/v-~0.1% w/v, or for example ~0.08% w/v-~0.1% w/v, such as, e.g., ~0.05% w/v-~0.1% w/v, ~0.07% w/v-~0.09% w/v, or, e.g., ~0.08% w/v. In certain aspects, the tonicity component comprises a single constituent, the single constituent being mannitol, wherein the mannitol is present in an amount representing between about 2% w/v to about 6% w/v, e.g., ~2.5% w/v-~5.5% w/v, ~3% w/v-~5% w/v, or ~3.5% w/v-~5% w/v, e.g., ~4% w/v-~5% w/v such as about 4.5% w/v.

Preservative Component (Preservation Agent(s))

In aspects, compositions provided by the invention comprise a preservative component. In aspects, the preservative component comprises any one or more pharmaceutically acceptable and ophthalmologically suitable constituents (e.g., pharmaceutically acceptable and ophthalmologically suitable compounds) which detectably or significantly increase the stability of the composition, detectably or significantly decrease the degradation of one or more other constituents of the composition (over a period of time/under storage conditions such as conditions comprising a temperature of between about 15° C. and about 42° C. and a relative humidity of between about 35% and about 75% relative humidity—as exemplified elsewhere herein and as is known in the art), detectably or significantly increase the period of time that the composition is considered safe and efficacious for use, detectably or significantly increases or extends shelf life by maintaining an amount of active pharmaceutical ingredient above a threshold, e.g., a PCC, e.g., pilocarpine HCl, within desirable or acceptable limits, maintaining the level of any one or more impurities below an acceptable/suitable level, or any such similar measures of composition stability, or any combination thereof. For example, in aspects, a preservative component comprises one or more pharmaceutically acceptable and ophthalmologically suitable constituents (e.g., pharmaceutically acceptable and ophthalmologically suitable compounds) which aid, e.g., via reducing or preventing microbial contamination, at least about 95%, 95%, 97%, 98% or more of the API(s) of the composition, such as, e.g., the pilocarpine compound, when stored under conditions comprising a temperature of between about 15° C. and about 42° C. and a relative humidity of between about 35% and about 75% relative humidity, such as at about 15° C.-about 27° C. and about 60% relative humidity, when stored at about 38° C.-about 42° C. and 75% relative humidity, or when stored under either/or any such condition, for a period of at least about 1, 3, 6, 9, 12, 18, 24, or, e.g., at least about 36 months. As another example, in aspects, a preservative component comprises one or more pharmaceutically acceptable and ophthalmologically suitable constituents (e.g., pharmaceutically acceptable and ophthalmologically suitable compounds) which aid, e.g., via reducing or preventing microbial contamination, the composition in maintaining a level of total impurities which is less than about 2.5% after storage under conditions comprising a temperature of between about 15° C. and about 42° C. and a relative humidity of between about 35% and about 75% relative humidity, e.g., at about 15° C.-about 27° C. and about 60% relative humidity, after storage at about 38° C.-about 42° C. and 75% relative humidity, or after storage under either/or any such condition, for a period of at least about 1, 3, 6, 9, 12, 18, 24, or, e.g., at least about 36 months.

In aspects, the preservation component can comprise any one or more pharmaceutically acceptable or ophthalmologically suitable compounds capable of demonstrating such an effect.

In aspects, one or more preservative agents of a preservation component provide one or more other detectably or significant functional activities, such as for example, providing detectable or significant penetration enhancement activity, such as, e.g., detectably or significantly enhancing the penetration of one or more PCC constituents, e.g., a pilocarpine compound, e.g., pilocarpine hydrochloride, into an ocular tissue. In aspects, one or more preservative agents of a preservation component provide detectable or significant solubilization activity, such as, e.g., detectably or significantly enhancing the solubilization of, or detectably or significantly maintaining the solubilization of, one or more composition constituents, e.g., one or more PCC constituents, e.g., a pilocarpine compound, e.g., pilocarpine hydrochloride.

In aspects, the pharmaceutically acceptable and ophthalmologically suitable compositions provided by the invention comprise a preservative component comprising one or more preservation agents present in anti-microbially effective amounts, e.g., an amount capable of detectably or significantly inhibiting microbial growth. In aspects, a preservation component of a composition can comprise any ophthalmologically suitable and pharmaceutically acceptable preservative which does not detectably or significantly interfere with the required functionality of any one or more other composition constituents. In aspects, exemplary constituents of a preservative component comprise, e.g., hydrogen peroxide; sorbic acid; biquanides; quaternary ammonium salts such as benzalkonium chloride(s) (abbreviated herein as BKC, though in other literature other abbreviations such as BAC, BAK, or BZK may be used) and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; thiomersal, etc. In aspects, a preservative component can comprise benzalkonium chloride(s) (BKC), wherein the BKC provides detectable or significant penetration enhancement activity, detectable or significant preservation activity, detectable or significant solubilization effect(s), or any combination thereof. Benzalkonium chlorides, a class of quaternary ammonium compounds suitable for use in compositions herein, include, e.g., known as alkyl dimethyl benzyl ammonium chlorides (or ADBAC), alkyl dimethyl (phenylmethyl) chlorides, and ammonium alkyl dimethyl benzyl chlorides.

In aspects, compositions provided by the invention comprise a preservation component comprising one or more preservation agents, wherein the preservation component is present in the composition in a concentration representing between about 0.0001% w/v to about 0.02% w/v, such as, e.g., ~0.001% w/v–~0.015% w/v, ~0.001% w/v–~0.01% w/v, or ~0.001% w/v–~0.008% w/v, ~0.002% w/v–~0.02% w/v, ~0.004% w/v–~0.02% w/v, or ~0.006% w/v–~0.02% w/v, e.g., ~0.0005% w/v–~0.015% w/v, ~0.001% w/v–~0.01% w/v, ~0.002% w/v–~0.009% w/v, ~0.004% w/v–~0.008% w/v, or ~0.006% w/v–~0.008% w/v, such as, e.g., about 0.0075% w/v of the composition.

In aspects, a preservation component can comprise a quaternary ammonium salt, e.g., benzalkonium chloride, present in the formulation in a concentration of between about 0.0001% w/v to 0.02% w/v, such as between about 0.003% w/v to about 0.02% w/v, such as between about 0.005% w/v to about 0.02% w/v, or for example about 0.0075% w/v, 0.01% w/v, or, e.g., about 0.02% w/v. In some aspects, compositions provided by the invention comprise benzalkonium chloride in an amount of less than about 0.01% w/v.

In aspects, antimicrobial effective amounts of a preservative may be determined by performing preservative efficacy tests or antimicrobial effectiveness tests. These tests are inter alia described in Chapter 51 of the United States Pharmacopeia 29-National Formulary 24 (USP 29-NF 24). In aspects, preservative agents of a preservation component are used in an amount within the concentration ranges described in standard reference books like Remington's Pharmaceutical Sciences and Handbook of Pharmaceutical Excipients (e.g., the $23^{rd}$ Edition thereof—Published in 2020).

In certain aspects, the preservation component comprises two or more constituents wherein the total concentration/amount of the two or more preservation component constituents is represented by the concentrations/amounts provided above. In aspects, the preservation component comprises a single constituent wherein the single constituent is present in an amount represented by the concentrations/amounts provided above, such as, e.g., benzalkonium chloride in amounts provided above.

In this and any other ingredient aspect of the invention, the invention also can be characterized as comprising a "means" for providing a recited function, here imparting/providing an effective, detectable, or significant preservation effect (e.g., increased stability of one or more constituents of the composition, maintenance of an acceptable level of impurities during composition storage, increased composition shelf life, etc.) of compositions. In such a respect, any known equivalents of such named agents can also be, e.g., are, incorporated into compositions or methods of the invention. As with other sections similarly described herein, any of the components of the invention can be, where suitable, described as means (e.g., the above-described preservation agents/compounds or components can be described as preservation means or means for providing effective, detectable, or significant preservation activity/characteristics to the composition or one or more constituents of the composition.)

Viscosity Enhancer/Thickening Component (Viscosity Enhancing Agent(s)/Thickening Agent(s))

In aspects, compositions provided by the invention comprise a viscosity enhancer component (also referred to as a thickening component). In aspects, the thickening component comprises any one or more pharmaceutically acceptable and ophthalmologically suitable constituents (e.g., pharmaceutically acceptable and ophthalmologically suitable compounds) which detectably or significantly increase the viscosity or thickness of one or more other constituents of the composition. In certain aspects, one or more constituents of a viscosity enhancing component change form under certain conditions so as to modify the viscosity of the composition (such as, e.g., a gel forming agent of a composition.) In a specific example, one or more constituents of a viscosity enhancing component gels when ionic content increases, such that, e.g., the composition comprising the constituent is liquid when packaged, prior to administration (e.g., when in its final packaging), however when administered to/delivered to a mammalian eye, the composition thickens, e.g., gels. In aspects, constituent(s) of a thickening component detectably or significantly improve the form of the formulation for convenient administration (e.g., make the composition easier for a user to apply). In aspects, constituent(s) of a thickening component detectably or significantly improve, e.g., increase, contact of the composition with eye tissue, or, e.g., detectably or significantly increase the length of time the composition maintains contact with eye tissue following administration, and, thereby, detectably or significantly improves (e.g., detectably or significantly increases) bioavailability of active pharmaceutical ingredient(s) of the composition, such as, e.g., constituents of the PCC, such as a pilocarpine compound, e.g., a salt of pilocarpine, e.g., pilocarpine hydrochloride. In aspects, one or more constituents of the thickening component can further provide one or more additional detectable or significant functionalities, such as, e.g., detectable or significant demulcent effect.

In aspects, the thickening component can comprise any one or more pharmaceutically acceptable or ophthalmologically suitable compounds capable of demonstrating such effect(s). In aspects, a thickening component of a composition can comprise any ophthalmologically suitable and pharmaceutically acceptable thickening agent which does not detectably or significantly interfere with the required functionality of any one or more other composition constituents.

In aspects, exemplary constituents of a thickening component comprise, e.g., polymers containing, mostly composed, generally consisting of, or consisting of, hydrophilic groups such as monosaccharides and polysaccharides, ethylene oxide groups, hydroxyl groups, carboxylic acids, or other charged functional groups.

In aspects, exemplary polymer constituents of a thickening component are high molecular weight polymers, e.g., polymers having a molecular weight of at least about 15,000 Daltons, such as, e.g., ≥~20,000 Daltons, ≥~30,000 Daltons, ≥~40,000 Daltons, or, e.g., ≥~50,000 Daltons, e.g., about 15,000 Daltons to about 50,000 Daltons.

In aspects, exemplary polymer constituents of a thickening component have a molecular weight of at least about 50,000 Daltons, such as, e.g., ≥~60,000 Daltons, ≥~70,000 Daltons, ≥~80,000 Daltons, ≥~90,000 Daltons, or, e.g., ≥~100,000 Daltons, such as, e.g., ~50,000 Daltons to ~100,000 Daltons.

In aspects, exemplary polymer constituents of a thickening component have a molecular weight of at least about 100,000 Daltons, such as, e.g., ≥~110,000 Daltons, ≥~120,000 Daltons, ≥~130,000 Daltons, ≥~140,000 Daltons, ≥~150,000 Daltons, ≥~160,000 Daltons, ≥~170,000 Daltons, ≥~180,000 Daltons, ≥~190,000 Daltons or, e.g., ≥~200,000 Daltons, such as, e.g., ~100,000 Daltons to ~200,000 Daltons.

In aspects, exemplary polymer constituents of a thickening component have a molecular weight of at least about 200,000 Daltons, such as, e.g., ≥~210,000 Daltons, ≥~220,000 Daltons, ≥~230,000 Daltons, ≥~240,000 Daltons, ≥~250,000 Daltons, ≥~260,000 Daltons, ≥~270,000 Daltons, ≥~280,000 Daltons, ≥~290,000 Daltons, or ≥~300,000 Daltons, such as, e.g., ~200,000 Daltons-~300,000 Daltons.

In aspects, exemplary polymer constituents of a thickening component have a molecular weight of at least about 300,000 Daltons, such as, e.g., ≥~310,000 Daltons, ≥~320,000 Daltons, ≥~330,000 Daltons, ≥~340,000 Daltons, ≥~350,000 Daltons, ≥~360,000 Daltons, ≥~370,000 Daltons, ≥~380,000 Daltons, ≥~390,000 Daltons, or, e.g., ≥~400,000 Daltons, such as, e.g., ~300,000 Daltons-~400,000 Daltons.

In aspects, exemplary polymer constituents of a thickening component have a molecular weight of at least about 400,000 Daltons, such as, e.g., ≥~410,000 Daltons, ≥~420,000 Daltons, ≥~430,000 Daltons, ≥~440,000 Daltons, ≥~450,000 Daltons, ≥~460,000 Daltons, ≥~470,000 Daltons, ≥~480,000 Daltons, ≥~490,000 Daltons, or ≥~500,000 Daltons, such as, e.g., ~410,000 Daltons-~500,000 Daltons.

In certain aspects, exemplary polymer constituents of a thickening component have a molecular weight of at least about 500,000 Daltons, such as ~500,000 Daltons-~1,500,000 Daltons, e.g., 500,000 Daltons-~1,250,000 Daltons, 500,000 Daltons-~1,000,000 Daltons, or 500,000 Daltons-~750,000 Daltons, e.g., 750,000 Daltons-~1,500,000 Daltons, 1,000,000 Daltons-~1,500,000 Daltons, or 1,250,000 Daltons-~1,500,000 Daltons. In certain aspects, exemplary polymer constituents of a thickening component have a molecular weight of greater than 1,500,000 Daltons.

In certain aspects, exemplary polymer constituents of a thickening component provide a detectable or significant increase in viscosity compared to the composition without the constituent(s), such as, e.g., an increase in viscosity over the composition without the constituent(s) either (a), while packaged, prior to use, (b) after administration to a mammalian eye (e.g., upon being placed under detectably or significantly different tonicity conditions), or (c) both (a) and (b), of at least about 0.5%, ≥~1%, ≥~3%, ≥~5%, ≥~10%, ≥~15%, ≥~20%, ≥~25%, ≥~30%, ≥~35%, ≥~40%, ≥~45%, or, e.g., ≥~50%.

In aspects, examples of suitable viscosity-enhancing agents include, e.g., sodium carboxymethylcellulose, hydroxypropylmethylcellulose, povidone, polyvinyl alcohol, polyethylene glycol, and gellan gum. In certain aspects, formulations described herein lack any thickening (e.g., viscosity-enhancing) compounds or agents.

In aspects, compositions provided by the invention comprise a thickening component comprising one or more thickening agents, wherein the thickening component is present in the composition in a concentration representing between about 0.1% w/v to about 1% w/v of the composition, such as, e.g., ~0.1% w/v-~0.9% w/v, ~0.1% w/v-~0.8% w/v, ~0.1% w/v-~0.7% w/v, or ~0.1% w/v-~0.6% w/v, e.g., ~0.2% w/v-~1% w/v, ~0.3% w/v-~1% w/v, ~0.4% w/v-~1% w/v, ~0.5% w/v-~1% w/v, or ~0.6% w/v-~1% w/v, such as, e.g., ~0.2% w/v-~9% w/v, ~0.3% w/v-~0.8% w/v, ~0.4% w/v-~0.7% w/v, ~0.5% w/v-~0.7% w/v, or, e.g., about 0.6% w/v of the composition.

In certain aspects, the thickening component comprises two or more constituents wherein the total concentration/amount of the two or more thickening component constituents is represented by the concentrations/amounts provided above. In aspects, the solubilization component comprises a single constituent wherein the single constituent is present in an amount represented by the concentrations/amounts provided above. In certain aspects, the solubilization component comprises a single constituent, the single constituent being gellan gum, wherein the gellan gum, is present in an amount representing ~0.2% w/v-~0.9% w/v, ~0.3% w/v-~0.8% w/v, ~0.4% w/v-~0.7% w/v, ~0.5% w/v-~0.7% w/v, or, e.g., about 0.6% w/v of the composition.

In this and any other ingredient aspect of the invention, the invention also can be characterized as comprising a "means" for providing a recited function, here imparting/providing an effective, detectable, or significant viscosity enhancing/thickening effect to composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described thickening agents/compounds or components can be described as viscosity enhancing/thickening means or means for providing effective, detectable, or significant viscosity enhancing/thickening activity/characteristics to the composition.)

Chelation Component (Chelating Agent(s))

In aspects, compositions provided by the invention comprise a chelation component. In aspects, the chelation component comprises any one or more pharmaceutically acceptable and ophthalmologically suitable constituents (e.g., pharmaceutically acceptable and ophthalmologically suitable compounds) which detectably or significantly increase chelation within the composition, detectably or significantly supplement or enhance preservative efficacy, or a combination thereof, by forming stable water-soluble complexes (chelates) with alkaline earth and heavy metal ions. In aspects, the chelation component can comprise any one or more pharmaceutically acceptable or ophthalmologically suitable compounds capable of demonstrating such an effect. In aspects, a chelation component of a composition can comprise any ophthalmologically suitable and pharmaceutically acceptable chelating agent which does not detectably or significantly interfere with the required functionality of any one or more other composition constituents.

In aspects, exemplary constituents of a chelation component comprise, e.g., one or more of cromolyn, monomeric polyacids such as EDTA, cyclohexanediamine tetraacetic acid (CDTA), hydroxyethylethylenediamine triacetic acid (HEDTA), diethylenetriamine pentaacetic acid (DTP A), dimercaptopropane sulfonic acid (DMPS), dimercaptosuccmic acid (DMSA), aminotrimethylene phosphonic acid (ATP A), citric acid, any ophthalmologically acceptable salts thereof, and/or combinations of any two or more such compounds. In other aspects, a chelating agent can be a phosphate, such as, e.g., pyrophosphates, tripolyphosphates, and, hexametaphosphates; a chelating antibiotic such as chloroquine and tetracycline; a nitrogen-containing chelating agent containing two or more chelating nitrogen atoms within an imino group or in an aromatic ring (e.g., diimines, 2,2'-bipyridines, etc.); or for example a polyamine such as cyclam (1,4,7,11-tetraazacyclotetradecane), N—($C_1$-$C_{30}$ alkyl)-substituted cyclams (e.g., hexadecyclam, tetramethylhexadecylcyclam), diethylenetriamine (DETA), spermine, diethylnorspermine (DENSPM), diethylhomospermine (DEHOP), and deferoxamine (N'-[5-[[4-[[5-(acetylhydroxyamino) pentyl] amino]-1,4-dioxobutyl]hydroxyamino]pentyl]-N'-(5-aminopentyl)-N-hydroxybutanediamide; also known as desferrioxamine B and DFO).

In certain aspects, a chelation component of compositions provided by the invention comprise EDTA or an ophthalmologically suitable EDTA salt such as, e.g., diammonium EDTA, disodium EDTA, dipotassium EDTA, triammonium EDTA, trisodium EDTA, tripotassium EDTA, or calcium disodium EDTA. In certain aspects, compositions lack any one or more of EDTA or an EDTA salt.

In aspects, compositions provided by the invention comprise a chelation component comprising one or more chelating agents, wherein the chelation component is present in the composition in a concentration representing about 0.01% w/v to about 0.5% w/v, such as for example ~0.05% w/v-~0.5% w/v, ~0.1% w/v-~0.5% w/v, or ~0.2% w/v-~0.5% w/v, e.g., ~0.01% w/v-~0.45% w/v, ~0.01% w/v-~0.4% w/v, or ~0.01% w/v-~0.3% w/v, such as, e.g., about 0.1% w/v-about 0.4% w/v of the composition.

In certain aspects, the chelation component comprises two or more constituents wherein the total concentration/amount of the two or more chelation component constituents is represented by the concentrations/amounts provided above. In aspects, the chelation component comprises a single constituent wherein the single constituent is present in an amount represented by the concentrations/amounts provided above, such as, e.g., edetate disodium in amounts provided above.

In this and any other ingredient aspect of the invention, the invention also can be characterized as comprising a "means" for providing a recited function, here imparting/providing an effective, detectable, or significant chelating effect (e.g., forming stable water-soluble complexes (chelates) with alkaline earth and heavy metal ions) of compositions. In such a respect, any known equivalents of such named agents can also be, e.g., are, incorporated into compositions or methods of the invention. As with other sections similarly described herein, any of the components of the invention can be, where suitable, described as means (e.g., the above-described chelating agents/compounds or components can be described as chelation means or means for providing effective, detectable, or significant chelation activity/characteristics to the composition or one or more constituents of the composition.)

pH Adjusting Component (pH Adjusting Agent(s))

In aspects, compositions provided by the invention comprise a pH adjusting component. In aspects, the pH adjusting component comprises any one or more pharmaceutically acceptable and ophthalmologically suitable constituents (e.g., pharmaceutically acceptable and ophthalmologically suitable compounds) which detectably or significantly alter or aid in the establishment of a target pH of the composition, such as a pH of between about 3 to about 6. In aspects, the pH adjusting component can comprise any one or more pharmaceutically acceptable or ophthalmologically suitable compounds capable of demonstrating such an effect. In aspects, a pH adjusting component of a composition can comprise any ophthalmologically suitable and pharmaceutically acceptable pH adjusting agent which does not detectably or significantly interfere with the required functionality of any one or more other composition constituents.

In aspects, one or more constituents of the pH adjusting component can further provide one or more additional detectable or significant functionalities, such as, for example, detectable or significant buffering effects. In aspects, a pH adjusting agent can be a compound different from a buffer/buffering agent.

In aspects, exemplary constituents of a buffer component comprise, e.g., one or more of sodium hydroxide, sodium carbonate, sodium bicarbonate, potassium hydroxide, ammonium carbonate, hydrochloric acid, lactic acid, phosphoric acid, sodium phosphate, sulfuric acid, etc. In aspects, such agents can be used to adjust the pH to a desirable/target range, such as, e.g., to between about 3 to about 6, such as ~3.5-~5.5, or ~4-~4.5. In aspects, the pH of the compositions, e.g., compositions comprising pilocarpine HCl, can be adjusted in any suitable manner by means of the addition of pH adjusting agents in an amount sufficient to establish and maintain a pH of the compositions from about 3.0 to about 6.0, for example by addition of aqueous hydrochloric acid solutions or aqueous sodium hydroxide solutions. Such solutions can be diluted or concentrated. Thus, in aspects, suitable pH adjusting agents include, but are not limited to 0.01 molar (M) hydrochloric acid, 0.1M hydrochloric acid, 1M hydrochloric acid, 2M hydrochloric acid, 3M hydrochloric acid, 4M hydrochloric acid, 5M hydrochloric acid, 6M hydrochloric acid, 0.01M sodium hydroxide, 0.1M sodium hydroxide, 1M sodium hydroxide, 2M sodium hydroxide, 3M sodium hydroxide, 4M sodium hydroxide, 5M sodium hydroxide, and 6M sodium hydroxide. In one aspect, suitable pH adjusting agents include, e.g., 1M hydrochloric acid and 1M sodium hydroxide.

In aspects, compositions provided by the invention can comprise a pH adjusting component comprising one or more pH adjusting agent(s), wherein the pH adjusting component is present in the compositions provided by the invention in an amount effective in providing the target pH. In aspects, such an amount can be considered a "trace amount," e.g., less than ~0.005% w/v, <0.004% w/v, <~0.003% w/v, <0.002% w/v, e.g., <~0.001% w/v. In aspects, such an amount can be an amount representing between about 0-about 0.01% w/v. In aspects, one or more pH adjusting agent(s) can be present in the compositions provided by the invention in an amount effective in providing the target pH, such amounts representing between about 0% w/v-about 0.1% w/v, such as, e.g., about 0.01% w/v, ~0.02% w/v, ~0.03% w/v, ~0.04% w/v, ~0.05% w/v, ~0.06% w/v, ~0.07% w/v, ~0.08% w/v, or, e.g., ~0.09% w/v.

In certain aspects, the pH adjusting component comprises two or more constituents wherein the total concentration/amount of the two or more pH adjusting component constituents within one or more ranges provided above. In aspects, the pH adjusting component comprises a single constituent wherein the single constituent is present in an amount within one or more ranges provided above. In aspects, compositions comprise sodium hydroxide, hydrochloric acid, or both sodium hydroxide and hydrochloric acid only in sufficient amounts to adjust pH during the manufacturing process (e.g., in an amount of less than 0.1% w/v, or, e.g., less than ~0.005% w/v.)

In this and any other ingredient aspect of the invention, the invention also can be characterized as comprising a "means" for providing a recited function, here imparting/providing an effective, detectable, or significant pH adjustment effect (e.g., pH establishment) to/of composition(s) of the invention. In such a respect, any known equivalents of such named agents can also be, e.g., are, incorporated into compositions or methods of the invention. As with other sections similarly described herein, any of the components of the invention can be, where suitable, described as means (e.g., the above-described pH adjusting agents/compounds or components can be described as pH adjusting means or means for providing effective, detectable, or significant pH adjustment activity/characteristics to the composition.)

Antioxidant Component (Antioxidant(s))

In aspects, compositions comprise antioxidant(s) in effective amount(s). An "antioxidant" is typically understood as referring to a substance that preferentially reacts with oxygen, thereby detectably or significantly protecting other components of a composition to which it is added from premature degradation due to oxidation (e.g., protecting APIs that is known to be detectably/significantly susceptible to oxidation).

According to aspects, one or more antioxidant compounds can be present in composition(s) of the invention as an antioxidant component, which detectably or significantly improve API stability or reduce the amount of impurities, such as, e.g., providing for a composition which is stable under room temperature storage conditions, e.g., retains at least 97% of the one or more PCC constituents, e.g., pilocarpine compound(s) when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/or any such condition for at least about one month such as ≥~2 months or such as ≥~3 months, ≥~6 months, ≥~12 months, or, e.g., ≥~18 months, ≥~24 months, or ≥~36 months.

For example, composition(s) provided by the invention can comprise an antioxidant component comprising one or more antioxidant agents which detectably improve the stability of the one or more pilocarpine compound(s), reduces the amount of composition impurities, enhances preservative effectiveness, or any or all thereof, at a period of at least 2 weeks post manufacturing, such as at a period ≥~3 weeks, ≥~1 month, ≥~6 weeks, ≥~2 months, ≥~10 weeks, ≥~3 months, ≥~14 weeks, ≥~4 months, ≥~18 weeks, ≥~5 months, ≥~22 weeks, ≥~6 months, or for even longer periods (e.g., 3-24, 3-18, 3-12, 3-36, 4-12, 4-24, 4-36, 6-12, 6-18, 6-24, or 6-36 months).

In aspects, the invention provides composition(s) comprising one or more pharmaceutically acceptable and ophthalmologically suitable antioxidant agents as constituents of an antioxidant component effective at pH range of between, e.g., ~3-~6. In aspects, antioxidant compound(s) of the composition(s) herein do not detectably or significantly negatively impact any other component of the formulation, such as, e.g., they do not detectably or significantly reduce the efficacy of any one or more API(s), e.g., pilocarpine compound(s).

In aspects any ophthalmologically suitable and pharmaceutically acceptable antioxidant can be used in methods of the invention/incorporated in compositions of the invention, in any suitably effective amount(s). In aspects, exemplary antioxidant(s) in a composition described herein can comprise, e.g., ascorbate compound(s) (e.g., sodium ascorbate, ascorbic acid, etc.), thiamine, pyridoxine, histidine, cysteine, glutathione, sodium bisulphite, sodium sulphite, sodium metabisulphite, sodium thiosulphite, sodium formaldehyde sulphoxylate, acetylcysteine, cysteine, thioglycerol, thioglycollic acid, thiolactic acid, thieurea, dihithreitol, propyl gallate, butylated hydroxyanisole, butylated hydroxytoluene, tertiary butyl hydroquinone, ascorbyl palmitate, nordihydroguaiaretic acid and alpha-tocopherol, any ophthalmologically acceptable salts thereof, or combinations of any two or more such compounds. In aspects, one or more antioxidant compound(s)/agent(s) can be present in the compositions provided by the invention in an amount representing between about 0.001 w/v. %-about 2 w/v. % of the composition, such as, e.g., ~0.001 w/v. %-~1.8 w/v. %, ~0.001 w/v. %-~1.6 w/v. %, ~0.001 w/v. %-~1.4 w/v. %, ~0.001 w/v. %-~1.2 w/v. %, ~0.08 w/v. %-~1 w/v. %, or. e.g., ~0.05-~1 w/v. % of the composition.

Carrier Component (Carrier Agent(s))

In aspects, compositions provided by the invention comprise a carrier component. In aspects, this component may be referenced as vehicle component. In aspects, the carrier component comprises any one or more pharmaceutically acceptable and ophthalmologically suitable constituents (e.g., pharmaceutically acceptable and ophthalmologically suitable carriers) which detectably or significantly maintain all constituents of the composition in deliverable form, such as in the form of a liquid, e.g., a solution, as suspension, or, e.g., a gel. In aspects, the carrier component can comprise any one or more pharmaceutically acceptable or ophthalmologically suitable carriers capable of performing such a function. In aspects, a carrier component of a composition can comprise any ophthalmologically suitable and pharmaceutically acceptable carrier which does not detectably or significantly interfere with the required functionality of any one or more other composition constituents.

In aspects, exemplary constituents of a carrier component comprise, e.g., one or more of a pharmaceutically acceptable and ophthalmologically suitable lipid (e.g., establishing a lipid vehicle), a gel (e.g., establishing a gel vehicle), an oil-based carrier (establishing an oil-based vehicle), a carrier in the form of an emulsion (establishing an emulsion vehicle), an emulsifier-containing carrier that forms an emulsion when mixed with other components, or, a carrier forming a solution vehicle, e.g., an aqueous carrier (water) to form an aqueous solution vehicle. In aspects, the carrier is an aqueous carrier. In aspects, the carrier is mostly, generally only, essentially only, substantially only, or only composed of water, e.g., water for injection (WFI) (a sterile, solute-free preparation of distilled water). In alternative aspects, other ophthalmologically suitable aqueous carriers which do not adversely affect the stability of the composition (s) may be used, such as, e.g., deionized water.

In certain aspects, the carrier is deuterated water, comprising an amount of deuteration which is detectably or significantly greater than that which is naturally occurring (e.g., that which is typically found in nature). In aspects, compositions do not comprise a deuterated carrier, such as, e.g., deuterated water. In certain common aspects, the carrier is water comprising no additional deuterium beyond that which is typically found in nature. In aspects, compositions comprise non-deuterated water, wherein "non-deuterated" describes water comprising no amount of deuteration beyond that which is typically naturally occurring. Uncontradicted, reference to "water" should be interpreted to mean non-deuterated water.

In aspects, compositions provided by the invention comprise a carrier component comprising one or more carriers, wherein the carrier component is present in a concentration representing at least about 60% w/v of the composition, such as, e.g., ≥~65% w/v, ≥~70% w/v, ≥~75% w/v, ≥~80% w/v, ≥~85% w/v, ≥~90% w/v, or ≥~95% w/v of the composition.

In certain aspects, the carrier component comprises two or more constituents wherein the total concentration/amount of the two or more carrier component constituents is represented by the concentrations/amounts provided above. In aspects, the carrier component comprises a single constituent wherein the single constituent is present in an amount represented by the concentrations/amounts provided above. In certain aspects, the carrier component comprises a single constituent, the single constituent being water, or, e.g., water for injection (WFI), wherein the water is present in an amount representing ≥~70% w/v, ≥~75% w/v, ≥~80% w/v, ≥~85% w/v, ≥~90% w/v, or ≥~95% w/v of the composition. In aspects, the pharmaceutically acceptable and ophthalmologically suitable compositions are aqueous compositions. In aspects, compositions provided by the invention typically comprise at least about 70% w/v water, and even more typically at least about 85% w/v-about 95% w/v water.

Compositions do not Include/are not Provided as

In certain aspects, compositions provided by the invention are characterizable by one or more ingredients/agents/constituents which are not present in the compositions.

According to certain aspects of the invention, compositions provided by the invention do not comprise a chelating agent. In aspects, compositions provided by the invention do not comprise any compound which detectably or significantly increase chelation within the composition(s). In aspects, composition(s) do not comprise edetate disodium. In aspects, if compositions comprise edetate disodium, it is present in an amount which is significantly less than 0.1% w/v.

In certain embodiments, compositions provided by the invention do not comprise a polymer, such that compositions are characterizable as polymer-free. In alternative aspects, compositions require a detectable or significant amount of at least one polymeric compound.

In some aspects, compositions provided by the invention comprise only a single pharmaceutically active ingredient, such as, e.g., a single constituent of a PCC, such as, e.g., a single pilocarpine compound, e.g., a salt of pilocarpine, e.g., pilocarpine HCl. In specific examples, compositions do not comprise tropicamide. In aspects, composition(s) do not comprise an active pharmaceutical ingredient other than one or more pilocarpine compound(s). In aspects, compositions do not comprise an anti-inflammatory agent characterizable as a steroid. In aspects, compositions do not comprise an anti-inflammatory characterizable as a non-steroid anti-inflammatory drug (NSAID), such as, e.g., diclofenac or ketorolac. In specific examples, compositions do not comprise aceclidine.

In certain aspects, the PCC does not comprise, e.g., carbachol, bethanechol, methacholine, or muscarine compound(s) or combination(s) thereof. In certain aspects, the PCC does not comprise, e.g., pirenzepine, telenzepine, trihexyphenidyl, (+)(11-({2-[diethylaminomethyl]-1-piperdidinyl}acetyl)-5,11-di-hydro-6H-pyrido(2,3-b)(1,4) benzodiazepine-6-one, (+)5,11 dihydro-11-{[2-[(dipropylamino)methyl]-1piperdinyl)amino]carbonyl}-6H-pyrido(2,3-b)(1,4)benzodiazepine-6-one, himbacine, triptiramine, diphenylacetoxy-N-methylpiperidine ethiodide, (+)p-fluoro-hexahydro-sila-difenidol hydrochloride, or combination(s) of any or all thereof.

In some aspects, compositions provided by the invention do not comprise more than a single buffer agent. In aspects, compositions provided by the invention lack any buffer component. In some aspects, compositions do not comprise a buffer agent having a pKa of less than about 8. In aspects, compositions do not comprise a buffer agent having a pKa of greater than about 5. In aspects, compositions do not comprise a buffer agent having a pKa of greater than about 4. In aspects, compositions only comprise a buffer agent having at least two pKa values, e.g., a buffer agent comprising two or more ionizable groups.

According to certain aspects, compositions are not provided as a solution. In certain aspects, compositions are not provided as a suspension. In aspects, compositions are provided as a gel (as opposed to, e.g., a suspension or a solution). In aspects, compositions are provided as solutions (as opposed to, e.g., a suspension or a gel). In aspects, compositions are only provided as suspensions (as opposed to, e.g., a solution or a gel).

In aspects, compositions do not comprise sodium hyaluronate, hydroxypropyl methylcellulose, or both sodium hyaluronate and hydroxypropyl methylcellulose (such as, e.g., may be provided for lubrication or other purposes). In aspects, composition(s) provided by the invention do not comprise detectable or significant amount(s) of one or more of hyaluronic acid or a pharmaceutically acceptable salt thereof, cellulose or a cellulose derivative, carboxymethyl cellulose sodium, hydroxyethyl cellulose, methylcellulose, dextran, gelatin, a polyol, glycerin, polyethylene glycol 300, polyethylene glycol 400, propylene glycol, polyvinyl alcohol, povidone, or, e.g., combinations of two or more thereof.

According to certain aspects, compositions do not comprise a deuterated carrier. In aspects, compositions do not comprise deuterated water, e.g., water comprising an amount of deuterium atoms significantly greater than that which is found in nature.

In aspects, compositions do not comprise ophthalmic mucous penetrating particles, e.g., nanoparticles coated with a mucous penetrating agent.

In certain aspects, compositions do not comprise a component, compound, agent, constituent, etc. which significantly modifies the buffering capacity of a composition other than a buffering component or agent as described herein. In aspects, the only component or agent(s) which detectably or significantly modulate the buffering capacity of compositions herein is/are a buffer component/buffering agent(s) recognized in the art as buffer(s), such as those typically found in pharmaceutical formulations or, e.g., more specifically, ophthalmological compositions.

Ratios

According to aspects, any component(s) or compound(s)/agent(s) described herein can be present in composition(s) in therapeutically effective amount(s), compositionally compatible amount(s), or both. In aspects, any single component or compound/agent provided herein can be present in a relationship with, such as, e.g., in a ratio with, any one or more other single component or compound/agent. In aspects, any combination of component(s) or compound(s)/agent(s) provided herein can be present in a ratio with any other combination of component(s) or compound(s)/agent(s). In aspects, ratio(s) between such component(s) or compound(s)/agent(s) or combinations thereof can be established using any provided amount(s) for each disclosed herein, including, e.g., values within ranges of such amounts disclosed herein. To exemplify this disclosure, the following tables are provided. Table 1 below, e.g., illustrating a ratio array, demonstrates the types of ratios between components which the reader should understand to be encompassed by the disclosure herein. Table 2 below, also illustrating a ratio array, demonstrates types of ratios between agent(s)/constituent(s) which the reader should understand to be encompassed by the disclosure herein.

The reader should understand that the ratio arrays illustrated in Tables 1 and 2 are exemplary and do not necessarily disclose all possible ratios encompassed by this disclosure. For example, groups of such provided components can be, e.g., present in relationship to, e.g., as a ratio with, other one or more, e.g., groups, of provided components. For example, all excipients could be grouped and provided as a ratio to component(s), constituent(s), or groups of either or both component(s) and constituent(s), such as API(s). The arrays presented here, and, further, other such array(s) which could be generated by the disclosure herein (such as, e.g., between groups of component(s)/constituent(s)), should be interpreted as disclosing and encompassing any/all ratios which can be generated by the ranges for any such component(s)/constituent(s) provided here and elsewhere herein or which can be established using such disclosure (such as, e.g. when creating groups of components/constituents).

TABLE 1

Exemplary component ratios.

| | PCC | PEC | SLC | SPC | DMC | BFC | TNC | PVC | VTC | CLC | PAC | AXC | CRC |
|---|---|---|---|---|---|---|---|---|---|---|---|---|---|
| PCC | — | PEC:PCC | SLC:PCC | SPC:PCC | DMC:PCC | BFC:PCC | TNC:PCC | PVC:PCC | VTC:PCC | CLC:PCC | PAC:PCC | AXC:PCC | CRC:PCC |
| PEC | PCC:PEC | — | SLC:PEC | SPC:PEC | DMC:PEC | BFC:PEC | TNC:PEC | PVC:PEC | VTC:PEC | CLC:PEC | PAC:PEC | AXC:PEC | CRC:PEC |
| SLC | PCC:SLC | PEC:SLC | — | SPC:SLC | DMC:SLC | BFC:SLC | TNC:SLC | PVC:SLC | VTC:SLC | CLC:SLC | PAC:SLC | AXC:SLC | CRC:SLC |
| SPC | PCC:SPC | PEC:SPC | SLC:SPC | — | DMC:SPC | BFC:SPC | TNC:SPC | PVC:SPC | VTC:SPC | CLC:SPC | PAC:SPC | AXC:SPC | CRC:SPC |
| DMC | PCC:DMC | PEC:DMC | SLC:DMC | SPC:DMC | — | BFC:DMC | TNC:DMC | PVC:DMC | VTC:DMC | CLC:DMC | PAC:DMC | AXC:DMC | CRC:DMC |
| BFC | PCC:BFC | PEC:BFC | SLC:BFC | SPC:BFC | DMC:BFC | — | TNC:BFC | PVC:BFC | VTC:BFC | CLC:BFC | PAC:BFC | AXC:BFC | CRC:BFC |
| TNC | PCC:TNC | PEC:TNC | SLC:TNC | SPC:TNC | DMC:TNC | BFC:TNC | — | PVC:TNC | VTC:TNC | CLC:TNC | PAC:TNC | AXC:TNC | CRC:TNC |
| PVC | PCC:PVC | PEC:PVC | SLC:PVC | SPC:PVC | DMC:PVC | BFC:PVC | TNC:PVC | — | VTC:PVC | CLC:PVC | PAC:PVC | AXC:PVC | CRC:PVC |
| VTC | PCC:VTC | PEC:VTC | SLC:VTC | SPC:VTC | DMC:VTC | BFC:VTC | TNC:VTC | PVC:VTC | — | CLC:VTC | PAC:VTC | AXC:VTC | CRC:VTC |
| CLC | PCC:CLC | PEC:CLC | SLC:CLC | SPC:CLC | DMC:CLC | BFC:CLC | TNC:CLC | PVC:CLC | VTC:CLC | — | PAC:CLC | AXC:CLC | CRC:CLC |
| PAC | PCC:PAC | PEC:PAC | SLC:PAC | SPC:PAC | DMC:PAC | BFC:PAC | TNC:PAC | PVC:PAC | VTC:PAC | CLC:PAC | — | AXC:PAC | CRC:PAC |
| AXC | PCC:AXC | PEC:AXC | SLC:AXC | SPC:AXC | DMC:AXC | BFC:AXC | TNC:AXC | PVC:AXC | VTC:AXC | CLC:AXC | PAC:AXC | — | CRC:AXC |
| CRC | PCC:CRC | PEC:CRC | SLC:CRC | SPC:CRC | DMC:CRC | BFC:CRC | TNC:CRC | PVC:CRC | VTC:CRC | CLC:CRC | PAC:CRC | AXC:CRC | — |

Abbreviations: PCC (parasympathomimetic compound component); PEC (penetration enhancer component); SLC (solubilization component); SPC (combination solubilization/penetration enhancer component); DMC (demulcent component); BFC (buffer component); TNC (tonicity component); PVC (preservative component); VTC (viscosity/thickening enhancement component); CLC (chelation component); PAC (pH adjusting component); AXC (antioxidant component); CRC (carrier component).

TABLE 2

Exemplary constituent ratios.

|      | PIL | BKC | PS80 | CRM | TMT | MAN | GEL | BOR | CIT | ACE | PHS | NCL | CAR |
|------|-----|-----|------|-----|-----|-----|-----|-----|-----|-----|-----|-----|-----|
| PIL  | —   | BKC:PIL | PS80:PIL | CRM:PIL | TMT:PIL | MAN:PIL | GEL:PIL | BOR:PIL | CIT:PIL | ACE:PIL | PHS:PIL | NCL:PIL | CAR:PIL |
| BKC  | PIL:BKC | — | PS80:BKC | CRM:BKC | TMT:BKC | MAN:BKC | GEL:BKC | BOR:BKC | CIT:BKC | ACE:BKC | PHS:BKC | NCL:BKC | CAR:BKC |
| PS80 | PIL:PS80 | BKC:PS80 | — | CRM:PS80 | TMT:PS80 | MAN:PS80 | GEL:PS80 | BOR:PS80 | CIT:PS80 | ACE:PS80 | PHS:PS80 | NCL:PS80 | CAR:PS80 |
| CRM  | PIL:CRM | BKC:CRM | PS80:CRM | — | TMT:CRM | MAN:CRM | GEL:CRM | BOR:CRM | CIT:CRM | ACE:CRM | PHS:CRM | NCL:CRM | CAR:CRM |
| TMT  | PIL:TMT | BKC:TMT | PS80:TMT | CRM:TMT | — | MAN:TMT | GEL:TMT | BOR:TMT | CIT:TMT | ACE:TMT | PHS:TMT | NCL:TMT | CAR:TMT |
| MAN  | PIL:MAN | BKC:MAN | PS80:MAN | CRM:MAN | TMT:MAN | — | GEL:MAN | BOR:MAN | CIT:MAN | ACE:MAN | PHS:MAN | NCL:MAN | CAR:MAN |
| GEL  | PIL:GEL | BKC:GEL | PS80:GEL | CRM:GEL | TMT:GEL | MAN:GEL | — | BOR:GEL | CIT:GEL | ACE:GEL | PHS:GEL | NCL:GEL | CAR:GEL |
| BOR  | PIL:BOR | BKC:BOR | PS80:BOR | CRM:BOR | TMT:BOR | MAN:BOR | GEL:BOR | — | CIT:BOR | ACE:BOR | PHS:BOR | NCL:BOR | CAR:BOR |
| CIT  | PIL:CIT | BKC:CIT | PS80:CIT | CRM:CIT | TMT:CIT | MAN:CIT | GEL:CIT | BOR:CIT | — | ACE:CIT | PHS:CIT | NCL:CIT | CAR:CIT |
| ACE  | PIL:ACE | BKC:ACE | PS80:ACE | CRM:ACE | TMT:ACE | MAN:ACE | GEL:ACE | BOR:ACE | CIT:ACE | — | PHS:ACE | NCL:ACE | CAR:ACE |
| PHS  | PIL:PHS | BKC:PHS | PS80:PHS | CRM:PHS | TMT:PHS | MAN:PHS | GEL:PHS | BOR:PHS | CIT:PHS | ACE:PHS | — | NCL:PHS | CAR:PHS |
| NCL  | PIL:NCL | BKC:NCL | PS80:NCL | CRM:NCL | TMT:NCL | MAN:NCL | GEL:NCL | BOR:NCL | CIT:NCL | ACE:NCL | PHS:NCL | — | CAR:NCL |
| CAR  | PIL:CAR | BKC:CAR | PS80:CAR | CRM:CAR | TMT:CAR | MAN:CAR | GEL:CAR | BOR:CAR | CIT:CAR | ACE:CAR | PHS:CAR | NCL:CAR | — |

Abbreviations: PIL (pilocarpine compound(s)); BKC (benzalkonium chloride); PS80 (polysorbate 80); CRM (cremophor compound(s)); TMT (tromethamine); MAN (mannitol); GEL (gellan gum); BOR (borate buffer compound(s)); CIT (citrate buffer compound(s)); ACE (acetate buffer compound(s)); PHS (phosphate buffer compound(s)); NCL (sodium chloride (NaCl)); CAR (carrier).

Provided in Table 3 are exemplary amounts of exemplary component(s)/ingredient(s), which in aspects, can be/are present in composition(s) provided by the invention in a ratio with any one or more other component(s)/compound(s) disclosed, wherein such ratios can, in aspects, be a ratio formed by such disclosed amounts.

TABLE 3

Exemplary Ingredients and Exemplary Amounts from Which Ratio(s) Can be Derived

| Component/Compound Description | Exemplary Compound(s) (if component provided) | Exemplary Amount(s) (% w/v) |
|---|---|---|
| Parasympathomimetic compound component | Pilocarpine compound | 0.5-4 |
| Penetration enhancer component | Polysorbate 80, Benzalkonium chloride, Polyoxyl hydrogenated castor oil compound(s) | 0.005-5 |
| Solubilization Component | Polysorbate 80, Polyoxyl hydrogenated castor oil compound(s) | 0.05-5 |
| Combination solubilization/penetration enhancer component | Polysorbate 80 | 0.05-5 |
| Demulcent component | Polysorbate 80 | 0.01-5 |
| Buffer component | Acetate compound(s), Phosphate compound(s), citrate compound(s), borate compound(s) | 0.005-1.5 |
| Tonicity component | Sodium chloride, mannitol | 0.005-6 |
| Preservative component | Benzalkonium chloride | 0.0001-0.02 |
| Viscosity/thickening enhancement component | Gellan gum | 0.1-1 |
| Chelation component | EDTA compound(s) | 0.01-0.5 |
| pH adjusting component | Hydrochloric acid (HCl), Sodium hydroxide | Less than 0.1 |
| Antioxidant component | Ascorbate compound(s) | 0.001-2 |
| Carrier Component | Water | At least 60 |

TABLE 3-continued

Exemplary Ingredients and Exemplary Amounts from Which Ratio(s) Can be Derived

| Component/Compound Description | Exemplary Compound(s) (if component provided) | Exemplary Amount(s) (% w/v) |
|---|---|---|
| Pilocarpine compound(s) | Pilocarpine hydrochloride | 0.5-4 |
| Benzalkonium chloride | — | 0.0001-0.02 |
| Polysorbate 80 | — | 0.01-5 |
| Polyoxyl hydrogenated castor oil compound(s) | — | 0.05-0.8 |
| Tromethamine | — | 0.05-0.5 |
| Mannitol | — | 3-6 |
| Gellan gum | — | 0.1-1 |
| Borate buffer compound(s) | Boric acid | 0.5-1.5 |
| Citrate buffer compound(s) | Sodium citrate dihydrate | 0.005-0.09 |
| Acetate buffer compound(s) | Sodium acetate | 0.2-1.5 |
| Phosphate buffer compound(s) | Phosphoric acid | 0.005-1.5 |
| Sodium Chloride | — | 0.01-0.1 |
| Carrier | Water | At least 60 |

Note:
In aspects, values in Table 3 represent the amounts of each respective component/ingredient's representative percentage by weight/volume (% w/v) of the composition(s). In other aspects, values in Table 3 represent the amounts of each respective component/ingredient's representative percentage by weight/weight (wt. %) of the composition(s).

In aspects, composition(s) provided by the invention comprise a ratio of pilocarpine to buffer component of between about 1:0.001 and about 1:3, such as, e.g., about 1:0.6. Compositions can also be described by the inverse of any such ratio or similar ratio provided to characterize formulations of certain aspects in this disclosure.

In aspects, compositions provided by the invention comprise a ratio of pilocarpine compound to the buffer component of about 6:about 1-about 1:about 2, such as, e.g., about 2:1 or about 1:1, e.g., about 1.1:1, about 1.2:1, about 1.3:1, about 1.4:1, about 1.5:1, about 1.6:1, about 1.7:1, about 1.8:1, or about 1.9:1, e.g., about 1:1.9, about 1:1.8, about 1:1.7, about 1:1.6, about 1:1.5, about 1:1.4, about 1:1.3, about 1:1.2, or, e.g., ~1:1.1, such as, e.g., about 1.25:about 1. In aspects, compositions comprise pilocarpine and a buffer component, wherein the ratio of pilocarpine to the buffer component is no less than about 1.25:1. In aspects, compositions comprise pilocarpine and a buffer component, wherein the buffer component comprises a single buffer system, and the ratio of pilocarpine to the single buffer system is no less than about 1.25:1. In aspects, compositions comprise pilocarpine and buffer component, wherein the buffer component is characterizable as a reduced buffer content component (or, e.g., the composition is characterizable as a reduced buffer content composition), and the ratio of pilocarpine to the reduced buffer content component is no less than about 1.25:1. In aspects, compositions comprise pilocarpine and a buffer component, wherein the ratio of pilocarpine to the buffer component is greater than about 1:0.015. In aspects, compositions comprise pilocarpine and a buffer component, wherein the buffer component comprises a single buffer system, and the ratio of pilocarpine to the single buffer system is greater than about 1:0.015. In aspects, compositions comprise pilocarpine and buffer component, wherein the buffer component is characterizable as a reduced buffer content component (or, e.g., the composition is characterizable as a reduced buffer content composition), and the ratio of pilocarpine to the reduced buffer content component is greater than about 1:0.015.

In certain aspects, the ratio of the pilocarpine compound to borate compound(s) is no less than about 1.25:1. In aspects, the ratio of pilocarpine compound(s) to borate compound(s) is at least about 1.25:1. In aspects, compositions having such ratios comprise a single buffer component constituent. In aspects, the single buffer constituent is boric acid. In aspects, compositions provided by the invention comprise a ratio of pilocarpine compound to buffer component, e.g., borate compound(s), of between about 1:0.1 and about 1:4, such as, e.g., about 1:0.8.

In aspects, compositions provided by the invention comprise a ratio of pilocarpine compound to the buffer component of about 600:about 1-about 12:about 1, such as, e.g., about 200:1 or about 50:1, e.g., about 50:1 to about 60:1, e.g., about 51:1, about 52:1, about 53:1, about 54:1, about 55:1, about 56:1, about 57:1, about 58:1, or about 59:1. In aspects, compositions having such ratios comprise a single buffer component constituent. In aspects, the single buffer constituent is sodium citrate dihydrate. In aspects, compositions provided by the invention comprise a ratio of pilocarpine compound to buffer component, e.g., citrate compound(s), of between about 1:0.001 and about 1:0.2, such as, e.g., between about 1:0.01 and 1:0.02, as in, e.g., about 1:0.017 or about 1:0.018. In aspects, the ratio of pilocarpine to citrate compound(s), e.g., sodium citrate dihydrate, is at least about 1:0.015, such as, e.g., ≥~1:0.016 or at least about 1:0.017.

In aspects, compositions provided by the invention comprise a ratio of pilocarpine compound to the buffer component of about 1:about 1.5 to about 15:about 1, such as, e.g., about 1:1, about 2:1, about 3:1, about 7:1, about 10:1, or about 12:1, or, e.g., about 1.2:1, about 1.3:1, about 1.4:1, about 1.5:1, about 1.6:1, about 1.7:1, about 1.8:1, or about 1.9:1, such as between about 1.6:1 and about 1.7:1. In aspects, compositions having such ratios comprise a single buffer component constituent. In aspects, the single buffer constituent is an acetate buffer. In aspects, compositions provided by the invention comprise a ratio of pilocarpine compound to buffer component, e.g., acetate compound(s), of between about 1:0.05 and about 1:3, as in, e.g., about 1:0.1 to about 1:1.2, as in, e.g., about 1:0.6.

In aspects, compositions provided by the invention comprise a ratio of pilocarpine compound to benzalkonium chloride of about 1000:about 1-about 50:about 1, such as, e.g., about 50:1, about 150:1, about 330:1, about 400:1, or, e.g., about 100:1-about 200:1, about 120:1-about 1:190:1, e.g., about 140:1-about 1:180:1, or, e.g., about 150:1-about 180:1, such as, e.g., about 160:1-about 170:1, e.g., about 166:1 or about 167:1. In aspects, compositions comprise a ratio of BKC to pilocarpine compound(s) of between about 1:25 and about 1:40000, such as, e.g., between about 1:125 and about 1:12500, as in, e.g., about 1:100 to about 1:500, such as, e.g., about 1:100 to about 1:200, e.g., about 1:167.

In aspects, compositions provided by the invention comprise a ratio of benzalkonium chloride to a single buffer system of between about 1:25 and about 1:15000, such as, e.g., between about 1:50 and about 1:10000, as in, e.g., between about 1:50 and about 1:300, such as about 1:100 to about 1:200, as in for example between about 1:100 and about 1:150, such as about 1:133. In aspects, the ratio of benzalkonium chloride to a single buffer system, is greater than 1:100, such as, e.g., ≥~1:105, ≥~1:110, ≥~1:115, ≥~1:120, ≥~1:125, or, e.g., ≥~1:130. The single buffer compound in the single buffer system can be any of the buffers described herein, such as a buffer with a pKa of about 7-9, such as ~8, such as a boric acid buffer.

In aspects, compositions provided by the invention comprise a ratio of benzalkonium chloride to a single buffer system of between about 1:0.25 and about 1:900, such as, e.g., between about 1:0.5 and about 1:900, as in between about 1:1 and about 1:100 or between about 1:1 and about 1:50 or between about 1:1 and about 1:10, as in between about 1:1 and about 1:5 or between about 1:1 and about 1:3, such as, e.g., about 1:2 or about 1:3. In aspects, compositions comprise a ratio of benzalkonium chloride to a single buffer system of greater than about 1:2, such as, e.g., ≥~1:2.1, ≥~1:2.2, ≥~1:2.3, ≥~1:2.4, ≥~1:2.5, ≥~1:2.6, ≥~1:2.7, ≥~1:2.8, or ≥~1:2.9. The single buffer compound in the single buffer system can be any of the buffers described herein, such as a buffer with a pKa of about 3-4, e.g., a citrate buffer.

In aspects, compositions provided by the invention comprise a ratio of benzalkonium chloride to a single buffer system of between about 1:10 and about 1:15000, such as, e.g., between about 1:20 and about 1:15000, such as, e.g., between about 1:20 and about 1:500 or between about 1:20 and about 1:300, such as, e.g., about 1:50-about 1:200, as in, for example about 1:100. The single buffer compound in the single buffer system can be any of the buffers described herein, e.g., a buffer with a pKa of ~4-5 or about 4.5, e.g., an acetate buffer.

In aspects, compositions provided by the invention comprise a ratio of benzalkonium chloride to borate compound(s) of between about 1:25 and about 1:15000, such as, e.g., between about 1:50 and about 1:10000, as in, e.g., between about 1:50 and about 1:300, such as about 1:100 to about 1:200, as in for example between about 1:100 and about 1:150, such as about 1:133. In aspects, the ratio of benzalkonium chloride to borate compound(s), such as, e.g., boric acid, is greater than 1:100, such as, e.g., ≥~1:105, ≥~1:110, ≥~1:115, ≥~1:120, ≥~1:125, or, e.g., ≥~1:130.

In aspects, compositions provided by the invention comprise a ratio of benzalkonium chloride to citrate compound(s) of between about 1:0.25 and about 1:900, such as, e.g., between about 1:0.5 and about 1:900, as in between about 1:1 and about 1:100 or between about 1:1 and about 1:50 or between about 1:1 and about 1:10, as in between about 1:1 and about 1:5 or between about 1:1 and about 1:3, such as, e.g., about 1:2 or about 1:3. In aspects, compositions comprise a ratio of benzalkonium chloride to citrate compound(s), e.g., sodium citrate dihydrate, of greater than about 1:2, such as, e.g., ≥~1:2.1, ≥~1:2.2, ≥~1:2.3, ≥~1:2.4, ≥~1:2.5, ≥~1:2.6, ≥~1:2.7, ≥~1:2.8, or ≥~1:2.9.

In aspects, compositions provided by the invention comprise a ratio of benzalkonium chloride to acetate compound(s) of between about 1:10 and about 1:15000, such as, e.g., between about 1:20 and about 1:15000, such as, e.g., between about 1:20 and about 1:500 or between about 1:20 and about 1:300, such as, e.g., about 1:50-about 1:200, as in, for example about 1:100.

In aspects, compositions provided by the invention comprise a ratio of benzalkonium chloride to polysorbate 80 of about 1:0.5-about 1:50000, such, e.g., about 1:1-about 1:50000, about 1:1-about 1:30000, about 1:1-about 1:10000, about 1:1-about 1:5000, or about 1:1-about 1:1000, such as, e.g., about 1:1-about 1:500 or about 1:1-about 1:100, such as about 1:1-about 1:50, about 1:10-about 1:40, or about 1:20-about 1:40, such as about 1:30-about 1:35, e.g., about 1:33. In aspects, the ratio of benzalkonium chloride to polysorbate 80 is at least about 1:1. In aspects, the ratio of benzalkonium chloride to polysorbate 80 is greater than about 1:1, such as, e.g., ≥~1:5, ≥~1:10, ≥~1:15, ≥~1:20, ≥~1:25, ≥~1:30.

In aspects, benzalkonium chloride is present in compositions in an amount of between about 0.001% w/v, about 0.002% w/v, 0.003% w/v, 0.004% w/v, or 0.005% w/v and about 0.01% w/v, such as, e.g., between about 0.005% w/v and about 0.009% w/v, and ratios comprising benzalkonium chloride to one or more other constituent(s) of compositions (or, e.g., ratios comprising benzalkonium chloride to one or more other component(s) of compositions) is calculated according to such limitation(s).

In aspects, compositions provided by the invention comprise a ratio of pilocarpine compound(s) to polysorbate 80 of about 1:0.002 to about 1:10, such as, e.g., about 1:0.02-about 1:10, as in, e.g., 1:0.1-about 1:10, or, e.g., about 1:0.1-about 1:5, about 1:0.1-about 1:2, or about 1:0.1-about 1:1, such as, e.g., about 1:0.1-about 1:0.5, as in, for example, about 1:0.2.

In aspects, compositions provided by the invention comprise a ratio of borate compound(s) to polysorbate 80 of about 1:0.006 to about 1:10, such as, e.g., between about 1:0.006 and about 1:8, about 1:0.006 and about 1:6, about 1:0.006 and about 1:4, about 1:0.006 and about 1:2, or about 1:0.006 and about 1:1, such as, e.g., about 1:0.01-about 1:1, about 1:0.05-about 1:1, about 1:0.1-about 1:0.8, or, e.g., about 1:0.1-about 1:0.5, such as, e.g., about 1:0.25.

In aspects, compositions provided by the invention comprise a ratio of citrate compound(s) to polysorbate 80 of about 1:0.1-about 1:1000, such as, e.g., between about 1:0.1 and about 1:500, e.g., about 1:0.1-about 1:100, about 1:0.1-about 1:50, or, e.g., about 1:0.1-about 1:20, as in, e.g., about 1:1-about 1:15, about 1:10-about 1:15, or, e.g., about 1:11-about 1:12, such as about 1:11.4.

In aspects, compositions provided by the invention comprise a ratio of acetate compound(s) to polysorbate 80 of about 1:0.006-about 1:25, such as, e.g., about 1:0.006-about 1:20, about 1:0.006-about 1:15, about 1:0.006-about 1:10, or, e.g., about 1:0.006-about 1:5, such as, e.g., about 1:0.006-about 1:1 or about 1:0.006-about 1:0.5, such as, about 1:0.01-about 1:0.5 or about 1:0.1-about 1:0.5, such as for example about 1:0.33.

In aspects, compositions provided by the invention comprise a ratio of pilocarpine compound to penetration enhancer component of about 1:about 5 to about 60:about 1, e.g., about 1:4, about 1:3, about 1:2, about 1:1.5, about 1:1, about 2:1, such as for example about 2.5:1, or, e.g., about 3:1-about 10:1, such as, e.g., about 4:1 or for example about 5:1, e.g., about 10:1, about 20:1, about 30:1, about 40:1, about 50:1, or e.g., about 60:1, such as, e.g., about 4:1-about 13:1, e.g., ~4:1, ~5:1, about 8:1, about 10:1, about 12:1, or, e.g., ~13:1. In aspects, compositions comprise a ratio of pilocarpine compound(s) to penetration enhancer component of about 1:0.001 to about 1:10, such as, e.g., about 1:0.001-about 1:5, about 1:0.001-about 1:1, about 1:0.01-about 1:1, about 1:0.01-about 1:0.5, or, e.g., about 1:0.1-about 1:0.5, as in, e.g., about 1:0.1-about 1:0.4, about 1:0.1-about 1:0.3, or, e.g., about 1:0.1-about 1:0.25.

Additional Means/Steps for Performing Functions

In aspects, compositions provided by the invention comprise one or more means for performing one or more specific functions and methods of the invention include steps for performing functions. In general, any element described herein as a "means" for performing a function can also, wherever suitable, serve as a "step for" performing a function in the context of methods of the invention, and vice versa. E.g., a component described herein as a means for preserving a composition also simultaneously and implicitly supports a method of making such a composition comprising a step of preserving a composition and a kit comprising a means for delivering a composition implicitly and simultaneously provides a step for delivering the composition comprising the use of such delivery means.

In one aspect, compositions provided by the invention comprise means for enhancing penetration of one or more composition constituents, such means for penetration enhancement detectably or significantly improving the penetration into an eye tissue of one or more active pharmaceutical ingredients, e.g., PCC constituent, e.g., pilocarpine compound, e.g., salt of pilocarpine, e.g., pilocarpine hydrochloride ("penetration enhancement means"). Support for penetration enhancement means can be found in, e.g., the section entitled "Penetration Enhancer Component (Penetration Enhancer(s))."

In one aspect, compositions provided by the invention comprise means for solubilization of one or more composition constituents, such means for solubilization detectably or significantly improving the solubilization of one or more composition constituents, e.g., one or more active pharmaceutical ingredients, e.g., PCC constituent, e.g., pilocarpine compound, e.g., salt of pilocarpine, e.g., pilocarpine hydrochloride, detectably or significantly maintaining the solubilization of one or more composition constituents for a detectably or significantly longer period of time, or both ("solubilization means"). Support for solubilization means can be found in, e.g., the section entitled "Solubilization Component (Solubilizing Agent(s))."

In one aspect, compositions provided by the invention comprise means for solubilization of one or more composition constituents, such means for solubilization detectably or significantly improving the solubilization of one or more composition constituents, e.g., one or more active pharmaceutical ingredients, e.g., PCC constituent, e.g., pilocarpine compound, e.g., salt of pilocarpine, e.g., pilocarpine hydrochloride, detectably or significantly maintaining the solubilization of one or more composition constituents for a detectably or significantly longer period of time, or both, and, further, detectably or significantly improving the penetration into an eye tissue of one or more active pharmaceutical ingredients, e.g., PCC constituent, e.g., pilocarpine compound, e.g., salt of pilocarpine, e.g., pilocarpine hydrochloride ("penetration enhancement and solubilization means"). Support for penetration enhancement and solubilization means can be found in, e.g., the section entitled "Combination Solubilization/Penetration Enhancer Component (Solubilizing Agent(s)/Penetration Enhancer(s))."

In one aspect, compositions provided by the invention comprise means for soothing irritation caused by one or more composition constituents, such means for soothing detectably or significantly reducing or preventing irritation or inflammation caused by one or more composition constituents ("demulcent means"). Support for demulcent means can be found in, e.g., the section entitled "Demulcent Component (Demulcent(s))."

In aspects, compositions provided by the invention comprise a means of buffering a composition, such a means capable of maintaining the pH of compositions between about 3 to about 6 for an extended period of time, e.g., at least about 1 month, ~3 months, ~6 months, ~12 months, ~18 months, ~24 months, or, e.g., at least about 36 months when stored at room temperature. In certain aspects, compositions provided by the invention lack such a means of buffering pH ("buffering means"). In aspects, such buffering means are described in, e.g., the section entitled "Buffer Component (Buffer(s))."

In one aspect, compositions provided by the invention comprise means for providing a suitable tonicity of the composition(s), providing a suitable osmolality of the composition(s), e.g., means for providing composition(s) which do not cause detectable or significant ocular irritation due to tonicity when provided according to instructions ("tonicity means"). Support for tonicity means can be found in, e.g., the section entitled "Tonicity Component (Tonicity Agent(s))."

In one aspect, compositions provided by the invention comprise means for preserving the composition(s), e.g., detectably or significantly inhibiting microbial growth, detectably or significantly reducing the number of impurities or detectably or significantly improving the stability of the compositions such that compositions remain safe and suitable for administration after storage of at least about 1 month, e.g., ~2 months, or e.g., ~3 months or more after manufacturing at room temperature (25° C. and about 60% relative humidity) ("preservation means"). Support for preservation means can be found in, e.g., the section entitled "Preservative Component (Preservation Agent(s))."

In one aspect, compositions provided by the invention comprise means for increasing viscosity, such means for viscosity enhancement detectably or significantly increasing the thickness or viscosity of a composition, or, e.g., detectably or significantly modifying the nature of the composition such as, e.g., providing the composition as a gel ("viscosity enhancer means" or "thickening means"). Support for viscosity enhancer/thickening means can be found in, e.g., the section entitled "Viscosity Enhancer/Thickening Component (Viscosity Enhancing Agent(s)/Thickening Agent(s))."

In one aspect, compositions provided by the invention comprise means for chelation, such means for chelation detectably or significantly improving the stability of one or more active pharmaceutical ingredients, e.g., one or more PCC constituents, e.g., one or more pilocarpine compounds, e.g., a salt of pilocarpine, e.g., pilocarpine hydrochloride, detectably enhancing the effectiveness of one or more preservatives, or any combination thereof ("chelation means"). Support for chelation means can be found in, e.g., the section entitled "Chelation Component (Chelating Agent(s))."

In one aspect, compositions provided by the invention comprise means for adjusting the pH of the composition(s), providing a suitable or target pH of the composition(s) of between about, e.g., 3-about 6 ("pH adjusting means"). Support for pH adjusting means can be found in, e.g., the section entitled "pH Adjusting Component (pH Adjusting Agent(s)). In one aspect, compositions provided by the invention comprise means for protecting API(s) from oxidation, e.g., means for providing antioxidant protection of API(s), such means for antioxidant protection of API(s) detectably or significantly improving the stability of the one or more pilocarpine compound(s), detectably or significantly reducing impurities detected at time points 2 weeks, 1 months, 2 months, or 3 months or more (e.g., 6, 12, 18, 24, or 36 months) after manufacturing, or any combination thereof ("antioxidant means"). Support for antioxidant means can be found in, e.g., the section entitled "Antioxidant Component (Antioxidant(s))."

In one aspect, compositions provided by the invention comprise means for providing compositions of the invention as liquid compositions (e.g., solutions, gels, etc.), e.g., providing a carrier for the API(s) and any one or more other excipients of the composition(s) ("carrier means"). Support for carrier means can be found in, e.g., the section entitled "Carrier Component (Carrier Agent(s))."

Composition Characteristics

Lacking Borate Buffer, Citrate Buffer, or Both Borate & Citrate Buffer(s)

In certain specific aspects, compositions provided by the invention are characterizable as being free of boric acid, free of sodium citrate (e.g., sodium citrate dihydrate), or free of any borate buffer, citrate buffer, or any or all thereof. In particular, in aspects, the invention provides pharmaceutically acceptable and ophthalmologically suitable compositions comprising pilocarpine compound(s), e.g., pilocarpine HCl, wherein the composition is free of boric acid buffer(s). In other particular aspects, the invention provides pharmaceutically acceptable and ophthalmologically suitable compositions comprising pilocarpine compound(s), e.g., pilocarpine HCl, wherein the composition is free of citrate buffer(s). In still further particular aspects, the invention provides pharmaceutically acceptable and ophthalmologically suitable compositions comprising pilocarpine compound(s), e.g., pilocarpine HCl, wherein the composition is free of both boric acid buffer(s) and citrate buffer(s).

In one general aspect, the invention provides a pharmaceutically acceptable and ophthalmologically suitable composition comprising a pilocarpine compound and one or more pharmaceutically acceptable excipients, such as, e.g., one or more of a penetration-enhancer, preservative, chelating agent, tonicity agents, buffers or pH-adjusting agent, preservatives, and water, wherein the composition is free of boric acid or citrate buffers. In one aspect, the invention provides a pharmaceutically acceptable and ophthalmologically suitable ophthalmic composition comprising a pilocarpine compound and one or more pharmaceutically acceptable excipients, wherein the composition is free of boric acid or citrate buffers and maintains a pH of about 3 to about 6, such as, e.g., about 3.5 to about 5.5, about 4 to about 5, or about 4 to about 4.5, e.g., for a period of at least about 1 month under storage condition(s) described herein. In aspects, compositions comprise a single buffering agent, wherein the buffering agent is not a borate compound, is not a citrate compound, or is neither a borate or a citrate compound, and wherein the composition maintains a pH of about 3-6 for a period of at least about 1 month under such typical storage condition(s).

In a further specific aspect, the invention provides a pharmaceutically acceptable and ophthalmologically suitable ophthalmic composition comprising a pilocarpine compound, e.g., pilocarpine HCl, in a concentration of about 1 to 3% w/v, boric acid in a concentration of about 0.5% w/v to about 1.5% w/v, one or more tonicity agent(s) in a concentration of about 0.01% w/v to about 0.1% w/v, benzalkonium chloride in an amount of about 0.003% w/v to about 0.02% w/v or about 0.003%-less than about 0.01% w/v, water, and one or more buffers or pH-adjusting agents, wherein the composition is free of citrate buffer, e.g., free of sodium citrate. In another specific aspect, the invention provides a pharmaceutically acceptable and ophthalmologically suitable ophthalmic composition comprising a pilocarpine compound, e.g., a salt of pilocarpine, e.g., pilocarpine hydrochloride, in a concentration from about 1.0% w/v to 3.0% w/v, sodium citrate in a concentration from about 0.01% w/v to about 0.05%, one or more tonicity agent(s) in a concentration from about 0.1% w/v to about 0.5% w/v, benzalkonium chloride in an amount from about 0.003% to about 0.02% w/v, such as, e.g., about 0.003% to less than about 0.01% w/v, water, and one or more buffers or pH-adjusting agents, wherein the composition is free of boric acid. In certain aspects, such a composition can comprise sodium citrate dihydrate in an amount of about 0.01% w/v to about 0.05% w/v. In another specific aspect, the invention provides a pharmaceutically acceptable and ophthalmologically suitable ophthalmic composition comprising a pilocarpine compound, e.g., pilocarpine HCl, in a concentration of about 1.0% w/v to 3.0% w/v, optionally a penetration enhancer in a concentration from about 0.1% w/v to about 3.0% w/v, one or more tonicity agent(s) in a concentration of about 0.01% w/v to about 0.1% w/v, benzalkonium chloride in an amount from about 0.003% to about 0.02% w/v, water, and one or more buffers or pH-adjusting agents, wherein the composition is free of boric acid or citrate buffers. In aspects, a composition free of both a boric acid buffer and a citrate buffer comprises a buffer component comprising a single buffer constituent, such as, e.g., an acetate buffer.

In aspects, the invention provides a pharmaceutically acceptable and ophthalmologically suitable composition for treating an ocular condition comprising a pilocarpine compound, e.g., a salt of pilocarpine, e.g., pilocarpine hydrochloride, in an amount of about 1% w/v-about 3% w/v; a solubilization component in an amount of between about 0.1% w/v-about 0.7% w/v; a preservation component in an amount of about 0.003% w/v-about 0.02% w/v; a tonicity component in an amount of between about 3.5% w/v-about 5.5% w/v; and a viscosity enhancement component (thickening component) in an amount of about 0.1% w/v-about 1% w/v, wherein the composition is free of boric acid or citrate buffers. In aspects, the composition further comprises a buffer component, wherein the buffer component is free of boric acid or citrate buffers, however, comprises a single alternative buffer constituent, such as, e.g., an acetate buffer.

Ready-to Use (RTU)

In aspects, compositions provided by the invention are provided in ready-to-use (RTU) form, and do not require dilution or further modification prior to administration. In such compositions, the composition, in aspects, is stored in a healthcare setting, and is ready for immediate administration to a subject, such as a human patient. In such compositions, the composition, in aspects, is stored in a home setting, and is ready for immediate administration to a subject.

pH

As used herein, the term "pH" is the conventional measurement unit of hydrogen ion activity in a solution at room temperature (about 25° C.) unless another temperature is specified.

In aspects, compositions provided by the invention have a pH of about 3 to about 6, such as, e.g., ~3.5-~6, ~4-~6, or ~4.5-~6, e.g., ~3-~5.5, ~3-~5, or ~3-~4.5, such as, e.g., ~3.5-~5.5, ~4-~5, or, e.g., about 4 to ~4.5.

In aspects, the pH of the compositions provided by the invention, such as, e.g., pilocarpine compound compositions, will be affected by the concentration of each of the ingredients during manufacturing. Hence, in aspects, the pH of the compositions can be adjusted during the manufacturing to attain the target pH ranges described above, such as, e.g., ~3-~6, e.g., ~4-~5, or, e.g., ~4-~4.5.

Osmolality

In aspects, compositions provided by the invention are characterizable as isotonic. In aspects, compositions provided by the invention have an osmolality of between about 171 milliosmoles per kilogram (mOsm/Kg) and about 1171 mOsm/Kg, such as, e.g., ~171 mOsm/Kg-~1100 mOsm/Kg, ~171 mOsm/Kg-~1000 mOsm/Kg, ~171 mOsm/Kg-~900 mOsm/Kg, ~171 mOsm/Kg-~800 mOsm/Kg, ~171 mOsm/Kg-~700 mOsm/Kg, ~171 mOsm/Kg-~600 mOsm/Kg, ~171 mOsm/Kg-~500 mOsm/Kg, or ~171 mOsm/Kg-~400 mOsm/Kg.

In some aspects, compositions provided by the invention have an osmolality of between about 180 mOsm/Kg-about 1171 mOsm/Kg, such as, e.g., ~200 mOsm/Kg-~1171 mOsm/Kg, ~220 mOsm/Kg-~1171 mOsm/Kg, ~240 mOsm/Kg-~1171 mOsm/Kg, ~260 mOsm/Kg-~1171 mOsm/Kg, ~280 mOsm/Kg-~1171 mOsm/Kg, ~300 mOsm/Kg-~1171 mOsm/Kg, ~320 mOsm/Kg-~1171 mOsm/Kg, ~340 mOsm/Kg-~1171 mOsm/Kg, ~360 mOsm/Kg-~1171 mOsm/Kg, ~380 mOsm/Kg-~1171 mOsm/Kg, or, e.g., ~400 mOsm/Kg-~1171 mOsm/Kg, e.g., ~200 mOsm/Kg-~1000 mOsm/Kg.

In aspects, compositions provided by the invention have an osmolality of between about 200 mOsm/Kg and about 500 mOsm/Kg, or, e.g., between about 200 mOsm/Kg and about 400 mOsm/Kg, such as, e.g., ~250-~400 mOsm/Kg, ~260-~390 mOsm/Kg, ~270-~380 mOsm/Kg, or, e.g., ~280-~370 mOsm/Kg, for example ~210-~390 mOsm/Kg, ~220 ~380 mOsm/Kg, ~230-~370 mOsm/Kg, ~240-~360 mOsm/Kg, or, e.g., ~250-~350 mOsm/Kg. In aspects, the invention provides compositions comprising a tonicity agent component such that the composition comprises an isotonic range (e.g., an osmolality) within a range provided here.

Stability

Uncontradicted, the term "stable" or "stable composition" as used herein, refers to a pilocarpine compound composition provided by the invention having sufficient physical and chemical stability to allow storage at a convenient temperature, such as between about 0° C. and about 50° C., for a commercially reasonable period of time.

In aspects, compositions of the invention are stable. In aspects, compositions of the invention exhibit physical stability, chemical stability, or both, over any of the periods of storage described herein. The term "physical stability" typically refers to maintenance of color, dissolved oxygen level, head space oxygen level, and particulate matter, and the term "chemical stability" typically relates to formation of drug-related impurities in terms of total impurity, single maximum individual impurity, and maximum individual unknown impurity. For the purpose of the present invention chemical stability also includes maintenance of pH of the finished formulation. In aspects, compositions provided by the invention demonstrate stability required for commercially relevant times after manufacturing, such as for at least about 1, 3, 6, 9, 12, 18, 24 or 36 months, during which composition(s) is/kept in its/their original packaging under specified storage condition. The term "shelf life" refers to the amount of time the ophthalmic composition may be stored without detectable or significant loss of potency and/or dissolution profile. Preferably, the shelf life refers to the amount of time the ophthalmic composition may be stored without a loss of more than 2%, 5%, 8% or 10% of the potency and/or dissolution. Compositions of the invention, in aspects, exhibit such shelf-life characteristic. Herein, uncontradicted, the term "room temperature" refers to controlled room temperature of between about 15° C. and about 25° C.±2° C. Uncontradicted, disclosure directed to stability of compositions provided by the invention is described in terms of composition(s) stored under one or more storage condition(s) comprising a temperature of between about 15° C. and about 42° C. and a relative humidity of between about 35% and about 75% relative humidity, such as, e.g., about 15° C. to about 25° C.±2° C., about 25° C.±2° C. and about 40%±about 5% relative humidity, about 15° C.-about 27° C. and about 60% relative humidity, about 38° C.-about 42° C. and about 75% relative humidity, or any or all thereof.

In one aspect, the invention provides pharmaceutically acceptable and ophthalmologically suitable compositions comprising less than about 2.5% of total impurities, such as, e.g., ≤~2% total impurities, ≤~1.5%, ≤~1%, or ≤~0.5% total impurities. The term "impurity" refers to an undesired substance in a composition which may be present in an initial composition and/or may be formed after a certain period of shelf life of a composition. These impurities may, e.g., be formed via degradation of one or more components of the composition. Sources of degradation can include, but are not limited to, oxidation, light, ultraviolet light, moisture, heat, changes in pH, and composition component interactions.

In aspects, the invention provides compositions described herein, wherein the composition comprises less than about 2.5% total impurities, e.g., less than about 2%, less than about 1.5%, less than about 1%, or, e.g., less than about 0.5% total impurities after storage at a temperature of between about 15° C. and about 42° C. and a relative humidity of between about 35% and about 75% relative humidity, e.g., about 15° C.-about 27° C. and about 60% relative humidity, after storage at about 38° C.-about 42° C. and 75% relative humidity, or after storage under either/or any such condition, for a period of at least about 1 month, e.g., ≥~3 months, ≥~6 months, ≥~9 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

In one aspect, the invention provides pharmaceutically acceptable and ophthalmologically suitable compositions which remain stable and retain at least about 90%, such as, e.g., ≥~92%, ≥~94%, ≥~96%, ≥~98%, or even ≥~99% of the labelled concentration of pilocarpine compound, e.g., pilocarpine hydrochloride after storage under typical and/or accelerated conditions.

In aspects, the invention provides compositions as described herein, wherein the composition maintains at least about 98%, e.g., at least about 99%, of the pilocarpine compound when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/or any such condition, for at least about one month, such as, e.g., ≥~3 months, ≥~6 months, ≥~9 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

Dosage Forms & Administration Rates

In aspects, pharmaceutically acceptable and ophthalmologically suitable compositions provided by the invention can be provided as, e.g., formulated as, solutions, suspensions, ointments, gels, sprays, and other dosage forms suitable for topical ophthalmic administration. In some aspects, compositions provided by the invention are topically applied compositions. In some aspects, compositions provided by the invention are injectable compositions or are formulated to be suitable for administration by injection. In aspects, compositions provided by the invention can be suitable for topical delivery as drops or implantation in or on a subject's eye or tissue surrounding the eye, e.g., suitable for implantation into a subconjunctival space, naso-lacrimal duct, or vitreous body of the subject.

In aspects, compositions provided by the invention are aqueous solutions. In aspects, compositions provided as aqueous solutions provide ease of use of such compositions including as a patient's ability to easily administer such compositions by means of instilling a suitable dose of the solutions to affected eye(s). In aspects, aqueous compositions provided by the invention are typically more than about 50% w/v, e.g., ≥~55% w/v, ≥~60% w/v, ≥~65% w/v, ≥~70% w/v, ≥~75% w/v, ≥~80% w/v, ≥~85% w/v, or ≥~90% w/v water, and at least generally all, substantially all, or all components of the formulation are fully dissolved such that a clear, aqueous solution is provided.

In aspects, pharmaceutically acceptable and ophthalmologically suitable compositions provided by the invention are provided as a liquid solution, wherein compositions are administered as drops to affected eye(s). In aspects, compositions are administered as about 1 to about 3 drops, such as, e.g., about 1 to about 2 drops, e.g., about 1, about 2, or about 3 drops of the composition to each affected eye per dose/administration. Typically, a single administration comprises no more than about 2 drops of composition, such as about 1 or about 2 drops of composition per administration. In aspects, exact amounts to be administered can be determined by an overseeing physician, e.g., optometrist.

In certain aspects, pharmaceutically acceptable and ophthalmologically suitable compositions provided by the invention are provided as a gel. In aspects, compositions provided as a gel increase the amount of time the composition contacts eye tissue, leading to, in aspects, an increased bioavailability of active ingredient(s) contained therein.

According to certain aspects, pharmaceutically acceptable and ophthalmologically suitable compositions provided by the invention are controlled release compositions, such as, e.g., characterizable as slow-release compositions.

In some aspects, compositions are administered as a single administration. In other aspects, compositions are administered as a plurality of administrations, such as, e.g., 5, 10, 20, 30, 40, or 50 or more administrations, such as, e.g., daily administration for a period of days, weeks, months, or years (e.g., 1, 2, 3, 4, or 5 years or longer). In aspects, multiple administrations are separated from one another by a period of at least about 1 minute, such as at least about 30 minutes or longer, such as, e.g., at least about 1 hour or longer, or such as 24 hours or longer.

In aspects, an effective treatment period is a period of about 1 day, about 1 day-about 1 week, about 1 week to about 1 month, about 1 week to about 3 months, about 1 week to about 6 months, about 1 week to about 9 months, about 1 month to about 1 year, about 1 year to about 5 years, or longer. In certain aspects, compositions provided by the invention are used as a chronic treatment, e.g., in treating a chronic condition, such that the effective treatment period is an indefinite period of time (e.g., treatment is ongoing with no defined end point.)

The ophthalmic composition may be applied to each affected eye, both eyes, or the dominant eye of the recipient over the course of an effective treatment period. Exact application may vary depending on the target indication, the tolerance or goals of the recipient, the aim of the attending physician/treatment provider, or any combination thereof.

Methods of Use

Method of Improving Vision

In one aspect, the invention provides pharmaceutically acceptable and ophthalmologically suitable compositions comprising a pilocarpine compound and methods for their use in improving vision, reducing visual impairment, treating a vision-related ophthalmic condition, or combinations thereof. In aspects, compositions provided by the invention and methods of their use described herein can be provided to or for any patient in need thereof or suffering from a condition benefiting from the provision of compositions or methods described herein. In aspects, a suitable patient is a patient who wears corrective eyeglasses (spectacles) who cannot or will not use progressive lenses or bifocal lenses. In aspects, a suitable patient is a patient who has undergone cataract surgery. In aspects, a suitable patient is a patient who has developed presbyopia after a corneal procedure. In aspects, a suitable patient is a patient who has mono- or multi-focal intraocular lenses. In aspects, a suitable patient is a patient using contact lenses and does not tolerate mono-vision contact lenses. In aspects, a suitable patient is a patient using contact lenses and does not tolerate multi-focal contact lenses. In aspects, a suitable patient is a patient suffering from higher order aberration after corneal surgery. In aspects, a suitable patient is a patient suffering from hyperopia or tropias. In aspects, a suitable patient is a patient who does not tolerate a change in spectacle prescription or experiences rapid changes in spectacle prescription.

In aspects, compositions provided by the invention are suitable for administration to any subject benefiting from the administration thereof, e.g., any mammal with an ophthalmic condition benefitting from the receipt of a suitable amount of such compositions. In aspects, a suitable recipient is an adult human. In aspects, a suitable recipient is an adult human suffering from or diagnosed with, e.g., reduced vision, vision impairment, presbyopia, hyperopia, mydriasis, anisocoria, and accommodative esotropia, myopia, astigmatism (or symptoms related to, e.g., presbyopia, hyperopia, mydriasis, anisocoria, accommodative esotropia, myopia, or related to e.g., astigmatism), Adie's tonic pupil, or other causes of parasympathetic denervation, accommodative insufficiency, and complications arising after refractive surgery, such as decentered ablations following LASIK or PRK, corneal scars, hazing, refractive errors, etc. In aspects, compositions provided by the invention are suitable for administration to children. In aspects, compositions provided by the invention are not suitable for administration to children. In aspects, compositions provided by the invention are suitable for administration to children for whom other interventions are unsuitable, undesirable, or insufficient. Determinations of suitable and efficacy in such aspects can be determined by, e.g., scientific evidence, such as, for example, determination of bioequivalence to a product having such effects, or determination of such effectives through one or more scientific studies, such as one or more adequate, well-controlled, studies, which would be suitable for submission to U.S. FDA in connection with approval of a pharmaceutical product, wherein a suitably significant effect is observed.

Method of Modulating Physiological Properties of the Eye

In one aspect, the invention provides a method of detectably or significantly modulating one or more physiological properties of a mammalian eye comprising administering to the patient a pharmaceutically acceptable and ophthalmologically suitable ophthalmic composition comprising a pilocarpine compound, e.g., a salt of pilocarpine, e.g., pilocarpine hydrochloride, in a concentration of about 1.0% w/v to 3.0% w/v, optionally a penetration enhancer in a concentration from about 0.1% w/v to about 3.0% w/v, one or more tonicity agents in a concentration from about 0.01% w/v to about 0.1% w/v, benzalkonium chloride in an amount from about 0.003% to about 0.02% w/v, water, and one or more buffers or pH-adjusting agents, wherein the composition is free of boric acid buffers e.g., free of boric acid, free of citrate buffers, e.g., free of sodium citrate dihydrate, or free of both borate and citrate buffers.

In aspects, the invention provides a method of detectably or significantly modulating one or more physiological conditions of a mammalian eye comprising administering to the patient a pharmaceutically acceptable and ophthalmologically suitable ophthalmic composition comprising a pilocarpine compound, e.g., a salt of pilocarpine, e.g., pilocarpine hydrochloride, in an amount of about 1% w/v-about 3% w/v; a solubilization component in an amount of between about 0.1% w/v-about 0.7% w/v; a preservation component in an amount of about 0.003% w/v-about 0.02% w/v; a tonicity component in an amount of between about 3.5% w/v-about 5.5% w/v; and a viscosity enhancement component (thickening component) in an amount of about 0.1% w/v-about 1% w/v, wherein the composition is free of boric acid buffers e.g., free of boric acid, free of citrate buffers, e.g., free of sodium citrate dihydrate, or free of both borate and citrate buffers.

In aspects, a physiological property of a mammalian eye can be any physiological property participating in, affecting, contributing to, or otherwise associated with an ophthalmic condition treatable with the compositions herein, e.g., ocular conditions such as, e.g., reduced vision, presbyopia, hyperopia, mydriasis, anisocoria, accommodative esotropia, myopia, and, e.g., astigmatism.

Method of Treating an Ocular Condition

In aspects, efficacy of treatments (e.g., any efficacy of a method described herein) can be measured using any method known in the art. In certain aspects, measures of treatment can be assessed using e.g., as applicable to the target indication being treated, methods such as: (a) subjects having uncorrected distance and near visual acuity taken using a standard eye chart (e.g., Snellen chart at distance and Jaeger charts at near), or early treatment diabetic retinopathy study (ET-DRS) chart, wherein results can be converted to decimal notation using Halliday's conversion chart; (b) clinical evaluation of the depth of field obtained using standard wavefront aberrometry or other techniques in the art using modification/adjustment of spectacle prescription in refractor head/trial frame; (c) change in pupil size (as measured by infrared imaging system used for checking alignment during auto-refractometry); (d) pupil appearance (e.g., visual inspection for equality of size, shape, reactivity to light, direct and consensual accommodation); (e) non-invasive objective assessments of $3^{rd}$, $4^{th}$, and $5^{th}$ ocular higher order aberrations (e.g., coma, spherical aberration, and trefoil) conducted using standard wavefront aberrometry; or (f) other methods as appropriate and known in the art.

In one aspect, the invention provides a method of treating an ocular condition in a patient comprising administering to the patient an ophthalmic composition comprising a pilocarpine compound, e.g., a salt of pilocarpine, e.g., pilocarpine hydrochloride. In aspects, the invention provides methods for treating a patient diagnosed with any one or more such conditions.

Uncontradicted, "Treating" or "treatment" as used herein (and as well-understood in the art) can include any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure, etc.), fully or partially remove the disease's underlying cause, shorten a disease's duration, or a combination of any or all thereof.

In one aspect, the invention provides a method of treating an ocular condition comprising administering to the patient a pharmaceutically acceptable and ophthalmologically suitable ophthalmic composition comprising a pilocarpine compound, e.g., a salt of pilocarpine, e.g., pilocarpine hydrochloride, in a concentration of about 1.0% w/v to 3.0% w/v, optionally a penetration enhancer in a concentration from about 0.1% w/v to about 3.0% w/v, one or more tonicity agents in a concentration from about 0.01% w/v to about 0.1% w/v, benzalkonium chloride in an amount from about 0.003% to about 0.02% w/v, water, and one or more buffers or pH-adjusting agents, wherein the composition is free of boric acid buffers e.g., free of boric acid, free of citrate buffers, e.g., free of sodium citrate dihydrate, or free of both borate and citrate buffers.

In aspects, the invention provides a method of treating an ocular condition comprising administering to the patient a pharmaceutically acceptable and ophthalmologically suitable ophthalmic composition comprising a pilocarpine compound, e.g., a salt of pilocarpine, e.g., pilocarpine hydrochloride, in an amount of about 1% w/v-about 3% w/v; a solubilization component in an amount of between about 0.1% w/v-about 0.7% w/v; a preservation component in an amount of about 0.003% w/v-about 0.02% w/v; a tonicity component in an amount of between about 3.5% w/v-about 5.5% w/v; and a viscosity enhancement component (thickening component) in an amount of about 0.1% w/v-about 1% w/v, wherein the composition is free of boric acid buffers e.g., free of boric acid, free of citrate buffers, e.g., free of sodium citrate dihydrate, or free of both borate and citrate buffers.

The term "ocular condition" as used herein includes any condition, disease, or impairment which affects or involves the eye or one of the parts or regions of the eye, including optical conditions causing refractive errors in the eye. Uncontradicted, use of the term "ocular condition" includes one or more symptoms related to the composition, such as, e.g., symptom(s) related to presbyopia. Ocular conditions include, but are not limited to presbyopia, hyperopia, mydriasis, anisocoria, and accommodative esotropia, myopia, astigmatism, Adie's tonic pupil, or other causes of parasympathetic denervation, accommodative insufficiency, and complications arising after refractive surgery, such as decentered ablations following LASIK or PRK, corneal scars, hazing, refractive errors, etc. In aspects, compositions provided by the invention can be suitable for patients who have received cataract implants with intra-ocular implant lenses, laser eye surgery (laser-assisted in situ keratomileusis (LASIK), or implantation of a phakic intra-ocular implants. In aspects, compositions may be suitable in pediatric conditions, such as, e.g., squint in childhood, where eye surgery is not recommended.

In certain aspects, compositions provided by the invention may find use in the treatment of other conditions, such as, e.g., extreme skin conditions such as e.g., ichthyosis, multiple allergy syndrome, one or more conditions related to diabetes, etc.

Exemplary Target/Treatable Conditions

In aspects, the invention provides a method of treating presbyopia, including one or more symptom of presbyopia, the method comprising administering an effective amount of any one or more of the compositions described herein, for an effective treatment period, e.g., about 1 day to about 5 years or longer. In aspects, the degree or extent of presbyopia is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of presbyopia at the start of treatment (or, e.g., the degree of presbyopia present without treatment). In certain aspects, a single administration of a composition provided by the invention corrects presbyopia for a period of at least about 1 hours, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours. In aspects, such improvement is in a significant number of patients, as determined by one or more adequate and well-controlled clinical studies. This principle can be applied to any other clinical/therapeutic improvement/effect described in this disclosure.

In aspects, the invention provides a method of treating hyperopia, including one or more symptoms of hyperopia, the method comprising administering an effective amount of any one or more of the compositions described herein, for an effective treatment period, e.g., about 1 day to about 5 years or longer. In aspects, the degree or extent of hyperopia is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of hyperopia at the start of treatment (or, e.g., the degree of hyperopia present without treatment). In certain aspects, a single administration of a composition provided by the invention corrects hyperopia for a period of at least about 1 hours, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours.

In aspects, the invention provides a method of treating mydriasis, including one or more symptoms of mydriasis, the method comprising administering an effective amount of any one or more of the compositions described herein, for an effective treatment period, e.g., about 1 day to about 5 years or longer. In aspects, the degree or extent of mydriasis is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of mydriasis at the start of treatment (or, e.g., the degree of mydriasis present without treatment). In certain aspects, a single administration of a composition provided by the invention corrects mydriasis for a period of at least about 1 hours, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours.

In aspects, the invention provides a method of treating anisocoria, including one or more symptoms of anisocoria, the method comprising administering an effective amount of any one or more of the compositions described herein, for an effective treatment period, e.g., about 1 day to about 5 years or longer. In aspects, the degree or extent of anisocoria is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of anisocoria at the start of treatment (or, e.g., the degree of anisocoria present without treatment). In certain aspects, a single administration of a composition provided by the invention corrects anisocoria for a period of at least about 1 hours, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours.

In aspects, the invention provides a method of treating accommodative esotropia, including one more symptoms of accommodative esotropia, the method comprising administering an effective amount of any one or more of the compositions described herein, for an effective treatment period, e.g., about 1 day to about 5 years or longer. In aspects, the degree or extent of accommodative esotropia is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of accommodative esotropia at the start of treatment (or, e.g., the degree of accommodative esotropia present without treatment). In certain aspects, a single administration of a composition provided by the invention corrects accommodative esotropia for a period of at least about 1 hours, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours.

In aspects, the invention provides a method of treating myopia, including one or more symptoms of myopia, the method comprising administering an effective amount of any one or more of the compositions described herein, for an effective treatment period, e.g., about 1 day to about 5 years or longer. In aspects, the degree or extent of myopia is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of myopia at the start of treatment (or, e.g., the degree of myopia present without treatment). In certain aspects, a single administration of a composition provided by the invention corrects myopia for a period of at least about 1 hours, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours.

In aspects, the invention provides a method of treating astigmatism, including one or more symptoms of astigmatism, the method comprising administering an effective amount of any one or more of the compositions described herein, for an effective treatment period, e.g., about 1 day to about 5 years or longer. In aspects, the degree or extent of astigmatism is improved after a treatment period of at least about 24 hours, e.g., ≥~2 days, ≥~3 days, ≥~4 days, ≥~5 days, ≥~6 days, ≥~1 week, ≥~2 weeks, ≥~3 weeks, ≥~1 months, ≥~6 weeks, ≥~2 months, ≥~10 weeks, or ≥~3 months is about 95%, ~90%, ~85%, ~80%, ~75%, ~70%, ~60%, ~55%, ~50%, ~45%, ~40%, ~35%, ~30%, ~25%, ~20%, ~15%, or ~10% or even less than the degree of astigmatism at the start of treatment (or, e.g., the degree of astigmatism present without treatment). In certain aspects, a single administration of a composition provided by the invention corrects astigmatism for a period of at least about 1 hours, such as, e.g., ≥~2 hours, ≥~4 hours, ≥~6 hours, ≥~8 hours, ≥~10 hours, ≥~12 hours, ≥~14 hours, ≥~16 hours, ≥~18 hours, ≥~20 hours, ≥~22 hours, ≥~24 hours, ≥~26 hours, ≥~28 hours, ≥~30 hours, ≥~32 hours, ≥~34 hours, ≥~36 hours, ≥~38 hours, ≥~40 hours, ≥~42 hours, ≥~44 hours, ≥~46 hours, or ≥~48 hours.

In one aspect, the invention provides a pharmaceutically acceptable and ophthalmologically suitable composition comprising a pilocarpine compound, e.g., a salt of pilocarpine, e.g., pilocarpine HCl, for use in the treatment of an ocular condition (including one or more symptoms related to the ocular condition) selected from the group consisting of presbyopia, hyperopia, mydriasis, anisocoria, accommodative esotropia, myopia, and astigmatism, wherein (a) the composition is stable for a period of at least about 1 month, at least about 3 months, or at least about six months, (b) the ocular condition is improved by one or more measures of improvement known and accepted by the art for the condition being treated by at least about 15%, such as, e.g., at least about 20%, or, e.g., at least about 25% throughout (e.g., after the first, second, third, fifth, or, e.g., tenth administration of the composition, or at the end of the treatment period, and (c) wherein the composition is free of boric acid buffer, citrate buffer, or both.

Comparable or Improved Effects/Reduced Side Effects

In aspects, the invention provides a pharmaceutically acceptable and ophthalmologically suitable composition comprising a pilocarpine compound and being free of boric acid, citrate buffer (e.g., sodium citrate), or both, wherein treatment with the pharmaceutically acceptable and ophthalmologically suitable composition provides equivalent or detectably or significantly improved clinical outcomes in treating visual impairment (e.g., in improving vision) when compared to treatment with the product approved under U.S. Food and Drug Administration NDA Number 214028 (VUITY®) for the same or similar indication and for at least substantially the same administration period as determined by an appropriately conducted and powered clinical trial (one or more studies characterizable as adequate and well-controlled clinical trial(s) under applicable FDA standards).

In aspects, reference to or comparisons made to the product approved under U.S. Food and Drug Administration NDA Number 214028 refers to the product approved under this NDA number as of, e.g., Oct. 28, 2021, Dec. 28, 2021, Feb. 28, 2022, Apr. 28, 2022, Jun. 28, 2022, Aug. 28, 2022, Oct. 28, 2022, Dec. 28, 2022, or, e.g., Jan. 1, 2023. In other aspects, in making reference (e.g., a comparison) of composition(s) provided by the invention to products approved under FDA NDA number 214028, the comparison should be interpreted as extending to any product demonstrating or having demonstrated bioequivalence to a product approved under FDA NDA number 214028, as demonstrated by a study performed according to applicable FDA standards and/or recognized by an appropriate regulatory authority, such as the United States Food and Drug Administration. For example, herein when composition(s) of the invention are descried as providing equivalent or detectably or significantly improved clinical outcome(s) in treating visual impairment (e.g., in improving vision) when compared to treatment with the product approved under U.S. FDA NDA number 214028 for the same or similar indication and for at least substantially the same administration period as determined by an appropriately conducted and powered clinical trial (one or more studies characterizable as adequate and well-controlled clinical trial(s) under applicable FDA standards), the reader should interpret such comparison as inclusive of a comparison to a product/composition demonstrating or having demonstrated bioequivalence to a product approved under U.S. FDA NDA number 214028, as determined by an appropriately conducted and powered clinical trial performed under applicable FDA standards.

In aspects, the invention provides a method of reducing visual impairment (e.g., in improving vision) by providing to a patient in need thereof an effective amount of a composition described herein, wherein the method is clinically demonstrated to be as effective or detectably or significantly more effective than treatment with the product approved under U.S. Food and Drug Administration NDA Number 214028 (VUITY®) for the same or similar indication (e.g., reducing visual impairment) and for at least substantially the same administration period.

In aspects, the invention provides a pharmaceutically acceptable and ophthalmologically suitable composition comprising a pilocarpine compound and being free of boric acid, citrate buffer (e.g., sodium citrate), or both, wherein treatment with the pharmaceutically acceptable and ophthalmologically suitable composition provides equivalent or detectably or significantly improved clinical outcomes in treating presbyopia or one or more symptoms thereof when compared to treatment with the product approved under U.S. Food and Drug Administration NDA Number 214028 (VUITY®) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating presbyopia or one or more symptoms thereof by providing to a patient in need thereof an effective amount of a composition described herein, wherein the method is clinically demonstrated to be as effective or detectably or significantly more effective than treatment with the product approved under U.S. Food and Drug Administration NDA Number 214028 (VUITY®) for the same or similar indication (e.g., presbyopia) and for at least substantially the same administration period.

In aspects, the invention provides a pharmaceutically acceptable and ophthalmologically suitable composition comprising a pilocarpine compound and being free of boric acid, citrate buffer (e.g., sodium citrate), or both, wherein treatment with the pharmaceutically acceptable and ophthalmologically suitable composition provides equivalent or detectably or significantly improved clinical outcomes in treating hyperopia when compared to treatment with the product approved under U.S. Food and Drug Administration NDA Number 214028 (VUITY®) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating hyperopia by providing to a patient in need thereof an effective amount of a composition described herein, wherein the method is clinically demonstrated to be as effective or detectably or significantly more effective than treatment with the product approved under U.S. Food and Drug Administration NDA Number 214028 (VUITY®) for the same or similar indication (e.g., hyperopia) and for at least substantially the same administration period.

In aspects, the invention provides a pharmaceutically acceptable and ophthalmologically suitable composition comprising a pilocarpine compound and being free of boric acid, citrate buffer (e.g., sodium citrate), or both, wherein treatment with the pharmaceutically acceptable and ophthalmologically suitable composition provides equivalent or detectably or significantly improved clinical outcomes in treating mydriasis when compared to treatment with the product approved under U.S. Food and Drug Administration NDA Number 214028 (VUITY®) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating mydriasis by providing to a patient in need thereof an effective amount of a composition described herein, wherein the method is clinically demonstrated to be as effective or detectably or significantly more effective than treatment with the product approved under U.S. Food and Drug Administration NDA Number 214028 (VUITY®) for the same or similar indication (e.g., mydriasis) and for at least substantially the same administration period.

In aspects, the invention provides a pharmaceutically acceptable and ophthalmologically suitable composition comprising a pilocarpine compound and being free of boric acid, citrate buffer (e.g., sodium citrate), or both, wherein treatment with the pharmaceutically acceptable and ophthalmologically suitable composition provides equivalent or detectably or significantly improved clinical outcomes in treating anisocoria when compared to treatment with the product approved under U.S. Food and Drug Administration NDA Number 214028 (VUITY®) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating anisocoria by providing to a patient in need thereof an effective amount of a composition described herein, wherein the method is clinically demonstrated to be as effective or detectably or significantly more effective than treatment with the product approved under U.S. Food and Drug Administration NDA Number 214028 (VUITY®) for the same or similar indication (e.g., anisocoria) and for at least substantially the same administration period.

In aspects, the invention provides a pharmaceutically acceptable and ophthalmologically suitable composition comprising a pilocarpine compound and being free of boric acid, citrate buffer (e.g., sodium citrate), or both, wherein treatment with the pharmaceutically acceptable and ophthalmologically suitable composition provides equivalent or detectably or significantly improved clinical outcomes in treating accommodative esotropia when compared to treatment with the product approved under U.S. Food and Drug Administration NDA Number 214028 (VUITY®) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating accommodative esotropia by providing to a patient in need thereof an effective amount of a composition described herein, wherein the method is clinically demonstrated to be as effective or detectably or significantly more effective than treatment with the product approved under U.S. Food and Drug Administration NDA Number 214028 (VUITY®) for the same or similar indication (e.g., accommodative esotropia) and for at least substantially the same administration period.

In aspects, the invention provides a pharmaceutically acceptable and ophthalmologically suitable composition comprising a pilocarpine compound and being free of boric acid, citrate buffer (e.g., sodium citrate), or both, wherein treatment with the pharmaceutically acceptable and ophthalmologically suitable composition provides equivalent or detectably or significantly improved clinical outcomes in treating myopia when compared to treatment with the product approved under U.S. Food and Drug Administration NDA Number 214028 (VUITY®) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating myopia by providing to a patient in need thereof an effective amount of a composition described herein, wherein the method is clinically demonstrated to be as effective or detectably or significantly more effective than treatment with the product approved under U.S. Food and Drug Administration NDA Number 214028 (VUITY®) for the same or similar indication (e.g., myopia) and for at least substantially the same administration period.

In aspects, the invention provides a pharmaceutically acceptable and ophthalmologically suitable composition comprising a pilocarpine compound and being free of boric acid, citrate buffer (e.g., sodium citrate), or both, wherein treatment with the pharmaceutically acceptable and ophthalmologically suitable composition provides equivalent or detectably or significantly improved clinical outcomes in treating astigmatism when compared to treatment with the product approved under U.S. Food and Drug Administration NDA Number 214028 (VUITY®) for the same or similar indication and for at least substantially the same administration period as determined by an appropriately conducted and powered clinical (one or more studies characterizable as adequate and well-controlled clinical trial(s) under applicable FDA standards).

In aspects, the invention provides a method of treating astigmatism by providing to a patient in need thereof an effective amount of a composition described herein, wherein the method is clinically demonstrated to be as effective or detectably or significantly more effective than treatment with the product approved under U.S. Food and Drug Administration NDA Number 214028 (VUITY®) for the same or similar indication (e.g., astigmatism) and for at least substantially the same administration period.

In aspects, the invention provides a method of treating presbyopia including symptoms thereof, the method comprising administration of an effective amount of a composition described herein, wherein the method results in detectably or significantly reduced ocular blurring compared to treatment of presbyopia with the product approved under U.S. Food and Drug Administration NDA Number 214028 (VUITY®) for at least substantially the same administration period.

In aspects, the invention provides a method of treating presbyopia including symptoms thereof, the method comprising administration of an effective amount of a composition described herein, wherein the method results in detectably or significantly reduced ocular discomfort compared to treatment of presbyopia with the product approved under U.S. Food and Drug Administration NDA Number 214028 (VUITY®) for at least substantially the same administration period.

In aspects, the invention provides a method of treating presbyopia including symptoms thereof, the method comprising administration of an effective amount of a composition described herein, wherein the method results in detectably or significantly reduced eye pain compared to treatment of presbyopia with the product approved under U.S. Food and Drug Administration NDA Number 214028 (VUITY®) for at least substantially the same administration period.

In aspects, the invention provides a method of treating presbyopia including symptoms thereof, the method comprising administration of an effective amount of a composition described herein, wherein the method results in detectably or significantly reduced brow ache compared to treatment of presbyopia with the product approved under U.S. Food and Drug Administration NDA Number 214028 (VUITY®) for at least substantially the same administration period.

In aspects, the invention provides a method of treating presbyopia including symptoms thereof, the method comprising administration of an effective amount of a composition described herein, wherein the method results in detectably or significantly reduced blurry vision compared to treatment of presbyopia with the product approved under U.S. Food and Drug Administration NDA Number 214028 (VUITY®) for at least substantially the same administration period.

In aspects, the invention provides a method of treating presbyopia including symptoms thereof, the method comprising administration of an effective amount of a composition described herein, wherein the method results in detectably or significantly reduced light sensitivity compared to treatment of presbyopia with the product approved under U.S. Food and Drug Administration NDA Number 214028 (VUITY®) for at least substantially the same administration period.

In aspects, the invention provides a method of treating presbyopia including symptoms thereof, the method comprising administration of an effective amount of a composition described herein, wherein the method results in detectably or significantly reduced stinging compared to treatment of presbyopia with the product approved under U.S. Food and Drug Administration NDA Number 214028 (VUITY®) for at least substantially the same administration period.

In aspects, the invention provides a method of treating presbyopia including symptoms thereof, the method comprising administration of an effective amount of a composition described herein, wherein the method results in detectably or significantly reduced itching compared to treatment of presbyopia with the product approved under U.S. Food and Drug Administration NDA Number 214028 (VUITY®) for at least substantially the same administration period.

In aspects, the invention provides a pharmaceutically acceptable and ophthalmologically suitable ophthalmic composition of a pilocarpine compound, e.g., a salt of pilocarpine, e.g., pilocarpine HCl, free of boric acid, sodium citrate, or both, wherein treatment with the pharmaceutically acceptable and ophthalmologically suitable composition provides detectably or significantly reduced risk of poor illumination, retinal detachment, adhesions (synechiae) between the iris and the lens in patients who have iritis when using the composition, hypersensitivity, headache, conjunctival hyperemia, blurred vision, eye pain, visual impairment, eye irritation, lacrimation, or any combination thereof compared to treatment with the product approved under U.S. Food and Drug Administration NDA Number 214028 (VUITY®) for at least substantially the same administration period.

In aspects, the invention provides a pharmaceutically acceptable and ophthalmologically suitable ophthalmic composition of a pilocarpine compound, e.g., a salt of pilocarpine, e.g., pilocarpine HCl, free of boric acid, sodium citrate, or both, wherein treatment with the pharmaceutically acceptable and ophthalmologically suitable composition results in no detectable or significant impact on night vision, no detectable or significant reduction in visual field, or both.

In aspects, the invention provides compositions which detectably or significantly outperform the product approved under U.S. Food and Drug Administration NDA Number 214028 (VUITY®) in one or more respects related to composition pharmacokinetics. In aspects, compositions provided by the invention demonstrate a mean $C_{max} \geq 1.95$ ng/mL at day 30 of use. In aspects, compositions provided by the invention demonstrate a mean $AUC_{0-t,ss} \geq 4.14$ ng*hr/mL at day 30 of use. In aspects, compositions provided by the invention demonstrate a median $T_{max} \leq 0.3$ hours post dose at day 30 of use. In further aspects, the invention provides compositions wherein the proportion of patients gaining 3-lines or more in mesopic DCNVA, without losing more than 1 line (5 letters) of CDVA at Day 30, hour 3, is $\geq 26\%$.

In aspects, any composition described in this disclosure can be used in the methods described in this section. However, for purposes of exemplification, compositions according to Exemplary Formulation A, Exemplary Formulation B, Exemplary Formulation C, and Exemplary Formulation D of Examples 1 and 2 may be particularly suitable for use in such methods, such as, e.g., Compositions 1-7 of Examples 3 and 6.

Methods of Manufacturing

In one aspect, the invention provides a process for preparing a pharmaceutically acceptable and ophthalmologically suitable composition comprising a pilocarpine compound, e.g., a salt of pilocarpine, e.g., pilocarpine hydrochloride, in a concentration of about 1.0% w/v to 3.0% w/v, optionally a penetration enhancer in a concentration from about 0.1% w/v to about 3.0% w/v, one or more tonicity agents in a concentration from about 0.01% w/v to about 0.1% w/v, benzalkonium chloride in an amount from about 0.003% to about 0.02% w/v, water, and one or more buffers or pH-adjusting agents, wherein the composition is free of boric acid or citrate buffers (e.g., free of boric acid, free of sodium citrate, e.g., sodium citrate dihydrate, or free of both boric acid and sodium citrate, e.g., sodium citrate dihydrate.)

In aspects, the invention provides a process for preparing a pharmaceutically acceptable and ophthalmologically suitable composition comprising a pilocarpine compound, e.g., a salt of pilocarpine, e.g., pilocarpine hydrochloride, in an amount of about 1% w/v-about 3% w/v; a solubilization component in an amount of between about 0.1% w/v-about 0.7% w/v; a preservation component in an amount of about 0.003% w/v-about 0.02% w/v; a tonicity component in an amount of between about 3.5% w/v-about 5.5% w/v; and a viscosity enhancement component (thickening component) in an amount of about 0.1% w/v-about 1% w/v, water, and one or more buffers or pH-adjusting agents, wherein the composition is free of boric acid or citrate buffers (e.g., free of boric acid, free of sodium citrate, e.g., sodium citrate dihydrate, or free of both boric acid and sodium citrate, e.g., sodium citrate dihydrate.)

In aspects, compositions are prepared by using any suitable technique, many of which are known to those skilled in the art, the steps of which can be combined in any order. In describing methods of manufacturing provided by the invention, references to order of operations/steps may be present. It should be understood that steps of described manufacturing process(es) can be performed in any suitable order, provided that the end product is at least substantially, at least generally, or essentially the same.

According to certain aspects, the invention provides a method of manufacturing (e.g., a manufacturing process) for compositions described herein, wherein the process is a non-aseptic process, and wherein the method of manufacturing comprises a terminal sterilization step. In aspects, compositions are terminally sterilized using moist heat. Terminal sterilization can be used to destroy all viable microorganisms within the final, sealed container containing the pharmaceutical composition. In aspects, an autoclave is used to accomplish terminal heat-sterilization of compositions in their final packaging. Typical autoclave cycles in the pharmaceutical industry to achieve terminal sterilization of the final product are about 121° C. for at least about 10 minutes. In aspects, facilities, equipment, procedures, and personnel participating in the method of manufacturing, e.g., participating in the processing, meet GMP rules and guidelines for non-aseptic processes.

According to alternative aspects, the invention provides a method of manufacturing (e.g., a manufacturing process) for compositions described herein, wherein the process is an aseptic process. In aspects, sterility is maintained during the manufacturing process by use of sterile materials and a controlled working environment. In aspects, all containers and apparatus utilized in the process are sterilized, preferably by heat sterilization, prior to use, e.g., prior to filling. In aspects, a sterilized container is filled under aseptic conditions, such as by passing the composition through a filter. Therefore, in aspects, the compositions can be sterile filled into a container to avoid the heat stress of terminal sterilization. In aspects, facilities, equipment, procedures, and personnel participating in the method of manufacturing, e.g., participating in the processing, meet GMP rules and guidelines for aseptic processing.

In aspects, the invention provides a method of manufacturing a composition described herein, wherein the method comprises (a) preparation of a bulk composition, (b) offline filtration of the bulk composition, (c) online filtration of the bulk composition, and (d) final packaging of the composition. In aspects, composition(s) resulting from the method can be used in any one or more of the methods of treatment described herein.

In aspects, the invention provides a method of manufacturing a composition described herein, wherein the method comprises (a) preparation of a polymer phase, (b) preparation of a drug phase, (c) filtration of the drug phase into the polymer phase, (d) filtering the composition resulting from (c), and (e) final packaging of the composition. In aspects, composition(s) resulting from the method can be used in any one or more of the methods of treatment described herein.

In aspects, the invention provides pharmaceutically acceptable and ophthalmologically suitable compositions comprising pilocarpine compound(s), e.g., a salt of pilocarpine, e.g., pilocarpine HCl, and methods of their manufacture, wherein the composition resulting from the method of manufacturing is aseptically distributed into single dose or multidose containers. Further, in aspects, the invention provides packaging of such single or multidose containers into kits for distribution to an end user.

Specific examples of manufacturing process(es) suitable for manufacturing compositions provided by the invention are found in, e.g., Examples 4, 5, and 7 of this disclosure.

According to some aspects, the invention provides a first method of manufacturing a composition described herein comprising the following steps.

In aspects, the first step(s) in a manufacturing process comprises the preparation of a bulk solution.

In aspects, preparation of a bulk solution comprises, e.g., (a) collecting water, e.g., WFI, in a manufacturing vessel at a temperature of between about 65° C. to about 85° C., such as, e.g., about 70° C.-about 80° C., or, e.g., not less than about 70° C.; (b) cooling the water for injection to about 15° C. to about 30° C., such as about 20° C.-about 25° C.; and (c) bubbling 0.2 μm filtered nitrogen through the WFI and continuing to bubble 0.2 μm filtered nitrogen through the WFI until the dissolved oxygen content of the WFI is less than or equal to about 2 ppm, such as, e.g., ≤~1.5 ppm, ≤~1 ppm, or, e.g., ≤~0.5 ppm. In aspects, the manufacturing process comprises continuing to bubble 0.2 μm filtered nitrogen through the WFI during bulk solution manufacturing.

In aspects, preparation of the bulk solution is continued by transferring between about 50-about 70 Kg of WFI, e.g., about 60 Kg of WFI, into a separate holding vessel. In aspects, this reserved WFI can be used in other manufacturing steps, such as, e.g., the preparation of pH adjusting agents (such as, e.g., 0.1N hydrochloric acid, 0.1N sodium hydroxide, or both), and for, e.g., bringing the final composition up to a final target volume.

In aspects, bulk solution preparation can continue by mixing the WFI with a suitable mixing device/stirrer, set at a speed appropriate for attaining sufficient mixing. In aspects, mixing speed can be adjusted according to the vessel geometry and mixing/stirring dynamics exhibited by the solution/composition throughout manufacture.

In aspects, bulk solution preparation can continue by adding the required quantity of a preservation agent, e.g., benzalkonium chloride. In aspects, the container comprising the preservation agent, e.g., benzalkonium chloride to be added is rinsed one or more times, e.g., once, twice, three times, four times, or, e.g., five times, with a sufficient amount of WFI sufficient to rinse the container, e.g., an amount such as, e.g., about 30 mL to about 70 mL, or, e.g., about 50 mL each time. In aspects, mixing/stirring is continued during the addition of the rinse solution back into the vessel after each rinse.

In aspects, bulk solution preparation can continue by adding the required quantity of a penetration agent. In aspects, this step is omitted in the manufacturing process of a composition which does not comprise a penetration agent. In aspects, a penetration agent, such as, e.g., polysorbate 80, is added, and the container used to add the penetration agent, e.g., polysorbate 80, is rinsed one or more times, e.g., once, twice, three times, four times, or, e.g., five times, with an amount of WFI sufficient to rinse the container, e.g., an amount such as, e.g., about 30 mL to about 70 mL, or, e.g., about 50 mL each time. In aspects, mixing/stirring is continued during the addition of the rinse solution back into the vessel after each rinse.

In aspects, bulk solution preparation can continue by adding the required amount of buffer agent(s), such as, e.g., citrate buffer or borate buffer or, e.g., acetate buffer. In aspects, mixing/stirring is continued during the addition of the components, and is continued for a sufficient period of time to ensure the buffer constituents are completely dissolved, such as, for example, a period of time of, e.g., about 5 minutes, about 10 minutes, about 15 minutes, about 20 minutes, about 25 minutes, about 30 minutes, etc.

In aspects, bulk solution preparation can continue by adding the required amount of tonicity agent(s), such as, e.g., sodium chloride. In aspects, mixing/stirring is continued during the addition of the components and is continued for a sufficient period of time to ensure the buffer constituents are completely dissolved, such as, for example, a period of time of, e.g., about 5 minutes, about 10 minutes, about 15 minutes, about 20 minutes, about 25 minutes, or at least about 30 minutes or more.

In aspects, bulk solution preparation can continue by adding the required amount of PCC, such as, e.g., pilocarpine compound(s), e.g., salt(s) of pilocarpine, e.g., pilocarpine HCl, and the container used to add the PCC (e.g., pilocarpine HCl) is rinsed one or more times, e.g., once, twice, or three times with an amount of WFI sufficient to rinse the container, e.g., an amount such as, e.g., about 10 mL to about 40 mL, e.g., about 15-about 35 mL, or, e.g., about 25 mL each time. In aspects, mixing/stirring is continued during the addition of the rinse solution back into the vessel after each rinse. In aspects, mixing is continued for a sufficient period of time to ensure complete dissolution of the PCC, e.g., pilocarpine HCl, such as, e.g., a period of at least about 10 minutes, about 15 minutes, about 20 minutes, about 25 minutes, about 30 minutes, at least about 35 minutes, or, e.g., at least about 40 minutes or more.

In aspects, preparation of the bulk solution can continue by bringing the composition up to a target volume, e.g., a volume of about 85 L-95 L, such as, e.g., about 90 L. In aspects, the volume is brought up using WFI set aside as described above. In aspects, the solution is mixed for a sufficient period of time to ensure composition uniformity, such as, e.g., for a period of at least about 20 minutes, at least about 25 minutes, at least about 30 minutes, or at least about 35 minutes, e.g., about 30-32 minutes.

In aspects, preparation of the bulk solution can continue by performing a visual check of the solution for clarity, to ensure, e.g., that there are no visible undissolved particles in the solution.

In aspects, preparation of the bulk solution is pH adjusted using one or more pH adjusting agents. In aspects, pH of the solution is adjusted by the addition or one or more pH adjusting agents, with the solution sufficiently mixed after each addition such that the composition has a uniform pH prior to (a) sampling for pH, and (b) applying further pH adjustment as needed. In aspects, pH is adjusted to a pH of between about 4.4 to about 4.6, such as, e.g., about 4.4, about 4.5, or about 4.6 using the pH adjusting agent(s).

In aspects, preparation of the bulk solution is completed by bringing up the volume of the solution to a final volume of, e.g., about 100 L, with WFI reserved as described above. In aspects, the resulting solution is mixed for a sufficient period of time to ensure composition uniformity, such as, e.g., a period of at least about 10 minutes, at least about 15 minutes, at least about 20 minutes, at least about 25, or at least about 30 minutes. In aspects, a final pH check is performed to ensure that the composition pH is between about 4.4-about 4.6, such as, e.g., about 4.5.

In aspects, once the bulk solution is complete, offline filtration is performed. In aspects, the filtration is performed under laminar air flow.

In aspects, the second step(s) in a manufacturing process comprises the preparation of a bulk solution.

In aspects, after completion of the preparation of the bulk solution, the filtration process is initiated under controlled conditions, such as, e.g., under laminar air flow (LAF). In aspects, prior to initiation of the filtration process, a cartridge filter, e.g., a 0.2 μm capsule or cartridge filter, is integrity tested using an industry standard integrity test, such as, e.g., a water bubble point test, against the filter manufacturer's specification. In one aspect, an exemplary acceptable result is a pressure of not less than about 46 psi under a filtration pressure limit of between about 0.8 kg/cm$^2$ to about 1.8 kg/cm$^2$.

In aspects, prior to the start of filtration activity, the filtration unit is flushed with a sufficient amount of bulk solution to flush the unit, such as, e.g., about 200-250 mL, e.g., about 180 mL, about 200 mL, about 210 mL, about 220 mL, or e.g., about 230 mL of the bulk solution. In aspects, the bulk solution can be held inside of the filtration unit for a period of time during the flush, such as about 1.5 minutes, about 2 minutes, about 2.5 minutes, or about 3 minutes during the flush. In aspects, the bulk solution used for the flush is discarded after the flush. In aspects, the flushing procedure is repeated a number of times, such as one more time, two more times, three more times, four more times, or five or more times. In aspects, flushing is conducted a total of about 3 times.

In aspects, upon completion of flushing, filtration of the bulk solution is initiated. In aspects, the bulk solution is filtered through the pre-sterilized, tested, and flushed 0.2 μm capsule or cartridge filter. In aspects, all filtrate is collected in a sterile receiving vessel.

In aspects, upon completion of filtration, the filtrate within the sterile receiving vessel is overlayed with nitrogen, such as, e.g., 0.2 μm-filtered nitrogen.

In aspects, the receiving vessel can be transferred to a storage area, e.g., a sterile storage area, and stored under controlled conditions, e.g., controlled temperature and air flow conditions (e.g., under laminar air flow) until initiation of the filling activity.

In aspects, a post-filtration integrity test of the filter can be performed. In aspects, the post-filtration integrity test of the filter can be a water bubble point test. In aspects, an acceptable result is a pressure of not less than 39.2 psi under a filtration pressure limit of between about 0.8 kg/cm$^2$ to about 1.8 kg/cm$^2$.

In certain aspects, upon completion of the first filtration process is followed by a second filtration, wherein, prior to the initiation of filling and capping activity, the bulk solution is filtered through another filter, e.g., another 0.2μ pre-sterilized capsule or cartridge filter.

In aspects, pre-integrity filter testing is performed using an industry-accepted standard integrity test, such as, e.g., a water bubble point test, against the filter manufacturer's specification. In aspects, an acceptable result is a pressure of not less than about 46 psi under a filtration pressure limit of between about 0.8 kg/cm$^2$ to about 1.8 kg/cm$^2$. Upon passing the integrity test, in aspects the filter is then connected to the filling line through a pre-sterilized vessel, e.g., buffer tank.

In aspects, prior to the initiation of filtration activity, the filter/filtration unit is flushed with a sufficient volume of water to flush the filter, such as, e.g., about 200-about 250 mL of bulk solution, such as, e.g., about 180 mL, about 190 mL, about 200 mL, about 210 mL, about 220 mL, or, e.g., about 230 mL of the bulk solution. In aspects, the bulk solution is held within the filtration unit for a period of time during flushing, such as about 1.5 minutes, about 2 minutes, about 2.5 minutes, or, e.g., about 3 minutes, during this flushing process. In aspects, the flush and is then discarded. In aspects, the flushing process is repeated a number of times, such as at least one more time, at least two more times, at least 3 more times, at least four more times, or, e.g., at least five more times. In aspects, the flushing process is performed at least two additional times for a total of at least about 3 flushes, with the bulk solution used for flushing discarded after each flush.

In aspects, after discarding the filter flush solution, the entire quantity of remaining bulk solution is filtered into the sterile vessel, e.g., the sterile buffer tank.

In aspects, upon completing the filtration, the filling activity is then initiated. In aspects, upon the completion of the filling activity, a post-filtration integrity test of the filter is performed using an industry standard integrity test, such as, e.g., a water bubble point test. In aspects, an acceptable result is a pressure of not less than about 39.2 psi under a filtration pressure limit of between about 0.8 kg/cm$^2$ to about 1.8 kg/cm$^2$.

In aspects, the final step of a method of manufacturing composition(s) described herein is the process of filling and capping the composition(s).

In aspects, suitable sterile containers, such as, e.g., sterile vials, bottles such as, e.g., dropper bottles, are each filled to a target fill volume, such as, e.g., a volume of between about 1 mL and about 10 mL, such as a volume of between about 1 mL and about 5 mL, or, e.g., a volume of between about 1 mL and about 3 mL, such as a volume of about 2 mL to about 3 mL, e.g., a target volume of about 2.6 mL to about 2.8 mL (about 2.62 g to about 2.82 g), such as about 2.7 mL (about 2.72 g).

In aspects, after filling, the head space of each container is flushed with nitrogen, e.g., filtered nitrogen. In aspects, a minimum nitrogen flow is established, such as, e.g., a minimum nitrogen flow of about 1.5 L/min, about 2 L/min, about 2.5 L/min, or, e.g., about 3 L/min. In aspects, this step comprises placing associated container (e.g., vial, bottle, etc.), such as the nozzle of the bottle, and capping the bottle.

According to some aspects, the invention provides a second method of manufacturing a composition described herein comprising the following steps.

In aspects, a first ("filter number 1") and a second ("filter number 2") filter, e.g., 0.2 μm capsule filter, are each integrity-tested using an industry standard filter integrity test, e.g., a water bubble point test, against the filter manufacturer's specification(s). In aspects, an acceptable result of each test is a pressure of not less than about 46.0 psi under a filtration pressure limit of between about 0.8 kg/cm$^2$ to about 1.8 kg/cm$^2$. In aspects, upon completion of integrity testing, filters are flushed with a sufficient amount of nitrogen to remove any residual water from the filter pores.

In aspects, upon passing the integrity test, the outlet of filter number 2 is connected to the inlet of filter number 1 using a suitable connection mechanism, such as tubing, e.g., Pharma 50 silicone tubing, of a suitable length. Such length can be any suitable length for the manufacturing configuration, such as, e.g., a length of about 40 cm, about 50 cm, about 60 cm, about 70 cm, or about 80 cm. In aspects, the outlet of filter number 1 is connected to a valve, e.g., a diaphragm valve. In aspects, the inlet of filter number 2 is connected to a suitable connection mechanism, such as, e.g., tubing, for example Pharma 50 silicone tubing, of suitable length for the manufacturing configuration, such as, for example, a length of about 1.5 meters, 2 meters, 2.5 meters, 3 meters, or, e.g., about 3.5 meters, e.g., in aspects, about 2.30 meters. In aspects, the entire assembly is sterilized using a suitable sterilization method, e.g., autoclaving. During sterilization, e.g., while autoclaving, in aspects, the diaphragm valve is maintained in an open position. In aspects, upon completion of sterilization, e.g., after autoclaving, the diaphragm valve is closed under aseptic conditions. In aspects, the entire assembly is then connected to an empty manufacturing vessel (e.g., a "reactor vessel").

In aspects, the manufacturing vessel/reactor vessel is sterilized with a sufficient amount of water, e.g., water for injection (WFI), such as, e.g., about 100 Kg, about 110 Kg, about 120 Kg, about 130 Kg, about 140 Kg, or, e.g., about 150 Kg of WFI. In aspects, this establishes a sterilized "reactor vessel".

In aspects, a sufficient amount of WFI, e.g., about 120 Kg of WFI, at a temperature of not less than about 70° C., e.g., a temperature of between about 70° C.-about 80° C., is collected in a manufacturing vessel, such as, e.g., a stainless-steel (SS) manufacturing vessel.

In aspects, the WFI is cooled, for example to a temperature of about 20° C.-about 25° C., such as, e.g., by circulating the water through a water jacket. In aspect, while cooling, e.g., simultaneously with cooling, nitrogen, e.g., 0.2μ-filtered nitrogen, is passed (e.g., bubbled) through the WFI, with all WFI collected in the manufacturing vessel.

In aspects, the dissolved oxygen content of the WFI is tested one or more times, e.g., the WFI is routinely tested, to ensure that the WFI reaches a dissolved oxygen content of no more than about 2 ppm, e.g., no more than about 1.5 ppm, no more than about 1 ppm, or, e.g., no more than about 0.5 ppm.

In aspects, nitrogen bubbling is continued throughout the manufacturing process of one or more solutions of the method.

After completion of empty reactor sterilization, about 50 Kg, e.g., between about 50 Kg to about 70 Kg, of the about 120 Kg of WFI is transferred to a second manufacturing vessel, e.g., a stainless-steel manufacturing vessel. In aspects, this reserved WFI is used for one or more steps of the method, such as, e.g., used in the preparation of a drug phase, bringing composition(s) up to volume, or both, as is described further below.

In aspects, the establishment of a polymer phase is a first step(s) of the method of manufacturing.

In aspects, while maintaining the temperature of the remaining about 70 Kg (e.g., between about 50 to about 70 Kg) of WFI in the reactor vessel at about 70° C. to about 80° C., such as about 73° C. to about 78° C., a suitable stirrer (mixer) is established in the reactor vessel. In aspects, the suitable stirrer can be any stirrer suitable for the manufacturing configuration. In aspects, the stirrer/mixer is set to a stirrer speed of about 50 rpm to about 200 rpm, such as, e.g., about 75 rpm to about 175 rpm. In aspects, the mixing speed can be adjusted as necessary based on/according to the equipment being used in the manufacturing process, the batch volume, etc., e.g., according to the vessel geometry and the stirring dynamics during the manufacture of the batch.

In aspects, the required quantity of a viscosity enhancer component, e.g., a gelling agent, e.g., gellan gum NF (national formulary), is added to the reactor vessel. In aspects, stirring is maintained at a sufficient speed, e.g., about 125 rpm±about 50 rpm, for a sufficient time, e.g., for at least about 30 minutes, such as about 60 mins, or for a sufficient time to ensure complete dissolution of the gellan gum. In aspects, the solution is maintained at a temperature of between about 70° C. and about 80° C., such as, e.g., 73° C. and about 78° C., during the continuous stirring.

In aspects, after complete dissolution of the viscosity enhancer component, e.g., gellan gum, the solution is cooled to a temperature of between about 20° C. and about 25° C. In aspects, cooling is conducted under constant stirring. In aspects, this establishes the "polymer phase".

In aspects, the polymer phase is sterilized at set temperature, such as, e.g., a temperature of about 122.0° C., or a period of time, e.g., for at least about 20 minutes. In aspects, constant stirring continues during this period, e.g., at a suitable speed, such as a speed of about 125 rpm±about 50 rpm.

In aspects, upon completion of sterilization, the polymer phase is cooled, such as, e.g., to a temperature of about 20° C. to about 30° C., e.g., 25° C. In aspects, while cooling, when the temperature of the polymer phase reaches a set temperature, such as, e.g., a temperature of between about 50° C. to about 70° C., such as, e.g., about 60° C., the stirring speed is increased to a suitable increased mixing speed, e.g., a stirring speed of about 250 rpm±50 rpm.

In aspects, the method of manufacturing continues with a second step(s) of preparing a drug phase solution.

In aspects, an amount of reserved WFI, e.g., about 50 kg of the reserved, cooled WFI, is collected in a suitable manufacturing vessel. In aspects, a suitable stirrer/mixer is established in the manufacturing vessel. In aspects, the mixer is set to a suitable stirring speed for the manufacturing configuration being used, e.g., a stirring speed of, e.g., about 200 rpm to about 400 rpm, such as, e.g., about 250 rpm to about 350 rpm. In aspects, the mixing speed can be adjusted as necessary based on/according to the equipment being used in the manufacturing process, the batch size being manufactured, or both, e.g., according to the vessel geometry and the stirring dynamics during the manufacture of the batch.

In aspects, the total required quantity of PCC, e.g., pilocarpine compound(s), e.g., salt(s) of pilocarpine, e.g., pilocarpine HCl, is added to the manufacturing vessel, followed by the addition of the total required quantity of a preservative component, e.g., benzalkonium chloride. In aspects, the resulting composition is mixed for a sufficient period of time to ensure that the two components are completely dissolved.

In aspects, a penetration enhancer component constituent, if present in the composition, such as, e.g., polysorbate 80, is added to the manufacturing vessel. In aspects, the resulting composition is mixed for a sufficient period of time to ensure that the entire penetration enhancer component, e.g., polysorbate 80, is completely dissolved.

In aspects, upon the complete dissolution of the PCC (e.g., pilocarpine HCl), preservative component (e.g., benzalkonium chloride), and penetration enhancer component (e.g., polysorbate 80) (if present in the composition), a solubilization component constituent (such as, e.g., surfactant), e.g., cremophor, is added to the solution. In aspects, the resulting composition is mixed for a suitable period of time to allow the cremophor to completely dissolve.

In aspects, upon the complete dissolution of the solubilization constituent, e.g., cremophor, the total required quantity of a tonicity component, e g, mannitol, is added to the solution. In aspects, the resulting composition is mixed for a suitable period of time to allow the tonicity component, e.g., mannitol, to completely dissolve.

Upon the complete dissolution of the mannitol, the total required quantity of a second solubilizer, e.g., a solubilizer which in aspects may also be characterizable as a penetration enhancer, e.g., tromethamine, is added to the solution. In aspects, the resulting composition is mixed for a sufficient period of time to ensure complete dissolution of the component, e.g., tromethamine. In aspects, such a period of time can be, e.g., at least about 5 minutes, at least about 10 minutes, at least about 15 minutes, or, e.g., at least about 20 min.

In aspects, the composition is then checked for clarity. In aspects, clarity is evaluated using visual inspection. In aspects, stirring/mixing is continued until visual clarity of the solution is achieved.

In aspects, the volume of the composition is then brought to between about 50 L and about 60 L, e.g., to about 55 L (if, e.g., an exemplary batch size of about 100 L is being manufactured; it should be understood that this and other steps of the methods of manufacturing described here can be adjusted as needed for the batch size being manufactured) using, e.g., previously reserved WFI. In aspects, the composition is then stirred for a sufficient period of time to ensure composition uniformity, such as for at least about 5 minutes, at least about 10 minutes, at least about 15 minutes, at least about 20 minutes, at least about 25 minutes, or, e.g., at least about 30 minutes. In aspects, this establishes the "drug phase".

In aspects, an industry standard sampling protocol is used to sample and test the drug phase to ensure that the phase meets pre-established specification(s). Upon acceptance, in aspects, the drug phase is transferred to the sterilized polymer phase via aseptic filtration (see below).

In aspects, the method of manufacturing next comprises a step of aseptic filtration. As has been previously stated, references to order of operation, e.g., "next" as used here, should not be interpreted as limiting. In aspects, manufacturing steps/processes described can be performed in any suitable order provided the resulting composition comprises the characteristic(s) described herein.

In aspects, aseptic filtration of the drug phase into the sterile polymer phase is performed at a filtration pressure of between about, e.g., 0.8 Kg/cm$^2$-about 1.8 Kg/cm$^2$.

In aspects, prior to beginning the aseptic filtration, the weight of the drug phase is noted. In aspects, an amount of drug phase, e.g., about 50 Kg to about 60 Kg, e.g., about 55 Kg of the drug phase (which can be referred to as the "concentrated drug phase"), is filtered into the reactor vessel containing the polymer phase through the two sterilized 0.2 μm filters connected in series.

In aspects, WFI is passed through the filters a number of times, such as about two times or about three times with, e.g., between about 2 L and about 3 L of WFI used each time, such as, e.g., about 2.5 L of WFI each time. In aspects, the filtrate added to the reactor vessel each time to ensure all required drug phase is added into the reactor vessel. In aspects, the resulting composition is then stirred for a sufficient period of time (and at a suitable speed) to ensure composition uniformity. In aspects for example, the composition is mixed for at least about 45 minutes, at least about 50 minutes, at least about 55 minutes, at least about 60 minutes, at least about 65 minutes, at least about 75 minutes, at least about 80 minutes, or, e.g., at least about 85 minutes, such as, e.g., about 1 hour, at a suitable speed, such as, e.g., a speed of about 150 rpm-about 350 rpm, or, e.g., a speed of about 200 rpm to about 300 rpm, to ensure composition uniformity.

In aspects, a post-filtration integrity test of the filter is performed using an industry standard filter integrity test, e.g., a water bubble point test. In aspects, an acceptable result is a pressure of not less than about 34.8 psi under a filtration pressure limit of between about 0.8 kg/cm$^2$ to about 1.8 kg/cm$^2$.

In aspects, the composition is pH adjusted using one or more pH adjusting agents. In aspects, pH of the solution is adjusted by the addition or one or more pH adjusting agents, with the solution sufficiently mixed after each addition such that the composition has a uniform pH prior to (a) sampling for pH, and (b) applying further pH adjustment as needed. In aspects, pH is adjusted to a pH of between about 4.4 to about 4.6, such as, e.g., about 4.4, about 4.5, or about 4.6 using the pH adjusting agent(s).

In aspects, the method of manufacturing further comprises a final combined composition (bulk solution) filtration step.

In aspects, filtration of the final combined composition (bulk solution) is then performed using a suitable filter, e.g., such as an 8 μm filter, such as, e.g., an 8 μm PP2 MidiCap® filter (Sartorius).

In aspects, prior to initiating filtration activity, a sterilized filter, e.g., a sterilized 8.0 μm filter, e.g. a sterilized 8 μm polypropylene filter, is flushed with a sufficient amount of bulk solution, such as, e.g., about 80 mL to about 140 mL of bulk solution, e.g., about 100 mL to about 120 mL of bulk solution, a number of times such as about 2 times, about 3 times, about 4 times, or, e.g., about 5 times. In aspects, during each flush, the composition is held in the filtration unit for an extended period of time, such as about 1 minute, about 2 minutes, about 3 minutes, about 4 minutes, or, e.g., about 5 minutes, prior to discarding each flush. In aspects, upon completion of the flushing process, filtration of the bulk solution is performed. In aspects, the filtrate collected in a sterile receiving vessel.

In aspects, a final step of the method of manufacturing is filling and capping step(s).

In aspects, suitable sterile containers, such as sterile vials or, e.g., sterile bottles, such as, e.g., dropper bottles, are each filled to a suitable volume, such as, e.g., a volume of between about 1 mL and about 10 mL, such as, e.g., a volume of between about 1 mL and about 5 mL, e.g. about 1 mL to about 3 mL, or, e.g., a volume of about 2 mL to about 3 mL, such as, e.g., to a volume of between about 2.6 mL and about 2.8 mL (about 2.62 g to about 2.82 g), such as about 2.7 mL (about 2.72 g).

In aspects, after filling, the head space of each container, e.g., vial or bottle, is flushed with nitrogen, e.g., filtered nitrogen. In aspects, a minimum nitrogen flow is utilized for flushing, such as, e.g., a minimum nitrogen flow of about 1 L/min, about 1.5 L/min, about 2 L/min, about 2.5 L/min, or, e.g., about 3 L/min. In aspects, this step comprises placing all container components, e.g., a bottle nozzle, and capping the bottle.

Product-by-Process Aspects

In aspects, the invention provides compositions comprising about 1% w/v-about 3% w/v of a pilocarpine compound, e.g., a salt of pilocarpine, e.g., pilocarpine HCl, about 0.003% w/v-about 0.02% w/v benzalkonium chloride, about 0.5% w/v-about 1.5% w/v boric acid or, alternatively, about 0.005% w/v-about 0.09% w/v sodium citrate dihydrate, or, as yet a third alternative, not comprising either boric acid or sodium citrate dihydrate, about 0.01% w/v-about 0.1% w/v sodium chloride, optionally about 0.05% w/v-about 0.5% w/v of a penetration enhancer such as, e.g., polysorbate 80, a sufficient amount of pH adjusting agent(s) to establish the pH of the composition at between about 3.5-about 5.5, and water, the composition made by a process comprising (a) preparing a bulk composition, (b) offline filtering the bulk composition, (c) online filtering the bulk composition, and (d) packaging of the final composition, wherein the process is either an aseptic process or a non-aseptic process.

In aspects, the invention provides compositions comprising between about 0.5% w/v-about 2.5% w/v of a pilocarpine compound, e.g., a salt of pilocarpine, e.g., pilocarpine HCl, about 0.05% w/v-about 0.8 w/v of a polyethoxylated castor oil (e.g., cremophor), about 0.003% w/v-about 0.02% w/v of benzalkonium chloride, about 0.05% w/v-about 0.5% w/v tromethamine, about 3% w/v-about 6% w/v mannitol, about 0.1% w/v-about 1% w/v gellan gum, a sufficient amount of pH adjusting agent(s) to establish the pH of the composition at between about 3.5-about 5.5, and water, the composition made by a process comprising (a) preparing a polymer phase, (b) preparing a drug phase, (c) filtering the drug phase into the polymer phase, (d) filtering the composition resulting from (c), and (e) packaging the final composition, wherein the process is either an aseptic process or a non-aseptic process. In aspects, the process is an aseptic process.

In aspects, the invention provides compositions comprising about 1% w/v-about 3% w/v of a PCC, e.g., a pilocarpine compound, e.g., a salt of pilocarpine, e.g., pilocarpine HCl, about 0.003% w/v-about 0.02% w/v of a preservation agent, about 0.5% w/v-about 1.5% w/v borate buffer or, alternatively, about 0.005% w/v-about 0.09% w/v citrate buffer, or, as yet a third alternative, not comprising either borate buffer (e.g., not comprising boric acid) or citrate buffer (e.g., not comprising sodium citrate dihydrate), about 0.01% w/v-about 0.1% w/v tonicity component, optionally about 0.05% w/v-about 0.5% w/v of a penetration enhancer such as, e.g., polysorbate 80, a sufficient amount of pH adjusting agent(s) to establish the pH of the composition at between about 3.5-about 5.5, and a carrier, e.g., an aqueous carrier such as WFI, the composition made by a process comprising (a) preparing a bulk composition, (b) offline filtering the bulk composition, (c) online filtering the bulk composition, and (d) packaging of the final composition, wherein the process is either an aseptic process or a non-aseptic process, and, further, wherein the composition (a) maintains a pH of about 3 to about 5, e.g., about 4 to about 5, (b) retains at least about 95%, such as, e.g., at least about 97%, about 98%, or, e.g., at least about 99% of the original PCC when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/any such condition, (c) comprises less than about 2.5% total impurities, e.g., less than about 2%, less than about 1.5%, less than about 1%, or, e.g., less than about 0.5% total impurities after storage under conditions comprising a temperature of between about 15° C. and about 42° C. and a relative humidity of between about 35% and about 75% relative humidity, e.g., at about 15° C.-about 27° C. and about 60% relative humidity, after storage at about 38° C.-about 42° C. and 75% relative humidity, or after storage under either/any such condition, or (d) any combination of or all of (a), (b), and (c) for a period of at least about 1 month, such as, e.g., ≥~3 months, ≥~6 months, ≥~9 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

In aspects, the invention provides compositions comprising between about 0.5% w/v-about 2.5% w/v of a PCC, e.g., a pilocarpine compound, e.g., a salt of pilocarpine, e.g., pilocarpine HCl, about 0.05% w/v-about 0.8 w/v of a first solubilizer, e.g., a surfactant solubilizer (e.g., cremophor), about 0.003% w/v-about 0.02% w/v of a preservation component, about 0.05% w/v-about 0.5% w/v a second solubilizer, e.g., a solubilizer further characterizable as a penetration enhancer, about 3% w/v-about 6% w/v tonicity component, about 0.1% w/v-about 1% w/v thickening component, a sufficient amount of pH adjusting agent(s) to establish the pH of the composition at between about 3.5-about 5.5, and water, the composition made by a process comprising (a) preparing a polymer phase, (b) preparing a drug phase, (c) filtering the drug phase into the polymer phase, (d) filtering the composition resulting from (c), and (e) packaging the final composition, wherein the process is either an aseptic process or a non-aseptic process, e.g., an aseptic process, and, further, wherein the composition (a) maintains a pH of about 3 to about 5, e.g., about 4 to about 5, (b) retains at least about 95%, such as, e.g., at least about 97%, about 98%, or, e.g., at least about 99% of the original PCC when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/any such condition, (c) comprises less than about 2.5% total impurities, e.g., less than about 2%, less than about 1.5%, less than about 1%, or, e.g., less than about 0.5% total impurities after storage at a temperature of between about 15° C. and about 42° C. and a relative humidity of between about 35% and about 75% relative humidity, e.g., at about 15° C.-about 27° C. and about 60% relative humidity, after storage at about 38° C.-about 42° C. and 75% relative humidity, or after storage under either/any such condition, or (d) any combination of or all of (a), (b), and (c) for a period of at least about 1 month, such as, e.g., ≥~3 months, ≥~6 months, ≥~9 months, ≥~12 months, ≥~14 months, ≥~16 months, ≥~18 months, ≥~20 months, ≥~22 months, ≥~24 months, ≥~26 months, ≥~28 months, ≥~30 months, ≥~32 months, ≥~34 months, or, e.g., ≥~36 months.

Packaging/Delivered Form and Kits

In aspects, compositions provided by the invention can be provided with, e.g., contained within, a delivery device suitable for administering the composition. In aspects, such a delivery device can be any suitable delivery device capable of maintaining the compositions therein in sterile form prior to administration and, further, capable of preventing detectable or significant degradation of the compositions during shipping or storage. In aspects, compositions can be provided with, e.g., contained within, dropper bottle(s), squeeze bottle(s), vials, and the like which are commonly known in the art.

According to certain embodiments, pharmaceutically acceptable and ophthalmologically suitable compositions provided by the invention can be packaged in any suitable packaging, such suitability being at least in part defined by protecting the compositions held therein from degradation, contamination, or both. In certain aspects, suitable packaging materials are materials which exhibit less than about 20%, such as <~18%, <~16%, <~14%, <~12%, <~10%, <~8%, <~6%, <~4%, <~2% or even less sorption of a PCC constituent, such as, e.g., a pilocarpine compound, or more specifically pilocarpine HCl. In some respects, suitable materials include but may not be limited to packaging material made of select polyolefins, such as, e.g., DuPont® 20 LDPE, Chevron 5502 HDPE, Atofina 3020 PP, polypropylene homopolymers, low ethylene content (<8%) polypropylenes, and polymers (HDPE, PP) with low content of additives (<5%) and with low flexural modulus (<200 kpsi). In some respects, a suitable material is an EP-quality LDPE which, in further aspects, may contain no additives. In aspects, suitable packaging can comprise a polypropylene container provided that that polypropylene container is not packaged in a bag/container containing an iron oxide oxygen scavenger.

In certain aspects, the packaging can comprise or can be mostly comprised of (e.g., comprise in an amount ≥~10%, ≥~20%, ≥~30%, ≥~40%, or ≥~50%, such as, e.g., comprise in an amount ≥~60%, ≥~70%, ≥~80%, ≥~90% or more) an ultraviolet-light blocking agent or material. In aspects, such a material can be capable of blocking ≥~1%, ≥~5%, ≥~10%, ≥~20%, ≥~30%, ≥~40%, or ≥~50%, such as, e.g., ≥~60%, ≥~70%, ≥~80%, ≥~90% or more of the ultraviolet light in the environment from entering the container. In aspects, compositions described herein can be packaged in, stored, in, or both packaged and stored in a container wherein the container significantly reduces exposure of the composition to UV B radiation, such as by at least about 50%, at least about 65%, at least about 75%, at least about 90%, at least about 95%, or at least 99%. In some aspects, the packaging material of a composition described herein is semi- or completely opaque, while in alternative aspects, the packaging is semi- or completely clear. In aspects, packaging can comprise different parts wherein one component of the packaging comprises a first material and one or more components of the packaging contain a second (or more) material(s).

In certain aspects, packaging can be selected based on the method of delivery of the compositions herein (e.g., compositions provided as a gel can be provided in suitable packaging for gels wherein compositions provided as a liquid can be provided in suitable packaging for liquids, e.g., in a user-friendly dropper bottle; in aspects, a composition in gel form can also or alternatively be provided in a dropper bottle for drop-by-drop administration.) In aspects, the compositions provided by the invention are stored in vials capable of being penetrated by a needle such that compositions can be extracted from such vials and administered by injection. In aspects, compositions are provided in pre-filled injection devices, such as, e.g., pre-filled syringes. In aspects, the compositions of the invention are stored in a packaging that facilitates the delivery of the composition as eye drops.

In one aspect, ophthalmic compositions provided by the invention comprise a pilocarpine compound, e.g., pilocarpine hydrochloride, and one or more pharmaceutically acceptable excipient(s), and are provided in single-dose bottles. In an alternative aspect, such compositions are provided in multi-dose bottles, such as multi-dose eye dropper bottles. In aspects, such multi-dose bottles allow for the composition, e.g., provided as a solution to be dropped into the recipient's eye(s), to be applied as liquid drops over a course of treatment, such as, e.g., over the course of many days, several weeks, months, or longer.

In aspects, the average force required to release one or more drops of the compositions described herein from a dropper bottle (a standard bottle common in the art for dispensing liquid in droplet form), by compressing the middle section of the storage body of such a dropper bottle, ranges between about 1.7-2.8 Kg for release of the first drop, e.g., between about 1.7-2.6, ~1.7-2.4, ~1.7-2.2, or between about ~1.7-2.0 Kg. In aspects, successive drops can require more tension, such as can require an additional ~20-30% of force for release of the second drop, and, e.g., an additional force of ~24-50% for release of the third drop.

In some aspects, compositions provided by the invention are administered by injection. In aspects, compositions are provided in packaging which is accessible via a needle such that compositions can be withdrawn by a needle in preparation for injection. In aspects, compositions are provided in pre-filled injection devices, such as pre-filled syringes. In aspects, one or more pre-filled syringes are provided in a kit as is described further elsewhere herein. In aspects, injection devices can comprise between about 0.25 mL-about 5 mL of composition, though typically up to about 1 mL, such as, e.g., between ~0.5-~5 mL, ~0.75-~5 mL, ~1-~5 mL, ~1.25-~5 mL, ~1.5-~5 mL, ~1.75-~5 mL, ~2-~5 mL, ~2.25-~5 mL, ~2.5-~5 mL, ~2.75-~5 mL, ~3-~5 mL, ~3.25-~5 mL, ~3.5-~5 mL, ~3.75-~5 mL, ~4-~5 mL, ~4.25-~5 mL, ~4.5-~5 mL, or, e.g., ~4.75-~5 mL, such as for example ~0.25-~4.5 mL, ~0.25-~4 mL, ~0.25-~3.5, ~0.25-~3.5 mL, ~0.25-~3 mL, ~0.25-~2.5 mL, ~0.25-~2 mL, ~0.25-~1.5 mL, or, e.g., ~0.25-~1 mL of composition, as in, e.g., ~0.1 mL, ~0.15 mL, ~0.2 mL, ~0.25 mL, ~0.3 mL, ~0.35 mL, ~0.4 mL, ~0.45 mL, ~0.5 mL, ~0.55 mL, ~0.6 mL, ~0.7 mL, ~0.75 mL, ~0.8 mL, ~0.85 mL, ~0.9 mL, or, e.g., ~1 mL of composition.

In aspects, compositions provided by the invention are provided in single dose or multi-dose packaging.

In aspects, a single dose package comprises a single dose of composition within a single dose administration container. In aspects, a multi-dose package comprises a plurality of single dose administration containers. In aspects, a multi-dose package comprises a plurality of doses within a single administration container. For example, a multi-dose package can be, e.g., a single dropper bottle comprising sufficient volume of composition to administer the composition multiple times over the course of an administration period, such as (but certainly not limited to) administration of about 1-3×/day over a period of about 1-7 days, ~1 week-~1 month, ~1 month-~3 months, ~3 months-~6 months, or, e.g., ~6 months-~1 year.

In aspects, packaging of compositions is any suitable packaging which effectively provides compositions with a shelf life of at least about 1 month, such as, e.g., ≥~3 weeks, ≥~4 weeks (1 month), ≥~5 weeks, ≥~6 weeks, ≥~7 weeks, ≥~8 weeks (2 months), ≥~9 weeks, ≥~10 weeks, ≥~11 weeks, ≥~12 weeks (3 months), ≥~13 weeks, ≥~14 weeks, ≥~15 weeks, ≥~16 weeks (4 months), or more, such as ≥~5 months, ≥~6 months, ≥~7 months, ≥~8 months, ≥~9 months, ≥~10 months, ≥~11 months, or ≥~12 months (1 year), or even longer, such as, ≥~18 months, ≥~24 months (2 years), ≥~30 months, or, e.g., ≥~36 months (3 years) or longer.

The term "shelf life" has been described elsewhere herein. In aspects, shelf life refers to a period of time wherein any API of the composition loses more than about 10%, such as, e.g., ≤~9%, ≤~8%, ≤~7%, ≤~6%, ≤~5%, ≤~4%, ≤~3%, ≤~2%, or, e.g., ≤~1%, of the potency while in storage after manufacturing and prior to use.

Kits (Collections of Compositions and Administration Devices)

In aspects, the invention provides kits comprising one or more pilocarpine compound compositions described herein and one or more delivery devices for such compounds. In aspects, a kit provided by the invention can comprise a single delivery device comprising a single composition, the composition present in an amount representative of a single dose. In aspects, a kit provided by the invention can comprise a single delivery device comprising a single composition, the composition present in an amount representative of multiple doses, e.g., 2 or more, 3 or more, 5 or more, 10 or more 20 or more, 30 or more, or, e.g., 50 or more doses. In aspects, a kit provided by the invention can comprise a plurality of delivery devices comprising a single composition, the composition present in an amount representative of a single dose. In aspects, a kit provided by the invention can comprise a plurality of delivery devices comprising a single composition, the composition present in an amount representative of a multiple doses, e.g., 2 or more, 3 or more, 5 or more, 10 or more 20 or more, 30 or more, or, e.g., 50 or more doses. In aspects, a kit provided by the invention can comprise multiple compositions in multiple delivery devices, wherein at least one ingredient of at least one composition varies from that of at least one other composition in either presence or amount. In aspects, a kit provided by the invention can comprise multiple compositions in multiple delivery devices, wherein the amount of at least one composition in one delivery device varies from the amount of at least one other composition in at least one other delivery device. In aspects, a dose can be a single drop. In aspects, a dose can be 2 drops. In aspects, a dose can be 3 drops. Typically, a dose is one or two drops, e.g., a single drop.

In aspects, the invention provides a kit wherein compositions are pre-filled in a delivery device, and a kit comprises one or more pre-filled delivery devices and one or more additional components to facilitate administration of the composition(s). For example, in aspects, the invention provides a kit wherein composition(s) are provided in one or more pre-filled containers which facilitate administration of the compositions by drops, such as, e.g., one or more pre-filled dropper bottles as described herein. In alternative aspects, the invention provides a kit wherein compositions are pre-filled in a syringe and the kit comprises one or more needles to facilitate delivery of the compositions by injection, such as, e.g., for administration by intracameral injection. In aspects, the invention provides a composition which is formulated for injection and contained in an injection delivery device, a device adapted for injection delivery, or is packaged with an injection delivery device.

In aspects, the invention provides for a kit as described in this section, wherein the kit has a shelf life when stored at about room temperature, such as, e.g., about 25° C.+/−~2° C., for at least about 1 month, e.g., ~2, ~3, ~4, ~5, or at least about 6 months (e.g., 6-36 months.)

Stored at Room Temperature

In aspects, compositions provided by the invention, e.g., compositions in final packaged form, such as, e.g., compositions provided as a component of a kit, are stable when stored at standard room temperature, that is, controlled room temperature of between about 15° C. to 27° C., e.g., about 25° C.+/−2° C. for a period of at least about 1 month, e.g., ≥~3, ≥~6, ≥~9, ≥~12, ≥~18, ≥~24, ≥~28, ≥~33, or, e.g., ≥~36 months.

Exemplary Aspects of the Invention

The following is a non-limiting list of exemplary aspects of the invention, which illustrates embodiments of the invention in a summary form to aid readers in quickly understanding the overall scope of the invention. Similar to patent claims, listed aspects described in the paragraphs of this section may refer to (depend on/from) one or more other paragraphs. Readers will understand that such references mean that the features/characteristics or steps of such referenced aspects are incorporated into/combined with the referring aspect. E.g., if an aspect in a paragraph (e.g., a paragraph indicated by text at the end of the paragraph as aspect 2) refers to another aspect by one or more aspect numbers (e.g., aspect 1 or "any one of aspects 1-3"), it will be understood to include the elements, steps, or characteristics of such referenced aspects (e.g., aspect 1) in addition to those of the aspect in which the reference is made (e.g., if aspect 2 refers to aspect 1, it provides a description of a composition, method, system, device, etc., including the features of both aspect 1 and aspect 2.)

Composition without Citrate Buffer (Solution)

In aspects, the invention provides a pharmaceutically acceptable and ophthalmologically suitable composition for treating an ocular condition (e.g., an ocular condition or symptoms related thereto) comprising a pilocarpine compound in an amount greater than about 1% w/v and free of a citrate buffer, e.g., free of a sodium citrate compound, e.g., free of sodium citrate dihydrate, wherein the composition maintains (a) a pH of between about 3 and about 6 and (b) at least about 97% of the pilocarpine compound when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/any such condition, for at least about one month (aspect 1).

In aspects, the invention provides the composition of aspect 1, wherein the pilocarpine compound is a salt of pilocarpine (aspect 2).

In aspects, the invention provides the composition of any one or both of aspect 1 or aspect 2, wherein the pilocarpine compound is pilocarpine hydrochloride (aspect 3).

In aspects, the invention provides the composition of any one or more of aspect 1-aspect 3, wherein the composition comprises pilocarpine hydrochloride in an amount of about 1.25% w/v (aspect 4).

In aspects, the invention provides the composition of any one or more of aspect 1-aspect 3, wherein the ocular condition is selected from the group consisting of presbyopia, hyperopia, mydriasis, anisocoria, accommodative esotropia, myopia, and astigmatism (aspect 5).

In aspects, the invention provides the composition of any one or more of aspect 1-aspect 5, wherein the ocular condition is presbyopia (aspect 6).

In aspects, the invention provides the composition of any one or more of aspect 1-aspect 6, wherein the pH of the composition is maintained between about 3.5-about 5.5 (aspect 7).

In aspects, the invention provides the composition of any one or more of aspect 1-aspect 7, wherein the composition comprises a buffer component (aspect 8).

In aspects, the invention provides the composition of aspect 8, wherein the buffer component comprises a single buffer constituent (aspect 9).

In aspects, the invention provides the composition of aspect 9, wherein the single buffer component constituent is boric acid (aspect 10).

In aspects, the invention provides the composition of aspect 10, wherein the boric acid is present in the composition in an amount of about 0.5% w/v-about 1.5% w/v (aspect 11).

In aspects, the invention provides the composition of any one or more of aspect 8-aspect 11, wherein the ratio of the pilocarpine compound to the buffer component is between about 6:1-about 1:1.5 (aspect 12).

In aspects, the invention provides the composition of aspect 12, wherein the ratio of the pilocarpine compound to the buffer component is about 1.25:1 (aspect 13).

In aspects, the invention provides the composition of any one or more of aspects 1-13, wherein the composition is provided in the form of a solution, suspension, ointment, gel, or other dosage form suitable for topical administration to a mammalian eye (aspect 14).

In aspects, the invention provides the composition of aspect 14, wherein the composition is provided as a solution (aspect 15).

Composition without Borate (Solution)

In aspects, the invention provides a pharmaceutically acceptable and ophthalmologically suitable composition for treating an ocular condition (e.g., an ocular condition or symptoms related thereto) comprising a pilocarpine compound in an amount greater than about 1% w/v and free of boric acid, wherein the composition maintains (a) a pH of between about 3 and about 6 and (b) at least about 97% of the pilocarpine compound when stored under conditions comprising a temperature of between about 15° C. and about 42° C. and a relative humidity of between about 35% and about 75% relative humidity, e.g., about 15° C.-about 27° C. and about 60% relative humidity, when stored at about 38° C.-about 42° C. and 75% relative humidity, or when stored under either/any such condition, for at least about one month (aspect 16).

In aspects, the invention provides the composition of aspect 16, wherein the pilocarpine compound is a salt of pilocarpine (aspect 17).

In aspects, the invention provides the composition of any one or both of aspect 16 or aspect 17, wherein the pilocarpine compound is pilocarpine hydrochloride (aspect 18).

In aspects, the invention provides the composition of any one or more of aspect 16-aspect 18, wherein the composition comprises pilocarpine hydrochloride in an amount of about 1.25% w/v (aspect 19).

In aspects, the invention provides the composition of any one or more of aspect 16-aspect 19, wherein the ocular condition is selected from the group consisting of presbyopia, hyperopia, mydriasis, anisocoria, accommodative esotropia, myopia, and astigmatism (aspect 20).

In aspects, the invention provides the composition of any one or more of aspect 16-aspect 20, wherein the ocular condition is presbyopia (aspect 21).

In aspects, the invention provides the composition of any one or more of aspect 16-aspect 21, wherein the pH of the composition is maintained between about 3.5-about 5.5 (aspect 22).

In aspects, the invention provides the composition of any one or more of aspect 16-aspect 22, wherein the composition comprises a buffer component (aspect 23).

In aspects, the invention provides the composition of aspect 23, wherein the buffer component comprises a single buffer constituent (aspect 24).

In aspects, the invention provides the composition of aspect 24, wherein the single buffer component constituent is a citrate buffer (e.g., a sodium citrate compound, e.g., sodium citrate dihydrate) (aspect 25).

In aspects, the invention provides the composition of aspect 25, wherein the sodium citrate is present in the composition in an amount of about 0.005% w/v-about 0.09% w/v (aspect 26).

In aspects, the invention provides the composition of any one or more of aspect 23-aspect 26, wherein the ratio of the pilocarpine compound to the buffer component is between about 600:1 to about 12:1 (aspect 27).

In aspects, the invention provides the composition of aspect 27, wherein the ratio of the pilocarpine compound to the buffer component is about 57:1 (aspect 28).

In aspects, the invention provides the composition of any one or more of aspects 16-28, wherein the composition is provided in the form of a solution, suspension, ointment, gel, or other dosage form suitable for topical administration to a mammalian eye (aspect 29).

In aspects, the invention provides the composition of aspect 29, wherein the composition is provided as a solution (aspect 30).

Composition without Borate or Citrate Buffers (Solution)

In aspects, the invention provides a pharmaceutically acceptable and ophthalmologically suitable composition for treating an ocular condition (e.g., an ocular condition or symptoms related thereto) comprising a pilocarpine compound in an amount greater than about 1% w/v and free of both boric acid and citrate buffer, e.g., free of a sodium citrate compound, e.g., free of sodium citrate dihydrate, wherein the composition maintains (a) a pH of between about 3 and about 6 and (b) at least about 97% of the pilocarpine compound when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/any such condition, for at least about one month (aspect 31).

In aspects, the invention provides the composition of aspect 31, wherein the pilocarpine compound is a salt of pilocarpine (aspect 32).

In aspects, the invention provides the composition of any one or both of aspect 31 or aspect 32, wherein the pilocarpine compound is pilocarpine hydrochloride (aspect 33).

In aspects, the invention provides the composition of any one or more of aspect 31-aspect 33, wherein the composition comprises pilocarpine hydrochloride in an amount of about 1.25% w/v (aspect 34).

In aspects, the invention provides the composition of any one or more of aspect 31-aspect 34, wherein the ocular condition is selected from the group consisting of presbyopia, hyperopia, mydriasis, anisocoria, accommodative esotropia, myopia, and astigmatism (aspect 35).

In aspects, the invention provides the composition of any one or more of aspect 31-aspect 35, wherein the ocular condition is presbyopia (aspect 36).

In aspects, the invention provides the composition of any one or more of aspect 31-aspect 36, wherein the pH of the composition is maintained between about 3.5-about 5.5 (aspect 37).

In aspects, the invention provides the composition of any one or more of aspect 31-aspect 37, wherein the composition comprises a buffer component which does not comprise boric acid or sodium citrate (aspect 38).

In aspects, the invention provides the composition of aspect 38, wherein the buffer component comprises a single buffer constituent (aspect 39).

In aspects, the invention provides the composition of any one or more of aspect 31-aspect 37, wherein the composition does not comprise a buffer component (aspect 40).

In aspects, the invention provides the composition of any one or more of aspects 31-40, wherein the composition is provided in the form of a solution, suspension, ointment, gel, or other dosage form suitable for topical administration to a mammalian eye (aspect 41).

In aspects, the invention provides the composition of aspect 41, wherein the composition is provided as a solution (aspect 42).

Solution Composition Characteristics

In aspects, the invention provides the composition of any one or more of aspects 1-42, wherein the composition further comprises one or more non-buffer excipients (aspect 43).

In aspects, the invention provides the composition of aspect 43, wherein the one or more excipients is/are selected from the group consisting of a penetration enhancer component, a solubilization component, a demulcent component, a tonicity component, a thickening component, a chelation component, a pH adjusting component, a preservative component, and a carrier component (aspect 44).

In aspects, the invention provides the composition of any one or both of aspect 43 and aspect 44, wherein the composition comprises a tonicity component (aspect 45).

In aspects, the invention provides the composition of any one or more of aspect 43-aspect 45, wherein the composition comprises sodium chloride (aspect 46).

In aspects, the invention provides the composition of any one or more of aspect 43-aspect 46, wherein the composition comprises sodium chloride in an amount of about 0.01% w/v-about 0.1% w/v (aspect 47).

In aspects, the invention provides the composition of any one or more of aspect 1-aspect 47, wherein the osmolality of the composition is between about 280 mOsm/Kg-about 370 mOsm/Kg (aspect 48).

In aspects, the invention provides the composition of any one or more of aspect 43-aspect 48, wherein the composition comprises a preservation component (aspect 49).

In aspects, the invention provides the composition of any one or more of aspect 43-aspect 49, wherein the composition comprises a quaternary ammonium salt (aspect 50).

In aspects, the invention provides the composition of any one or more of aspect 43-aspect 50, wherein the composition comprises benzalkonium chloride (aspect 51).

In aspects, the invention provides the composition of any one or more of aspect 43-aspect 51, wherein the composition comprises benzalkonium chloride in an amount of about 0.003% w/v-about 0.02% w/v (aspect 52).

In aspects, the invention provides the composition of any one or more of aspect 43-aspect 52, wherein the composition comprises a penetration enhancer component (aspect 53).

In aspects, the invention provides the composition of aspect 53, wherein the penetration enhancer component comprises at least one constituent which provides detectable or significant activity as two or more of a penetration enhancer, a solubilizer, a demulcent, a buffer, a tonicity agent, a thickener, a chelator, a pH adjusting agent, a preservative, or a carrier (aspect 54).

In aspects, the invention provides the composition of aspect 54, wherein the penetration enhancer component comprises at least one constituent which provides detectable or significant activity as a penetration enhancer, a solubilizer, a demulcent, or any combination of two or more thereof (aspect 55).

In aspects, the invention provides the composition of aspect 55, wherein the penetration enhancer component comprises at least one constituent which provides detectable or significant activity as a penetration enhancer, a solubilizer, and a demulcent (aspect 56).

In aspects, the invention provides the composition of any one or more of aspect 53-aspect 56, wherein the penetration component comprises one or more of polyoxyethylene sorbitan fatty acid ester(s), tocopheryl polyethylene glycol succinate (TPGS), poly-arginine, polyserine, tromethamine (tris), sesame seed oil, or oils having similar compositions and functional characteristics suitable for ophthalmic use (aspect 57).

In aspects, the invention provides the composition of aspect 57, wherein the polyoxyethylene sorbitan fatty acid ester(s) include polyoxyethylene sorbitan laurate (polysorbate 20), polyoxyethylene sorbitan palmitate (polysorbate 40), a polyoxyethylene sorbitan stearate (polysorbate 60), a polyoxyethylene sorbitan tri stearate (polysorbate 65), or a polyoxyethylene sorbitan oleate/polyoxyethylene sorbitan mono-oleate ester (e.g., polysorbate 80) (aspect 58).

In aspects, the invention provides the composition of aspect 58, wherein the penetration component is present in an amount of about 0.1% w/v-about 5% w/v (aspect 59).

In aspects, the invention provides the composition of aspect 59, wherein the penetration component is present in an amount of about 0.1% w/v-about 3% w/v (aspect 60).

In aspects, the invention provides the composition of any one or more of aspect 57-aspect 60, wherein the penetration component comprises polysorbate 80 (aspect 61).

In aspects, the invention provides the composition of aspect 61, wherein the polysorbate 80 is present in the composition in an amount of about 0.25% w/v (aspect 62).

In aspects, the invention provides the composition of one or more of aspect 53-aspect 62, wherein the penetration component comprises at least one constituent which further provides detectable or significant demulcent effect, and wherein the constituent detectably or significantly reduces the amount of irritation caused by the product over a corresponding product comprising the same amount of pilocarpine compound provided in the same dosage form, for the same indication, and for substantially the same administration period as reported in an appropriately administered clinical trial (aspect 63).

In aspects, the invention provides the composition of aspect 63, wherein the constituent is polysorbate 80 (aspect 64).

Gel Composition

In aspects, the invention provides a pharmaceutically acceptable and ophthalmologically suitable composition for treating an ocular condition (e.g., an ocular condition or symptoms related thereto) comprising a pilocarpine compound in an amount of about 1% w/v-about 3% w/v; a solubilization component in an amount of between about 0.1% w/v-about 0.7% w/v; a preservation component in an amount of about 0.003% w/v-about 0.02% w/v; a tonicity component in an amount of between about 3.5% w/v-about 5.5% w/v; a viscosity enhancement component (thickening component) in an amount of about 0.1% w/v-about 1% w/v, wherein the composition maintains (a) a pH of between about 3 and about 6 and (b) at least about 97% of the pilocarpine compound when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/any such condition, for at least about one month (aspect 65).

In aspects, the invention provides the composition of aspect 65, wherein the pilocarpine compound is a salt of pilocarpine (aspect 66).

In aspects, the invention provides the composition of any one or both of aspect 65 or aspect 66, wherein the pilocarpine compound is pilocarpine hydrochloride (aspect 67).

In aspects, the invention provides the composition of any one or more of aspect 65-aspect 67, wherein the composition comprises pilocarpine hydrochloride in an amount of about 1.25% w/v (aspect 68).

In aspects, the invention provides the composition of any one or more of aspect 65-aspect 68, wherein the ocular condition is selected from the group consisting of presbyopia, hyperopia, mydriasis, anisocoria, accommodative esotropia, myopia, and astigmatism (aspect 69).

In aspects, the invention provides the composition of any one or more of aspect 65-aspect 69, wherein the ocular condition is presbyopia (aspect 70).

In aspects, the invention provides the composition of any one or more of aspect 65-aspect 70, wherein the pH of the composition is maintained between about 3.5-about 5.5 (aspect 71).

In aspects, the invention provides the composition of any one or more of aspect 65-aspect 71, wherein the solubilization component comprises at least one constituent which demonstrates detectable or significant activity as both a solubilizing agent and a penetration enhancer (aspect 72).

In aspects, the invention provides the composition of any one or more of aspect 65-aspect 72, wherein the solubilization component comprises a polyethoxylated castor oil and tromethamine (tris) (aspect 73).

In aspects, the invention provides the composition of aspect 73, wherein the solubilization component comprises a polyethoxylated castor oil in an amount of about 0.1% w/v-about 0.5% w/v (aspect 74).

In aspects, the invention provides the composition of aspect 73 or aspect 74, wherein the solubilization component comprises tromethamine (tris) in an amount of about 0.1% w/v-about 0.5% w/v (aspect 75).

In aspects, the invention provides the composition of any one or more of aspect 65-aspect 75, wherein the preservation component comprises a quaternary ammonium salt (aspect 76).

In aspects, the invention provides the composition of aspect 76, wherein the quaternary ammonium salt is benzalkonium chloride (aspect 77).

In aspects, the invention provides the composition of any one or more of aspect 65-aspect 77, wherein the tonicity component comprises mannitol (aspect 78).

In aspects, the invention provides the composition of any one or more of aspect 65-aspect 47, wherein the osmolality of the composition is about 171 mOsm/Kg-about 1171 mOsm/Kg, such as, e.g., about 200 mOsm/Kg-about 1000 mOsm/Kg, about 250 mOsm/Kg-about 500 mOsm/Kg, or, e.g., about 280 mOsm/Kg-about 370 mOsm/Kg, e.g., about 250-about 350 mOsm/Kg or about 270 mOsm/Kg-about 330 mOsm/Kg (aspect 79).

In aspects, the invention provides the composition of any one or more of aspect 65-aspect 79, wherein the viscosity enhancement component comprises gellan gum (aspect 80).

In aspects, the invention provides the composition of any one or more of aspect 65-aspect 80, wherein the composition further comprises a pH adjustment component and a carrier (aspect 81).

In aspects, the invention provides the composition of any one or more of aspects 65-81, wherein the composition is provided in the form of a solution, suspension, ointment, gel, or other dosage form suitable for topical administration to a mammalian eye (aspect 82).

In aspects, the invention provides the composition of aspect 82, wherein the composition is provided as a gel (aspect 83).

In aspects, the invention provides the composition of aspect 83, wherein the pilocarpine compound of the gel composition is retained in the eye for a detectably or significantly longer period of time than a comparable composition providing the same amount of pilocarpine compound provided in the form of a liquid (e.g., aqueous) solution (aspect 84).

In aspects, the invention provides the composition of aspect 83 or aspect 84, wherein the composition provided in the form of a gel causes detectably or significantly less blurriness than a comparable composition providing the same amount of pilocarpine compound provided in the form of a liquid (e.g., aqueous) solution (aspect 85).

Stability

In aspects, the invention provides the composition of any one or more of aspect 1-aspect 85 or aspects 151-169, wherein the composition maintains at least about 98% of the pilocarpine compound when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/any such condition, for at least about three months, such as, e.g., about 3 months to about 9 months (aspect 86).

In aspects, the invention provides the composition of any one or more of aspect 1-aspect 86 or aspects 151-169, wherein the composition maintains at least about 98% of the pilocarpine compound when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/any such condition, for at least about six months, such as, e.g., about 6 months to about 12 months (aspect 87).

In aspects, the invention provides the composition of any one or more of aspect 1-aspect 87 or aspects 151-169, wherein the composition maintains at least about 98% of the pilocarpine compound when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/any such condition, for at least about nine months such as, e.g., about 9 months to about 18 months (aspect 88).

In aspects, the invention provides the composition of any one or more of aspect 1-aspect 88 or aspects 151-169, wherein the composition maintains at least about 98% of the pilocarpine compound when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/any such condition, for at least about 12 months, such as, e.g., about 12 months-about 24 months (aspect 89).

In aspects, the invention provides the composition of any one or more of aspect 1-aspect 89 or aspects 151-169, wherein the composition maintains at least about 98% of the pilocarpine compound when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/any such condition, for at least about 18 months, such as, e.g., about 18 months-about 32 months (aspect 90).

In aspects, the invention provides the composition of any one or more of aspect 1-aspect 90 or aspects 151-169, wherein the composition maintains at least about 98% of the pilocarpine compound when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/any such condition, for at least about 24 months, such as, e.g., about 24 months-about 36 months (aspect 91).

In aspects, the invention provides the composition of any one or more of aspect 1-aspect 91 or aspects 151-169, wherein the composition maintains at least about 98% of the pilocarpine compound when stored under conditions comprising a temperature of between about 15° C. and about 42° C. and a relative humidity of between about 35% and about 75% relative humidity, e.g., at about 15° C.-about 27° C. and about 60% relative humidity, when stored at about 38° C.-about 42° C. and 75% relative humidity, or when stored under either/any such condition, for at least about 36 months (aspect 92).

In aspects, the invention provides the composition of any one or more of aspect 1-aspect 92 or aspects 151-169, wherein the composition comprises less than about 2.5% total impurities after storage under conditions comprising a temperature of between about 15° C. and about 42° C. and a relative humidity of between about 35% and about 75% relative humidity, e.g., at about 15° C.-about 27° C. and about 60% relative humidity, after storage at about 38° C.-about 42° C. and 75% relative humidity, or after storage under either/any such condition, for a period of at least about 1 month (aspect 93).

In aspects, the invention provides the composition of any one or more of aspect 1-aspect 93 or aspects 151-169, wherein the composition comprises less than about 2.5% total impurities after storage under conditions comprising a temperature of between about 15° C. and about 42° C. and a relative humidity of between about 35% and about 75% relative humidity, e.g., at about 15° C.-about 27° C. and about 60% relative humidity, after storage at about 38°

C.-about 42° C. and 75% relative humidity, or after storage under either/any such condition, for a period of at least about 3 months (aspect 94).

In aspects, the invention provides the composition of any one or more of aspect 1-aspect 94 or aspects 151-169, wherein the composition comprises less than about 2.5% total impurities after storage under conditions comprising a temperature of between about 15° C. and about 42° C. and a relative humidity of between about 35% and about 75% relative humidity, e.g., at about 15° C.-about 27° C. and about 60% relative humidity, after storage at about 38° C.-about 42° C. and 75% relative humidity, or after storage under either/any such condition, for a period of at least about 6 months (aspect 95).

In aspects, the invention provides the composition of any one or more of aspect 1-aspect 95 or aspects 151-169, wherein the composition comprises less than about 2.5% total impurities after storage under conditions comprising a temperature of between about 15° C. and about 42° C. and a relative humidity of between about 35% and about 75% relative humidity, e.g., at about 15° C.-about 27° C. and about 60% relative humidity, after storage at about 38° C.-about 42° C. and 75% relative humidity, or after storage under either/any such condition, for a period of at least about 9 months (aspect 96).

In aspects, the invention provides the composition of any one or more of aspect 1-aspect 96 or aspects 151-169, wherein the composition comprises less than about 2.5% total impurities after storage under conditions comprising a temperature of between about 15° C. and about 42° C. and a relative humidity of between about 35% and about 75% relative humidity, e.g., at about 15° C.-about 27° C. and about 60% relative humidity, after storage at about 38° C.-about 42° C. and 75% relative humidity, or after storage under either/any such condition, for a period of at least about 12 months (aspect 97).

In aspects, the invention provides the composition of any one or more of aspect 1-aspect 97 or aspects 151-169, wherein the composition comprises less than about 2.5% total impurities after storage under conditions comprising a temperature of between about 15° C. and about 42° C. and a relative humidity of between about 35% and about 75% relative humidity, e.g., at about 15° C.-about 27° C. and about 60% relative humidity, after storage at about 38° C.-about 42° C. and 75% relative humidity, or after storage under either/any such condition, for a period of at least about 18 months (aspect 98).

In aspects, the invention provides the composition of any one or more of aspect 1-aspect 98 or aspects 151-169, wherein the composition comprises less than about 2.5% total impurities after storage under conditions comprising a temperature of between about 15° C. and about 42° C. and a relative humidity of between about 35% and about 75% relative humidity, e.g., at about 15° C.-about 27° C. and about 60% relative humidity, after storage at about 38° C.-about 42° C. and 75% relative humidity, or after storage under either/any such condition, for a period of at least about 24 months (aspect 99).

In aspects, the invention provides the composition of any one or more of aspect 1-aspect 99 or aspects 151-169, wherein the composition comprises less than about 2.5% total impurities after storage under conditions comprising a temperature of between about 15° C. and about 42° C. and a relative humidity of between about 35% and about 75% relative humidity, e.g., at about 15° C.-about 27° C. and about 60% relative humidity, after storage at about 38° C.-about 42° C. and 75% relative humidity, or after storage under either/any such condition, for a period of at least about 36 months (aspect 100).

Methods of Treatment

In aspects, the invention provides a method of improving vision, the method comprising administering an effective amount of any one or more of the compositions provided in any one or more of aspect 1-aspect 100 or aspects 151-169, to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in vision (aspect 101).

In aspects, the invention provides a method of reducing visual impairment, the method comprising administering an effective amount of any one or more of the compositions provided in any one or more of aspect 1-aspect 100 or aspects 151-169, to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same reduction in visual impairment (aspect 102).

In aspects, the invention provides a method of treating an ophthalmic condition (e.g., an ocular condition or symptoms related thereto) selected from the group consisting of presbyopia, hyperopia, mydriasis, anisocoria, accommodative esotropia, myopia, and astigmatism, the method comprising administering an effective amount of any one or more of the compositions provided in any one or more of aspect 1-aspect 100 or aspects 151-169, to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement of the same ophthalmic condition (aspect 103).

In aspects, the invention provides a method of treating presbyopia (e.g., an presbyopia or symptoms related thereto), the method comprising administering an effective amount of any one or more of the compositions provided in any one or more of aspect 1-aspect 100 or aspects 151-169 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in presbyopia (aspect 104).

In aspects, the invention provides a method of treating hyperopia (e.g., hyperopia or symptoms related thereto), the method comprising administering an effective amount of any one or more of the compositions provided in any one or more of aspect 1-aspect 100 or aspects 151-169 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in hyperopia (aspect 105).

In aspects, the invention provides a method of treating mydriasis (e.g., mydriasis or symptoms related thereto), the method comprising administering an effective amount of any one or more of the compositions provided in any one or more of aspect 1-aspect 100 or aspects 151-169 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in mydriasis (aspect 106).

In aspects, the invention provides a method of treating anisocoria (e.g., anisocoria or symptoms related thereto), the method comprising administering an effective amount of any one or more of the compositions provided in any one or more of aspect 1-aspect 100 or aspects 151-169 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in anisocoria (aspect 107).

In aspects, the invention provides a method of treating accommodative esotropia (e.g., accommodative esotropia or symptoms related thereto), the method comprising administering an effective amount of any one or more of the compositions provided in any one or more of aspect 1-aspect 100 or aspects 151-169 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in esotropia (aspect 108).

In aspects, the invention provides a method of treating myopia (e.g., myopia or symptoms related thereto), the method comprising administering an effective amount of any one or more of the compositions provided in any one or more of aspect 1-aspect 100 or aspects 151-169 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in myopia (aspect 109).

In aspects, the invention provides a method of treating astigmatism (e.g., astigmatism or symptoms related thereto), the method comprising administering an effective amount of any one or more of the compositions provided in any one or more of aspect 1-aspect 100 or aspects 151-169 to the eye of a recipient, an effective amount being the application of 1-2 drops of the composition(s) to a mammalian eye once or twice daily, and optionally repeating for a number of times demonstrated to provide a significant clinical effect in a significant number of patients in a well-controlled and adequate study or that is shown to be bioequivalent to a product that has been demonstrated to achieve the at least substantially the same, generally the same, or effectively the same improvement in astigmatism (aspect 110).

In aspects, the invention provides a method of improving, reducing, or treating any one or more of the ophthalmic conditions or symptoms related thereto provided in any one or more of aspect 101-aspect 110, wherein the method comprises the administration of 1 drop of composition to each affected eye, both eyes, or the dominant eye of the recipient once or twice daily over the course of an effective treatment period (aspect 111).

In aspects, the invention provides the method of aspect 111, wherein the method comprises the administration of 1 drop of the composition to each affected eye, both eyes, or the dominant eye of the recipient once daily over the course of an effective treatment period (aspect 112).

In aspects, the invention provides the method of aspect 111 or aspect 112, wherein the effective treatment period is period of time lasting between 1 day and 5 years (aspect 113).

In aspects, the invention provides the method of aspect 113, wherein the effective treatment period is period of time lasting between 1 day and 3 years (aspect 114).

In aspects, the invention provides the method of aspect 114, wherein the effective treatment period is period of time lasting between 1 day and 1 year (aspect 115).

In aspects, the invention provides the method of aspect 115, wherein the effective treatment period is period of time lasting between 1 day and 6 months (aspect 116).

In aspects, the invention provides the method of aspect 116, wherein the effective treatment period is period of time lasting between 1 day and 3 months (aspect 117).

In aspects, the invention provides the method of aspect 117, wherein the effective treatment period is period of time lasting between 1 day and 1 month (aspect 118).

In aspects, the invention provides the method of aspect 118, wherein the effective treatment period is period of time lasting between 1 day and 1 week (aspect 119).

In aspects, the invention provides the method of aspect 119, wherein the effective treatment period is period of time lasting between 1 day and 1 week (aspect 120).

In aspects, the invention provides the method of aspect 111 or aspect 112, wherein the method comprises chronic treatment, wherein the effective treatment period is an indefinite period of time (aspect 121).

Comparable or Improved Clinical Effects

In aspects, the invention provides a method of improving vision by providing to a patient in need thereof an effective amount of a composition of any one or more of aspect 1-aspect 100 or aspects 151-169, wherein the method is clinically demonstrated to be as effective or detectably or significantly more effective than treatment with the product approved under U.S. Food and Drug Administration NDA Number 214028 (VUITY®) for the same or similar indication (e.g., improving vision) and for at least substantially the same administration period (aspect 122).

In aspects, the invention provides a method of reducing visual impairment by providing to a patient in need thereof an effective amount of a composition of any one or more of aspect 1-aspect 100 or aspects 151-169, wherein the method is clinically demonstrated to be as effective or detectably or significantly more effective than treatment with the product approved under U.S. Food and Drug Administration NDA Number 214028 (VUITY®) for the same or similar indication (e.g., reducing visual impairment) and for at least substantially the same administration period (aspect 123).

In aspects, the invention provides a method of treating presbyopia by providing to a patient in need thereof an effective amount of a composition of any one or more of aspect 1-aspect 100 or aspects 151-169, wherein the method is clinically demonstrated to be as effective or detectably or significantly more effective than treatment with the product approved under U.S. Food and Drug Administration NDA Number 214028 (VUITY®) for the same or similar indication (e.g., presbyopia) and for at least substantially the same administration period (aspect 124).

In aspects, the invention provides a method of treating hyperopia by providing to a patient in need thereof an effective amount of a composition of any one or more of aspect 1-aspect 100 or aspects 151-169, wherein the method is clinically demonstrated to be as effective or detectably or significantly more effective than treatment with the product approved under U.S. Food and Drug Administration NDA Number 214028 (VUITY®) for the same or similar indication (e.g., hyperopia) and for at least substantially the same administration period (aspect 125).

In aspects, the invention provides a method of treating mydriasis by providing to a patient in need thereof an effective amount of a composition of any one or more of aspect 1-aspect 100 or aspects 151-169, wherein the method is clinically demonstrated to be as effective or detectably or significantly more effective than treatment with the product approved under U.S. Food and Drug Administration NDA Number 214028 (VUITY®) for the same or similar indication (e.g., mydriasis) and for at least substantially the same administration period (aspect 126).

In aspects, the invention provides a method of treating anisocoria by providing to a patient in need thereof an effective amount of a composition of any one or more of aspect 1-aspect 100 or aspects 151-169, wherein the method is clinically demonstrated to be as effective or detectably or significantly more effective than treatment with the product approved under U.S. Food and Drug Administration NDA Number 214028 (VUITY®) for the same or similar indication (e.g., anisocoria) and for at least substantially the same administration period (aspect 127).

In aspects, the invention provides a method of treating accommodative esotropia by providing to a patient in need thereof an effective amount of a composition of any one or more of aspect 1-aspect 100 or aspects 151-169, wherein the method is clinically demonstrated to be as effective or detectably or significantly more effective than treatment with the product approved under U.S. Food and Drug Administration NDA Number 214028 (VUITY®) for the same or similar indication (e.g., accommodative esotropia) and for at least substantially the same administration period (aspect 128).

In aspects, the invention provides a method of treating myopia by providing to a patient in need thereof an effective amount of a composition of any one or more of aspect 1-aspect 100 or aspects 151-169, wherein the method is clinically demonstrated to be as effective or detectably or significantly more effective than treatment with the product approved under U.S. Food and Drug Administration NDA Number 214028 (VUITY®) for the same or similar indication (e.g., myopia) and for at least substantially the same administration period (aspect 129).

In aspects, the invention provides a method of treating astigmatism by providing to a patient in need thereof an effective amount of a composition of any one or more of aspect 1-aspect 100 or aspects 151-169, wherein the method is clinically demonstrated to be as effective or detectably or significantly more effective than treatment with the product approved under U.S. Food and Drug Administration NDA Number 214028 (VUITY®) for the same or similar indication (e.g., astigmatism) and for at least substantially the same administration period (aspect 130).

Result in Reduced Side Effects

In aspects, the invention provides a method of treating presbyopia or symptoms related thereto, the method comprising administration of an effective amount of a composition of any one or more of aspect 1-aspect 100 or aspects 151-169, wherein the effective amount is 1-2 drops of the composition administered once or twice daily over an effective treatment period, wherein the method results in detectably or significantly reduced ocular blurring compared to treatment of presbyopia with the product approved under U.S. Food and Drug Administration NDA Number 214028 (VUITY®) for at least substantially the same administration period (aspect 131).

In aspects, the invention provides a method of treating presbyopia or symptoms related thereto, the method comprising administration of an effective amount of a composition of any one or more of aspect 1-aspect 100 or aspects 151-169, wherein the effective amount is 1-2 drops of the composition administered once or twice daily over an effective treatment period, wherein the method results in detectably or significantly reduced ocular discomfort compared to treatment of presbyopia with the product approved under U.S. Food and Drug Administration NDA Number 214028 (VUITY®) for at least substantially the same administration period (aspect 132).

In aspects, the invention provides a method of treating presbyopia or symptoms related thereto, the method comprising administration of an effective amount of a composition of any one or more of aspect 1-aspect 100 or aspects 151-169, wherein the effective amount is 1-2 drops of the composition administered once or twice daily over an effective treatment period, wherein the method results in detectably or significantly reduced eye pain compared to treatment of presbyopia with the product approved under U.S. Food and Drug Administration NDA Number 214028 (VUITY®) for at least substantially the same administration period (aspect 133).

In aspects, the invention provides a method of treating presbyopia or symptoms related thereto, the method comprising administration of an effective amount of a composition of any one or more of aspect 1-aspect 100 or aspects 151-169, wherein the effective amount is 1-2 drops of the composition administered once or twice daily over an effective treatment period, wherein the method results in detectably or significantly reduced brow ache compared to treatment of presbyopia with the product approved under U.S. Food and Drug Administration NDA Number 214028 (VUITY®) for at least substantially the same administration period (aspect 134).

In aspects, the invention provides a method of treating presbyopia or symptoms related thereto, the method comprising administration of an effective amount of a composition of any one or more of aspect 1-aspect 100 or aspects 151-169, wherein the effective amount is 1-2 drops of the composition administered once or twice daily over an effective treatment period, wherein the method results in detectably or significantly reduced blurry vision compared to treatment of presbyopia with the product approved under U.S. Food and Drug Administration NDA Number 214028 (VUITY®) for at least substantially the same administration period (aspect 135).

In aspects, the invention provides a method of treating presbyopia or symptoms related thereto, the method comprising administration of an effective amount of a composition of any one or more of aspect 1-aspect 100 or aspects 151-169, wherein the effective amount is 1-2 drops of the composition administered once or twice daily over an effective treatment period, wherein the method results in detectably or significantly reduced light sensitivity compared to treatment of presbyopia with the product approved under U.S. Food and Drug Administration NDA Number 214028 (VUITY®) for at least substantially the same administration period (aspect 136).

In aspects, the invention provides a method of treating presbyopia or symptoms related thereto, the method comprising administration of an effective amount of a composition of any one or more of aspect 1-aspect 100 or aspects 151-169, wherein the effective amount is 1-2 drops of the composition administered once or twice daily over an effective treatment period, wherein the method results in detectably or significantly reduced stinging compared to treatment of presbyopia with the product approved under U.S. Food and Drug Administration NDA Number 214028 (VUITY®) for at least substantially the same administration period (aspect 137).

In aspects, the invention provides a method of treating presbyopia or symptoms related thereto, the method comprising administration of an effective amount of a composition of any one or more of aspect 1-aspect 100 or aspects 151-169, wherein the effective amount is 1-2 drops of the composition administered once or twice daily over an effective treatment period, wherein the method results in detectably or significantly reduced itching compared to treatment of presbyopia with the product approved under U.S. Food and Drug Administration NDA Number 214028 (VUITY®) for at least substantially the same administration period (aspect 138).

Method of Manufacturing

In aspects, the invention provides a method of manufacturing any one or more of the compositions of any one or more of aspect 1-aspect 64 or aspects 151-169, wherein the method comprises (a) preparation of a bulk composition, (b) offline filtration of the bulk composition, (c) online filtration of the bulk composition, and (d) final packaging of the composition (aspect 139).

The method of manufacturing of aspect 139, wherein the composition(s) resulting from the method are used in any one or more of the methods of treatment in any one or more of aspects 101-138 (aspect 140).

In aspects, the invention provides a method of manufacturing any one or more of the compositions of any one or more of aspect 65-aspect 85 or aspects 151-169, wherein the method comprises (a) preparation of a polymer phase, (b) preparation of a drug phase, (c) filtration of the drug phase into the polymer phase, (d) filtering the composition resulting from (c), and (e) final packaging of the composition (aspect 141).

The method of manufacturing of aspect 141, wherein the composition(s) resulting from the method are used in any one or more of the methods of treatment in any one or more of aspects 101-138 (aspect 142).

Kit(s)

In aspects, the invention provides a kit comprising a composition according to any one or more of aspect 1-aspect 100 or aspects 151-169 and a device suitable for facilitating the delivery of the composition to a recipient eye (aspect 143).

In aspects, the invention provides the kit of aspect 143, wherein the device suitable for facilitating the delivery of the composition to a recipient eye is a container capable of delivering compositions held therein in a drop-by-drop manner (a dropper bottle) (aspect 144).

In aspects, the invention provides the kit of aspect 143, wherein the device suitable for facilitating the delivery of the composition to a recipient eye is a container capable of being squeezed to a sufficient extent to expel a suitable amount of composition held therein (a squeeze bottle) (aspect 145).

In aspects, the invention provides the kit of any one or more of aspect 143-aspect 145, wherein the composition is provided within the delivery device/container (aspect 146).

In aspects, the invention provides the kit of any one or more of aspect 143-aspect 146, wherein the kit comprises multiple doses of composition provided as a plurality of single dose containers, a single multi-dose container, or a plurality of multi-dose containers (aspect 147).

In aspects, the invention provides the kit of aspect 144, wherein the composition is a composition manufactured according to any one or more of the methods of any one or both of aspect 139 and aspect 140 (aspect 148).

In aspects, the invention provides the kit of aspect 145, wherein the composition is a composition manufactured according to any one or more of the methods of any one or both of aspect 141 and aspect 142 (aspect 149).

In aspects, the invention provides the kit of any one or more of aspect 143-aspect 149, wherein the kit is used in the method of treatment of any one or more of aspects 101-138 (aspect 150).

In aspects, the invention provides the composition of any one or more of aspects 1-100, wherein the ratio of pilocarpine compound(s) to a buffer component present in the composition is between about 1:0.001 and about 1:3, such as, e.g., about 1:0.6 (aspect 151).

In aspects, the invention provides the composition of any one or more of aspects 1-100 or aspect 151, wherein the ratio of pilocarpine compound(s) to borate compound(s) present in the composition is between about 1:0.1 and about 1:4, such as, e.g., about 1:0.8 (or, e.g., stated alternatively, about 1.25:1) (aspect 152).

In aspects, the invention provides the composition of any one or more of aspects 1-100, 151, or 152, wherein the ratio of pilocarpine compound(s) to citrate compound(s) present in the composition is between about 1:0.001 and about 1:0.2, such as, e.g., about 1:0.02 (aspect 153).

In aspects, the invention provides the composition of any one or more of aspects 1-100 or aspects 151-153, wherein the ratio of pilocarpine compound(s) to acetate compound(s) present in the composition is between about 1:0.05 and about 1:3, such as, e.g., about 1:0.6 (aspect 154).

In aspects, the invention provides the composition of any one or more of aspects 1-100 or aspects 151-154, wherein the ratio of benzalkonium chloride to pilocarpine compound(s) present in the composition is between about 1:25 and about 1:1:40000, such as between about 1:125 and about 1:25000, e.g., about 1:167 (aspect 155).

In aspects, the invention provides the composition of any one or more of aspects 1-100 or aspects 151-155, wherein the ratio of benzalkonium chloride to borate compound(s) present in the composition is between about 1:25 and about 1:15000, such as, e.g., about 1:50-about 1:10000, e.g., about 1:133 (aspect 156).

In aspects, the invention provides the composition of any one or more of aspects 1-100 or aspects 151-156, wherein the ratio of benzalkonium chloride to citrate compound(s) present in the composition is between about 1:0.25 and about 1:900, such as, e.g., about 1:0.5-about 1:900, such as, e.g., greater than about 1:2, e.g., about 1:1-about 1:5, as in, e.g., about 1:3 (aspect 157).

In aspects, the invention provides the composition of any one or more of aspects 1-100 or aspects 151-157, wherein the ratio of benzalkonium chloride to acetate compound(s) present in the composition is between about 1:10 and about 1:25000, such as between about 1:20 and about 1:15000, as in, e.g., about 1:100 (aspect 158).

In aspects, the invention provides the composition of any one or more of aspects 1-100 or aspects 151-158, wherein the ratio of pilocarpine compound(s) to polysorbate 80 present in the composition is between about 1:0.002 and about 1:10, such as, e.g., about 1:0.2 (aspect 159).

In aspects, the invention provides the composition of any one or more of aspects 1-100 or aspects 151-159, wherein the ratio of borate compound(s) to polysorbate 80 present in the composition is between about 1:0.006 and about 1:10, such as, e.g., about 1:0.25 (aspect 160).

In aspects, the invention provides the composition of any one or more of aspects 1-100 or aspects 151-160, wherein the ratio of citrate compound(s) to polysorbate 80 present in the compositions is between about 1:0.1 and about 1:1000, such as, e.g., about 1:1 (aspect 161).

In aspects, the invention provides the composition of any one or more of aspects 1-100 or aspects 151-161, wherein the ratio of acetate compound(s) to polysorbate 80 present in the composition is between about 1:0.006 and about 1:25, such as, e.g., about 1:0.3 (aspect 162).

In aspects, the invention provides the composition of any one or more of aspects 1-100 or aspects 151-162, wherein the ratio of benzalkonium chloride to polysorbate 80 present in the composition is between about 1:0.5 and about 1:50000, such as, e.g., about 1:1-about 1:50000, about 1:1-about 1:50, or, e.g., about 1:33 (aspect 163).

In aspects, the invention provides the composition of any one or more of aspects 1-100 or aspects 151-163, wherein the ratio of pilocarpine compound(s) to a penetration enhancer component present in the composition is between about 1:0.001 and about 1:10, such as, e.g., about 1:0.1-about 1:0.3 (aspect 164).

In aspects, the invention provides the composition of any one or more of aspects 1-100 or aspects 151-164, wherein the composition comprises pilocarpine as the sole active pharmaceutical ingredient (aspect 165).

In aspects, the invention provides the composition of any one or more of aspects 1-100 or aspects 151-165, wherein the composition comprises a carrier, and further wherein the carrier is non-deuterated water (e.g., water comprising an amount of deuterium which is not significantly more than that which typically occurs in nature) (aspect 166).

In aspects, the invention provides the composition of any one or more of aspects 1-100 or aspects 151-166, wherein the composition provides a detectably or significantly, e.g., a statistically significantly, reduced buffering capacity compared to a reference product, such as, e.g., a product approved under U.S. Food and Drug Administration number 214028 (VUITY®) or a composition having demonstrated or demonstrating bioequivalence to a product approved under U.S. Food and Drug Administration number 214028 (aspect 167).

In aspects, the invention provides the composition of any one or more of aspects 1-100 or aspects 151-167, wherein the composition demonstrates a detectably or significantly, e.g., statistically significantly, similar stability compared to a reference product, such as, e.g., a product approved under U.S. Food and Drug Administration number 214028 (VUITY®) or a composition having demonstrated or demonstrating bioequivalence to a product approved under U.S. Food and Drug Administration number 214028 (aspect 168).

In aspects, the invention provides the composition of any one or more of aspects 1-100 or aspects 151-168, wherein the composition provides a detectably or significantly, e.g., a statistically significantly, reduced buffering capacity compared to a reference product, such as, e.g., a product approved under U.S. Food and Drug Administration number 214028 (VUITY®) or a composition having demonstrated or demonstrating bioequivalence to a product approved under U.S. Food and Drug Administration number 214028, and further wherein the composition also demonstrates a detectably or significantly, e.g., statistically significantly, similar stability compared to a reference product, such as, e.g., a product approved under U.S. Food and Drug Administration number 214028 (VUITY®) or a composition having demonstrated or demonstrating bioequivalence to a product approved under U.S. Food and Drug Administration number 214028 (aspect 169).

Within this list of exemplary aspects of the invention, when citing a group or list of aspects, any referenced aspect number should be considered to be incorporated in the statement "any one or more of" or similarly "one or both of", without exclusion. For example, the recitation " . . . any one or more of aspects 1-100 or aspects 151-168 . . . " should be interpreted to mean any one or more of aspect 1, 2, 3, 4 . . . 50, 60, 70, 80 . . . up to 100, 151, 152, 152 . . . up to aspect 168. For example, such a recitation includes any one or more of aspects 1-100 and any one or more of aspects 151-168, including one or more aspects falling in either group.

EXAMPLES

The following detailed Examples of certain aspects of the invention are provided to assist readers in further understanding aspects of the invention or principles related to practicing aspects of the invention. Any particular materials, methods, steps, and conditions employed/described in the following Examples, and any results thereof, are intended to further illustrate aspects of the invention. These Examples reflect exemplary embodiments of the invention, and the specific methods, findings, principles of such Examples, and the general implications thereof, can be combined with any other aspect of the invention. However, readers should understand that the invention is not limited by or to any part of the Examples.

Example 1

Tables 4, 5, and 6, below, provide exemplary Formulation A, exemplary Formulation B, and exemplary Formulation C, each providing a list of ingredients suitable for compositions of the present invention provided in the form of a solution(s).

TABLE 4

Exemplary Formulation A. Pilocarpine Solution + Boric Acid (without Citrate).

| No. | Ingredient | Percentage (w/v) in Composition |
|---|---|---|
| 1 | Pilocarpine Compound | 1-3 |
| 2 | Benzalkonium Chloride (BKC) | 0.003-0.02 |
| 3 | Boric Acid | 0.5-1.5 |
| 4 | Sodium Chloride | 0.01-0.1 |
| 5 | OPTIONAL: Penetration Enhancer | 0.05-0.5 |
| 6 | pH Adjusting Agent(s) | QS to Adjust pH to 3.5-5.5 |
| 7 | Water for Injection | QS to 100% Volume |

TABLE 5

Exemplary Formulation B. Pilocarpine Solution + Sodium Citrate Dihydrate (without Borate).

| No. | Ingredient | Percentage (w/v) in Composition |
|---|---|---|
| 1 | Pilocarpine Compound | 1-3 |
| 2 | Benzalkonium Chloride (BKC) | 0.003-0.02 |
| 3 | Sodium Citrate Dihydrate | 0.005-0.09 |
| 4 | Sodium Chloride | 0.01-0.1 |
| 5 | OPTIONAL: Penetration Enhancer | 0.05-0.5 |
| 6 | pH Adjusting Agent(s) | QS to Adjust pH to 3.5-5.5 |
| 7 | Water for Injection | QS to 100% Volume |

TABLE 6

Exemplary Formulation C. Pilocarpine Solution without Borate or Citrate Buffer(s).

| No. | Ingredient | Percentage (w/v) in Composition |
|---|---|---|
| 1 | Pilocarpine Compound | 1-3 |
| 2 | Benzalkonium Chloride (BKC) | 0.003-0.02 |
| 3 | Sodium acetate | 0.2-1.5 |
| 4 | Sodium Chloride | 0.01-0.1 |
| 5 | OPTIONAL: Penetration Enhancer | 0.05-0.5 |
| 6 | pH Adjusting Agent(s) | QS to Adjust pH to 3.5-5.5 |
| 7 | Water for Injection | QS to 100% Volume |

Example 2

Table 7 below provide exemplary Formulation D provided as a gel, providing a list of ingredients suitable for a composition of the present invention provided in gel form.

TABLE 7

Exemplary Formulation D. Pilocarpine Gel.

| No. | Ingredient | Percentage (w/v) in Composition |
|---|---|---|
| 1 | Pilocarpine Compound | 0.5-2.5 |
| 2 | Cremophor | 0.05-0.8 |
| 3 | Benzalkonium chloride (BKC) | 0.003-0.02 |
| 4 | Tromethamine | 0.05-0.5 |
| 5 | Mannitol | 3-6 |
| 6 | Gellan gum | 0.1-1 |
| 7 | OPTIONAL: Penetration Enhancer | 0.05-1 |
| 8 | pH Adjusting Agent(s) | Q.S. to Adjust pH to 3.5-5.5 |
| 9 | Water for Injection | QS to 100% Volume |

Example 3

Table 8 below provides specific examples of suitable compositions according to Formulations A, B, and C of Example 1, provided as solutions.

TABLE 8

Exemplary Compositions of the Invention Provided as Solutions.

| | Percentage (w/v) in Composition | | | | | |
|---|---|---|---|---|---|---|
| Ingredient | Comp. 1: Pilo.* without Citrate | Comp. 2: Pilo. without Borate | Comp. 3: Pilo. without Borate or Citrate Buffers | Comp. 4: Pilo. + PE**, without Citrate | Comp. 5: Pilo. + PE, without Borate | Comp. 6: Pilo + PE, without Borate or Citrate Buffers |
| Pilocarpine HCl | 1.25 | 1.25 | 1.25 | 1.25 | 1.25 | 1.25 |
| Benzalkonium Chloride (BKC) | 0.0075 | 0.0075 | 0.0075 | 0.0075 | 0.0075 | 0.0075 |
| Boric Acid | 1 | — | — | 1 | — | — |
| Sodium Citrate Dihydrate | — | 0.022 | — | — | 0.022 | — |
| Acetate Buffer (Sodium Acetate) | — | — | 0.75 | — | — | 0.75 |
| Penetration Enhancer (PE), e.g., Polysorbate 80 | — | — | — | 0.25 | 0.25 | 0.25 |

TABLE 8-continued

Exemplary Compositions of the Invention Provided as Solutions.

Percentage (w/v) in Composition

| Ingredient | Comp. 1: Pilo.* without Citrate | Comp. 2: Pilo. without Borate | Comp. 3: Pilo. without Borate or Citrate Buffers | Comp. 4: Pilo. + PE **, without Citrate | Comp. 5: Pilo. + PE, without Borate | Comp. 6: Pilo + PE, without Borate or Citrate Buffers |
|---|---|---|---|---|---|---|
| Sodium Chloride | 0.07 | 0.08 | 0.08 | 0.07 | 0.08 | 0.08 |
| Sodium Hydroxide | Q.S. to Adjust pH to 4.5 | Q.S. to Adjust pH to 4.5 | Q.S. to Adjust pH to 4.5 | Q.S. to Adjust pH to 4.5 | Q.S. to Adjust pH to 4.5 | Q.S. to Adjust pH to 4.5 |
| Hydrochloric Acid | Q.S. to Adjust pH to 4.5 | Q.S. to Adjust pH to 4.5 | Q.S. to Adjust pH to 4.5 | Q.S. to Adjust pH to 4.5 | Q.S. to Adjust pH to 4.5 | Q.S. to Adjust pH to 4.5 |
| Water for Injection | QS to 100% volume | QS to 100% volume | QS to 100% volume | QS to 100% volume | QS to 100% volume | OS to 100% volume |

*"Pilo." = pilocarpine. ** "PE" = penetration enhancer.

Example 4

The following manufacturing process can be used to manufacture Composition 1, Composition 2, or Composition 3 of Table 8, Example 3.

Part 1. Bulk Solution Manufacturing

The manufacturing vessel/reactor vessel is sterilized with about 120 kg of water for injection (WFI). This establishes a sterilized "reactor vessel".

About 120 kg of water for injection (WFI) at a temperature of not less than about 70° C., e.g., at a temperature of between 70° C.-80° C., is collected in a manufacturing vessel, such as, e.g., a stainless-steel (SS) manufacturing vessel.

The WFI is cooled to about 20° C.-about 25° C., such as by circulating the water through a water jacket. While cooling, e.g., simultaneously with cooling, 0.2μ-filtered nitrogen is bubbled through the WFI, with all WFI collected in the manufacturing vessel.

The dissolved oxygen content of the WFI is routinely tested to ensure that the WFI reaches a dissolved oxygen content of no more than 2 ppm.

Nitrogen bubbling is continued throughout the bulk solution manufacturing process.

About 60 kg of WFI is transferred into a separate holding vessel. This WFI is used for rinsing, preparation of 0.1N hydrochloric acid (for pH adjustment), and preparation of 0.1N sodium hydroxide solution (for pH adjustment), and for bringing the final composition up to a target final volume.

A suitable stirrer is set to a speed of about 400 rpm±about 100 rpm within the manufacturing vessel containing about 60 kg of WFI. The mixing speed is adjusted as necessary based on/according to the equipment and batch, e.g., vessel geometry and the stirring dynamics during the manufacture of the batch.

The total required quantity of benzalkonium chloride (BKC) solution is added to the manufacturing vessel. The container used to add the BKC is rinsed multiple times, e.g., about 5 times, with approximately 50 mL of WFI each time. The rinses are added to the manufacturing vessel. Stirring is continued for at least about 10 minutes, such as for about 15 to 17 minutes, or for a sufficient time to ensure complete dissolution and composition uniformity.

The total required quantity of buffer, such as either citrate buffer or borate buffer, are added to the manufacturing vessel. In compositions lacking a buffer, this step is omitted. Stirring is continued for at least about 10 minutes, such as for about 15 minutes, or for a sufficient time to ensure complete dissolution of any buffer component/ingredient and composition uniformity.

The total required quantity of sodium chloride is added to the manufacturing vessel and stirring is continued to ensure its complete dissolution.

The total required quantity of pilocarpine HCl is added to the manufacturing vessel. The container used to add the pilocarpine HCl is rinsed multiple times, e.g., about 3 times, with approximately 25 mL WFI each time. The rinses are added to the manufacturing vessel. Stirring is continued for at least about 15 minutes, such as for about 30 minutes, or for a sufficient time to ensure complete dissolution of the pilocarpine HCl and composition uniformity.

The volume in the manufacturing vessel is brought up to a volume of about 90 L (e.g., about 90 Kg) using the reserved WFI. The resulting composition in the manufacturing vessel is stirred for at least about 15 minutes, such as for about 30 to about 32 minutes or for a sufficient amount of time to ensure composition uniformity.

The composition (e.g., the solution) is checked for visual clarity to ensure that there are no undissolved particles in the solution. Stirring is continued until visual clarity is achieved. The resulting solution is referred to as the bulk solution.

The pH of the bulk solution is checked. If required, the pH of the bulk solution is adjusted to between about 4.4 to about 4.6, such as about 4.5 using 0.1N sodium hydroxide solution or 0.1N hydrochloric acid solution. The bulk solution is mixed for about 5 minutes after every addition of sodium hydroxide or hydrochloric acid before measuring the pH during pH adjustment.

The final volume of the bulk solution in the manufacturing vessel is brought up to a final volume of about 100 L, using reserved WFI. The resulting bulk solution is stirred for at least about 10 minutes such as about 15 minutes, or for a sufficient time to ensure uniformity of the bulk solution. The final bulk solution is checked to confirm that the pH of the solution is between about 4.4 to about 4.6. The pH of the solution is adjusted, if necessary, with stirring and final pH confirmation repeated, as necessary.

Part 2. Filtration
2.1 Offline Filtration

After completion of the preparation of the bulk solution, the filtration process is initiated under laminar air flow (LAF).

Prior to initiation of the filtration process, a 0.2 μm capsule or cartridge filter is integrity tested using a water bubble point test against the filter manufacturer's specification. The result should be a pressure of not less than 46 psi under a filtration pressure limit of between about 0.8 kg/cm$^2$ to about 1.8 kg/cm$^2$.

Prior to the start of filtration activity, the filtration unit is flushed with about 200 mL to about 220 mL of the bulk solution. The bulk solution is held inside of the filtration unit for about 2 minutes during the flush. The bulk solution used for the flush is then discarded. The flushing procedure is repeated two additional times for a total of 3 flushes.

After flushing, filtration of the bulk solution is initiated. The bulk solution is filtered through the pre-sterilized, tested, and flushed 0.2 μm capsule or cartridge filter. All filtrate is collected in a sterile receiving vessel.

Upon completion of filtration, the filtrate within the sterile receiving vessel is overlayed with 0.2 μm-filtered nitrogen.

The receiving vessel is transferred to a sterile storage area and stored under laminar air flow until initiation of the filling activity.

A post-filtration integrity test of the filter is performed using a water bubble point test. The result should be a pressure of not less than 39.2 psi under a filtration pressure limit of between about 0.8 kg/cm$^2$ to about 1.8 kg/cm$^2$.

2.1 Online Filtration

Prior to the initiation of filling and capping activity, the bulk solution is filtered through another 0.2μ pre-sterilized capsule or cartridge filter.

Pre-integrity filter testing is performed using a water bubble point test against the filter manufacturer's specification. The result should be a pressure of not less than 46 psi under a filtration pressure limit of between about 0.8 kg/cm$^2$ to about 1.8 kg/cm$^2$. The filter is then connected to the filling line through a pre-sterilized vessel, e.g., buffer tank.

Prior to the initiation of filtration activity, the filter/filtration unit is flushed with about 200 to about 220 mL of the bulk solution. The bulk solution is held within the filtration unit for about 2 minutes during this flushing process and is then discarded. The flushing process is repeated at least two additional times for a total of at least about 3 flushes, with the bulk solution used for flushing discarded after each flush.

After completely discarding the filter flush solution, the entire quantity of remaining bulk solution is filtered into the sterile vessel, e.g., the sterile buffer tank.

The filling activity is then initiated.

Upon the completion of the filling activity, a post-filtration integrity test of the filter is performed using a water bubble point test. The result should be a pressure of not less than 39.2 psi under a filtration pressure limit of between about 0.8 kg/cm$^2$ to about 1.8 kg/cm$^2$.

Part 3. Filling and Capping

Suitable sterile containers, such as sterile vials, are each filled to a volume of between about 2.6 mL to about 2.8 mL (about 2.62 g to about 2.82 g), such as about 2.7 mL (about 2.72 g).

After filling, the head space of each vial is flushed with filtered nitrogen, e.g., using a minimum nitrogen flow of about 2 L/min.

Example 5

The following manufacturing process can be used to manufacture Composition 4, Composition 5, or Composition 6 of Table 8, Example 3.

Part 1. Bulk Solution Manufacturing

The manufacturing vessel/reactor vessel is sterilized with about 120 kg of water for injection (WFI). This establishes a sterilized "reactor vessel".

About 120 kg of water for injection (WFI) at a temperature of not less than about 70° C. is collected in a manufacturing vessel, such as, e.g., a stainless-steel (SS) vessel.

The WFI is cooled to about 20° C.-about 25° C., such as by circulating the water through a water jacket. While cooling, e.g., simultaneously with cooling, 0.2μ-filtered nitrogen is bubbled through the WFI, with all WFI collected in the manufacturing vessel.

The dissolved oxygen content of the WFI is routinely tested to ensure that the WFI reaches a dissolved oxygen content of no more than 2 ppm.

Nitrogen bubbling is continued throughout bulk solution manufacturing.

About 50 kg of WFI is transferred into a separate holding vessel. This WFI is used for rinsing, preparation of 0.1N hydrochloric acid (for pH adjustment), and preparation of 0.1N sodium hydroxide solution (for pH adjustment), and for bringing the final composition up to a target final volume.

A suitable stirrer is set to a speed of about 400 rpm±about 100 rpm within the manufacturing vessel containing about 70 kg of WFI. The mixing speed is adjusted as necessary based on/according to the equipment and batch, e.g., vessel geometry and the stirring dynamics.

The total required quantity of benzalkonium chloride (BKC) solution is added to the manufacturing vessel. The container used to add the BKC is rinsed multiple times, e.g., about 5 times, with approximately 50 mL of WFI each time. The rinses are added to the manufacturing vessel. Stirring is continued for at least about 10 minutes, such as for about 15 to 17 minutes, or for a sufficient time to ensure complete dissolution and composition uniformity.

The total required quantity of polysorbate 80 is added to the manufacturing vessel. The container used to add the polysorbate 80 is rinsed multiple times, e.g., about 5 times, with approximately 50 mL of WFI each time. The rinses are added to the manufacturing vessel under stirring. Stirring is continuous from the beginning of the process to the end of the process, unless otherwise indicated.

The total required quantity of buffer, such as either citrate buffer or borate buffer, are added to the manufacturing vessel. In compositions lacking a buffer, this step is omitted. Stirring is continued for at least about 10 minutes, such as for about 15 minutes, or for a sufficient time to ensure complete dissolution of any buffer component/ingredient and composition uniformity.

The total required quantity of sodium chloride is added to the manufacturing vessel and stirring is continued to ensure its complete dissolution.

The total required quantity of pilocarpine HCl is added to the manufacturing vessel. The container used to add the pilocarpine HCl is rinsed multiple times, e.g., about 3 times, with approximately 25 mL WFI each time. The rinses are added to the manufacturing vessel. Stirring is continued for at least about 15 minutes, such as for about 30 minutes, or for a sufficient time to ensure complete dissolution of pilocarpine HCl and composition uniformity.

The volume in the manufacturing vessel is brought up to a volume of about 90 L (e.g., about 90 Kg) using the reserved WFI. The resulting composition in the manufacturing vessel is stirred for at least about 15 minutes, such as for about 30 to about 32 minutes or for a sufficient amount of time to ensure composition uniformity.

The composition (e.g., the solution) is checked for visual clarity to ensure that there are no undissolved particles in the solution. Stirring is continued until visual clarity is achieved. The resulting solution is referred to as the bulk solution.

The pH of the bulk solution is checked. If required, the pH of the bulk solution is adjusted to about 4.4 to about 4.6, e.g., about 4.5 using 0.1N sodium hydroxide solution or 0.1N hydrochloric acid solution. The bulk solution is mixed for about 5 minutes after each addition of sodium hydroxide or hydrochloric acid before measuring the pH during pH adjustment.

The final volume of the bulk solution in the manufacturing vessel is brought up to a final volume of about 100 L, using reserved WFI. The resulting bulk solution is stirred for at least about 10 minutes such as about 15 minutes, or for a sufficient time to ensure uniformity of the bulk solution. The final bulk solution is checked to confirm that the pH of the solution is between about 4.4 to about 4.6. The pH of the solution is adjusted, if necessary, with stirring and final pH confirmation repeated, as necessary.

Part 2. Filtration 2.1 Offline Filtration

After completion of the preparation of the bulk solution, the filtration process is initiated under laminar air flow (LAF).

Prior to initiation of the filtration process, a 0.2 µm capsule or cartridge filter is integrity tested using a water bubble point test against the filter manufacturer's specification. The result should be a pressure of not less than 46 psi under a filtration pressure limit of between about 0.8 kg/cm$^2$ to about 1.8 kg/cm$^2$.

Prior to the start of filtration activity, the filtration unit is flushed with about 200 mL to about 220 mL of the bulk solution. The bulk solution is held inside of the filtration unit for about 2 minutes during the flush. The bulk solution used for the flush is then discarded. The flushing procedure is repeated two additional times for a total of 3 flushes.

After flushing, filtration of the bulk solution is initiated. The bulk solution is filtered through the pre-sterilized, tested, and flushed 0.2 µm capsule or cartridge filter. All filtrate is collected in a sterile receiving vessel.

Upon completion of filtration, the filtrate within the sterile receiving vessel is overlayed with 0.2 µm-filtered nitrogen.

The receiving vessel is transferred to a sterile storage area and stored under laminar air flow until initiation of the filling activity.

A post-filtration integrity test of the filter is performed using a water bubble point test. The result should be a pressure of not less than 39.2 psi under a filtration pressure limit of between about 0.8 kg/cm$^2$ to about 1.8 kg/cm$^2$.

2.2 Online Filtration

Prior to the initiation of filling and capping activity, the bulk solution is filtered through another 0.2µ pre-sterilized capsule or cartridge filter.

Pre-integrity filter testing is performed using a water bubble point test against the filter manufacturer's specification. The result should be a pressure of not less than 46 psi under a filtration pressure limit of between about 0.8 kg/cm$^2$ to about 1.8 kg/cm$^2$. The filter is then connected to the filling line through a pre-sterilized vessel, e.g., buffer tank.

Prior to the initiation of filtration activity, the filter/filtration unit is flushed with about 200 to about 220 mL of the bulk solution. The bulk solution is held within the filtration unit for about 2 minutes during this flushing process and is then discarded. The flushing process is repeated at least two additional times for a total of at least about 3 flushes, with the bulk solution used for flushing discarded after each flush.

After completely discarding the filter flush solution, the entire quantity of remaining bulk solution is filtered into the sterile vessel, e.g., the sterile buffer tank.

The filling activity is then initiated.

Upon the completion of the filling activity, a post-filtration integrity test of the filter is performed using a water bubble point test. The result should be a pressure of not less than 39.2 psi under a filtration pressure limit of between about 0.8 kg/cm$^2$ to about 1.8 kg/cm$^2$.

Part 3. Filling and Capping

Suitable sterile containers, such as sterile vials, are each filled to a volume of about 2.6 mL to about 2.8 mL (~2.62 g-~2.82 g), such as about 2.7 mL (about 2.72 g).

After filling, the head space of each vial is flushed with filtered nitrogen, e.g., using a minimum nitrogen flow of about 2 L/min.

Example 6

Table 9 below provides specific examples of suitable compositions according to Formulation D of Example 2, provided as a gel.

TABLE 9

Exemplary Compositions of the Invention Provided as a Gel. (Percentage (w/v) in Composition)

| Ingredient | Comp. 7: Pilocarpine Gel | Comp. 8: Pilocarpine Gel + PE* |
|---|---|---|
| Pilocarpine HCl | 1.25 | 1.25 |
| Cremophor | 0.25 | 0.25 |
| Benzalkonium Chloride (BKC) | 0.0075 | 0.0075 |
| Tromethamine | 0.185 | 0.185 |
| Mannitol | 4.5 | 4.5 |
| Gellan Gum | 0.6 | 0.6 |
| Polysorbate 80 | — | 0.5 |
| Sodium Hydroxide | Q.S. to Adjust pH to 4.5 | Q.S. to Adjust pH to 4.5 |
| Hydrochloric Acid | Q.S. to Adjust pH to 4.5 | Q.S. to Adjust pH to 4.5 |
| Water for Injection | QS to 100% Volume | QS to 100% Volume |

*"PE" = penetration enhancer.

Example 7

The following manufacturing process can be used to manufacture Composition 7 or Composition 8, of Table 9, Example 6.

Part 1. Bulk Solution Manufacturing 1.1 Preparation of Polymer Phase Solution

A first (filter no. 1) and a second (filter no. 2) 0.2 µm capsule filter are each integrity-tested using a water bubble point test against the filter manufacturer's specification(s). The result of each test should be a pressure of not less than 46.0 psi under a filtration pressure limit of between about 0.8 kg/cm$^2$ to about 1.8 kg/cm$^2$. Upon completion of integrity testing, filters are flushed with nitrogen to remove any residual water from the filter pores.

The outlet of filter no. 2 is connected to the inlet of filter No. 1 using a suitable connection mechanism, such as Pharma 50 silicone tubing of a suitable length, such as about 60 cm. The outlet of filter no. 1 is connected to a diaphragm valve. The inlet of filter no. 2 is connected to a suitable connection mechanism, such as Pharma 50 silicone tubing of suitable length, such as about 2.30 meters. The entire assembly is sterilized using a suitable sterilization method such as autoclaving. During sterilization, e.g., while autoclaving, the diaphragm valve is maintained in an open position. Upon completion of sterilization, e.g., after autoclaving, the diaphragm valve is closed under aseptic conditions. The entire assembly is then connected to an empty manufacturing vessel (e.g., a "reactor vessel").

The manufacturing vessel/reactor vessel is sterilized with about 120 kg of water for injection (WFI). This establishes a sterilized "reactor vessel".

About 120 kg of water for injection (WFI) at a temperature of not less than about 70° C. is collected in a manufacturing vessel, such as, e.g., a stainless-steel (SS) vessel.

The WFI is cooled to about 20° C.-about 25° C., such as by circulating the water through a water jacket. While cooling, e.g., simultaneously with cooling, 0.2µ-filtered nitrogen is bubbled through the WFI, with all WFI collected in the manufacturing vessel.

The dissolved oxygen content of the WFI is routinely tested to ensure that the WFI reaches a dissolved oxygen content of no more than 2 ppm.

Nitrogen bubbling is continued throughout bulk solution manufacturing.

After completion of empty reactor sterilization, about 50 Kg of the 120 Kg of WFI is transferred to a second manufacturing vessel, e.g., a stainless-steel manufacturing vessel, to be used in the preparation of a drug phase and bringing composition(s) up to volume.

While maintaining the temperature of the remaining 70 Kg WFI in the reactor vessel between about 73° C. and 78° C., a suitable stirrer in the reactor vessel is set to a stirrer speed of about 125 rpm±about 50 rpm. The mixing speed is adjusted as necessary based on/according to the equipment and batch, e.g., vessel geometry and the stirring dynamics during the manufacture of the batch.

The required quantity of gellan gum NF (national formulary) is added to the reactor vessel and stirring is maintained at about 125 rpm±about 50 rpm for at least about 30 minutes, such as about 60 mins, or for a sufficient time to ensure complete dissolution of the gellan gum. The solution is maintained at a temperature of between about 73° C. and about 78° C. during the continuous stirring.

After complete dissolution of gellan gum, the solution is cooled to between about 20° C. and about 25° C. under constant stirring. This establishes the "polymer phase".

The polymer phase is sterilized at set temperature of about 122.0° C. for about 20 minutes while constantly stirring at speed of about 125 rpm±about 50 rpm.

Upon completion of sterilization, the polymer phase is cooled to about 25° C. While cooling, when the temperature of the polymer phase reaches about 60° C., the stirring speed is increased to a stirring speed of about 250 rpm±50 rpm.

1.2 Preparation of Drug Phase Solution

About 50 kg of the reserved, cooled WFI is collected in a suitable manufacturing vessel. A suitable stirrer in the manufacturing vessel is set to a stirring speed of about 300 rpm±50 rpm. The mixing speed is adjusted as necessary based on/according to the equipment and batch, e.g., vessel geometry and the stirring dynamics during the manufacture of the batch.

The total required quantity of pilocarpine HCl is added to the manufacturing vessel, followed by the addition of the total required quantity of benzalkonium chloride. The resulting composition is mixed until the two components are completely dissolved.

The total required quantity of polysorbate 80 is added to the manufacturing vessel. The resulting composition is mixed until the polysorbate 80 is completely dissolved.

Upon the complete dissolution of the pilocarpine HCl, benzalkonium chloride, and polysorbate 80, the total required quantity of cremophor to the solution. The resulting composition is mixed for a suitable period of time to allow complete dissolution of cremophor.

Upon the complete dissolution of the cremophor, the total required quantity of mannitol is added to the solution. The resulting composition is mixed for a suitable period of time to allow the mannitol to completely dissolve.

Upon the complete dissolution of the mannitol, the total required quantity of tromethamine is added to the solution. The resulting composition is mixed for a sufficient period of time, such as about 10 minutes, to ensure complete dissolution of the tromethamine.

The composition is checked for clarity. Stirring is continued until visual clarity is achieved.

The volume is then brought to about 55 L using previously reserved WFI. The composition is then stirred for about 15 minutes or for a sufficient period of time to ensure composition uniformity. This establishes the "drug phase".

An industry standard sampling protocol is used to sample and test the drug phase to ensure that the phase meets pre-established specification(s). Upon acceptance, the drug phase is transferred to the sterilized polymer phase via aseptic filtration (see below).

1.3 Aseptic Filtration of Drug Phase into Sterile Polymer Phase

Aseptic filtration of the drug phase into the sterile polymer phase is performed at a filtration pressure of between about 0.8 Kg/cm²-about 1.8 Kg/cm².

Prior to beginning the aseptic filtration, the weight of the drug phase is noted. About 55 Kg of the drug phase (which can be referred to as the "concentrated drug phase") is filtered into the reactor vessel containing the polymer phase through the two sterilized 0.2 µm filters connected in series.

WFI is then passed through the filters a number of times, such as about two times with about 2.5 L of WFI each time, and the filtrate added to the reactor vessel each time to ensure all required drug phase is added into the reactor vessel. The resulting composition is then stirred for about 1 hour at a speed of about 250 rpm±about 50 rpm, or for a sufficient period of time (and at a suitable speed) to ensure composition uniformity.

A post-filtration integrity test of the filter is performed using a water bubble point test. The result should be a pressure of not less than 34.8 psi under a filtration pressure limit of between about 0.8 kg/cm² to about 1.8 kg/cm².

the pH of the composition is adjusted using one or more pH adjusting agents. The pH of the solution is adjusted by the addition or one or more pH adjusting agents, with the solution sufficiently mixed after each addition such that the composition has a uniform pH prior to (a) sampling for pH, and (b) applying further pH adjustment as needed. Composition pH is adjusted to a pH of between about 4.4 to about 4.6, such as, e.g., about 4.4, about 4.5, or about 4.6 using the pH adjusting agent(s).

Part 2. Filtration

Filtration of the final combined composition (bulk solution) is then performed using a suitable filter such as an 8 µm PP2 MidiCap® filter (Sartorius).

Before initiating filtration activity, a sterilized 8.0 µm polypropylene filter is flushed with about 100 mL to about 120 mL of bulk solution a number of times such as about 3 times. During each flush, the composition is held in the filtration unit for an extended period of time, such as about 2 minutes, prior to discarding each flush. Upon completion of flushing, filtration of the bulk solution is performed with the filtrate collected in a sterile receiving vessel.

Part 3. Filling and Capping

Suitable sterile containers, such as sterile vials, are each filled to a volume of between about 2.6 mL to about 2.8 mL (about 2.62 g to about 2.82 g), such as about 2.7 mL (about 2.72 g).

After filling, the head space of each vial is flushed with filtered nitrogen, e.g., using a minimum nitrogen flow of about 2 L/min.

Example 8

Three exemplary batches of citrate-free pilocarpine compositions comprising the formulation shown in Table 10 were manufactured.

TABLE 10

Exemplary Compositions of the Invention Used for Stability Testing.

| No. | Ingredient | Percentage (w/v) in Composition |
|---|---|---|
| 1 | Pilocarpine Hydrochloride | 1.25 |
| 2 | Benzalkonium Chloride | 0.0075 |
| 3 | Sodium chloride | 0.08 |
| 4 | Boric acid | 1.0 |
| 5 | Sodium hydroxide | QS for pH adjustment |
| 6 | Hydrochloric acid | QS for pH adjustment |
| 7 | Water for Injection | QS to 100% volume |
| 8 | Nitrogen | Q.S. |

The three exemplary batches of composition having the formulation of Table 10 were subjected to stability and impurities testing at 25±2° C. and 40%±5% relative humidity. Stability data demonstrating the percent of original pilocarpine and benzalkonium chloride compounds present after storage of the compositions under the given storage conditions are provided below in Table 11. Table 11 further provides results of impurities testing before and after storage of the compositions under the given storage conditions.

Data from impurities testing reveals that compositions tested/evaluated under the provided conditions demonstrate stability for a period of at least about 3 months.

This data demonstrates that compositions lacking a citrate buffer component/compound are stable with regard to maintenance of API (demonstrating no significant degradation of API) and avoidance of significant impurity development when stored under typical storage conditions for a commercially relevant period of time, and may be expected to maintain stability for extended period(s) of time such as, e.g., at least about 1, 2, 3, 6, 9, 12, 18, 24, 28, or, e.g., 32 or 36 months or more when stored under typical storage conditions such as, e.g., after storage under conditions comprising a temperature of between about 15° C. and about 42° C. and a relative humidity of between about 35% and about 75% relative humidity, e.g., at about 15° C.-about 27° C. and about 60% relative humidity, after storage at about 38° C.-about 42° C. and 75% relative humidity, after storage at about 23° C.-27° C. and about 35%-45% relative humidity, or when the composition is stored under any one or more of such conditions for such period(s) of time.

The invention claimed is:

1. A pharmaceutically acceptable and ophthalmologically suitable reduced buffer content composition in the form of a solution for treating an ocular condition via administration to a mammalian eye, the reduced buffer content composition comprising an effective amount of a pilocarpine compound, wherein the effective amount of the pilocarpine compound is an amount greater than about 1% w/v of the composition and wherein the pilocarpine compound is the only active pharmaceutical ingredient present in the composition, and an effective amount of a uniform buffering component, wherein the uniform buffering component is present in a concentration such that the concentration of the pilocarpine compound in the composition is at least 1.5 times the concentration of the buffering component in the composition and the concentration of the pilocarpine compound in the composition is less than 4 times the concentration of the buffering component in the composition.

2. The composition of claim 1, wherein the composition maintains a pH of between about 3 and about 6 and at least about 97% of the pilocarpine compound originally present in

TABLE 11

Stability Data. Storage conditions: 25 ± 2° C. and 40% ± 5% relative humidity.

| Batches | Time Interval (Month) | Assay of Pilo. HCl NLT 90.0% and NMT 110.0% | Assay of BKC NLT 75.0% and NMT 110.0% | pH (3.5-5.5) | Osmolality (260-320 mOsm/kg) | Related compounds | | | |
|---|---|---|---|---|---|---|---|---|---|
| | | | | | | Pilocarpic acid NMT 6.8% | Isopilo. NMT 1.2% | Unspec. impurity NMT 0.1% | Total impurities NMT 7.5 % |
| Batch 1 | Initial | 100.1 | 94.8 | 4.6 | 285 | 0.492 | 0.111 | ND | 0.603 |
| | 3 | 98.2 | 97.8 | 4.0 | 282 | 1.550 | 0.140 | ND | 1.690 |
| Batch 2 | Initial | 100.6 | 94.3 | 4.5 | 285 | 0.444 | 0.103 | ND | 0.547 |
| | 3 | 98.1 | 98.1 | 3.9 | 285 | 1.897 | 0.130 | ND | 2.027 |
| Batch 3 | Initial | 100.7 | 93.6 | 4.5 | 284 | 0.407 | 0.095 | ND | 0.502 |
| | 3 | 98.6 | 97.5 | 4.0 | 282 | 1.667 | 0.124 | ND | 1.792 |

(Abbreviations: Pilo (pilocarpine); HCl (hydrochloric acid); BKC (benzalkonium chloride); Unspec. (unspecified); NLT (not less than); NMT (not more than))

Stability testing revealed that all batches (1-3), each free of citrate buffer, maintained greater than 98% of pilocarpine HCl compound which was present at the beginning of the storage period (e.g., present upon manufacturing) after storage at 25±2° C. & 40%±5% relative humidity for at least 3 months.

the composition when the composition is stored under conditions comprising a temperature of about 25° C.±2° C. and a relative humidity of about 40%±5% for a period of at least about one month.

3. The composition of claim 1, wherein the pilocarpine compound is a salt of pilocarpine.

4. The composition of claim 3, wherein the pilocarpine compound is pilocarpine hydrochloride.

5. The composition of claim 4, wherein the composition comprises the pilocarpine hydrochloride in an amount of about 1.25% w/v.

6. The composition of claim 1, wherein the composition further comprises benzalkonium chloride in an amount of between about 0.003% w/v and about 0.009% w/v.

7. The composition of claim 1, wherein the uniform buffering component comprises a single buffer compound.

8. The composition of claim 7, wherein the single buffer compound comprises an acetate buffer compound comprising sodium acetate.

9. The composition of claim 8, wherein the sodium acetate is present in the composition in an amount of between 0.2% w/v and about 1.5% w/v.

10. The composition of claim 7, wherein the ratio of the pilocarpine compound to the single buffer compound is between about 1:0.05 and about 1:3.

11. The composition of claim 8, wherein the composition further comprises benzalkonium chloride in an amount of between about 0.003% w/v and about 0.009% w/v, and the ratio of benzalkonium chloride to the sodium acetate compound is between about 1:20 and about 1:500.

12. The composition of claim 1, wherein the composition further comprises a penetration enhancer component.

13. The composition of claim 12, wherein the penetration enhancer component consists at least essentially of a polyoxyethylene sorbitan fatty acid ester.

14. The composition of claim 13, wherein the penetration enhancer component consists at least essentially of polysorbate 80, and the polysorbate 80 is present in the composition in an amount of between about 0.1% w/v and about 3% w/v of the composition.

15. The composition of claim 11, wherein the composition further comprises a penetration enhancer component.

16. The composition of claim 15, wherein the penetration enhancer component consists at least essentially of a polyoxyethylene sorbitan fatty acid ester.

17. The composition of claim 16, wherein the penetration enhancer component consists at least essentially of polysorbate 80, and the polysorbate 80 is present in the composition in an amount of between about 0.1% w/v and about 3% w/v of the composition.

18. The composition of claim 14, wherein the composition further comprises benzalkonium chloride in an amount of between about 0.003% w/v and about 0.009% w/v, and the ratio of benzalkonium chloride to polysorbate 80 is greater than about 1:1.

19. The composition of claim 18, wherein the ratio of benzalkonium chloride to polysorbate 80 is between about 1:1 and about 1:50.

20. A method of treating presbyopia in a patient in need thereof, the method comprising administration of one to two drops of a reduced buffer content composition in the form of a solution once or twice per day, the reduced buffer content composition comprising an effective amount of a pilocarpine compound, wherein the effective amount of the pilocarpine compound is an amount greater than about 1% w/v of the composition and wherein the pilocarpine compound is the only active pharmaceutical ingredient present in the composition, and a buffering component, wherein the buffering component is present in a concentration such that the concentration of the pilocarpine compound in the composition is at least 1.5 times the concentration of the buffering component in the composition and the concentration of the pilocarpine compound in the composition is less than 4 times the concentration of the buffering component in the composition.

* * * * *